United States Patent
Hirakura et al.

(10) Patent No.: US 7,767,806 B2
(45) Date of Patent: Aug. 3, 2010

(54) HYALURONIC ACID MODIFICATION PRODUCTS AND DRUG CARRIERS USING THEM

(75) Inventors: Tai Hirakura, Gotenba (JP); Teruo Nakamura, Gotenba (JP); Tsuyoshi Shimoboji, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 251 days.

(21) Appl. No.: 10/571,005

(22) PCT Filed: Sep. 8, 2004

(86) PCT No.: PCT/JP2004/013026
§ 371 (c)(1), (2), (4) Date: Mar. 8, 2006

(87) PCT Pub. No.: WO2005/023906
PCT Pub. Date: Mar. 17, 2005

(65) Prior Publication Data
US 2007/0031503 A1    Feb. 8, 2007

(30) Foreign Application Priority Data
Sep. 8, 2003 (JP) .................... 2003-315387
Dec. 5, 2003 (JP) .................... 2003-407681
Sep. 7, 2004 (JP) .................... 2004-259157

(51) Int. Cl.
*C07H 5/04* (2006.01)
*C07H 1/00* (2006.01)
*A61K 31/728* (2006.01)

(52) U.S. Cl. .................... 536/123.1; 536/124; 514/54

(58) Field of Classification Search ............ 536/123.1, 536/124; 514/54
See application file for complete search history.

(56) References Cited

U.S. PATENT DOCUMENTS 6,229,009 B1 * 5/2001 Lambert et al. .......... 536/123.1
2002/0071855 A1  6/2002 Sadozai et al.
2004/0013626 A1 * 1/2004 Gref et al. ............. 424/70.13

FOREIGN PATENT DOCUMENTS

| EP | 048 959 A | 5/1992 |
| EP | 1 310 517 A1 | 5/2003 |
| EP | 1 496 037 A1 | 1/2005 |
| JP | 6188705 | 7/1994 |
| WO | WO 00/01733 | 1/2000 |
| WO | WO 01/88019 | 11/2001 |
| WO | WO 03/087019 A1 | 10/2003 |

OTHER PUBLICATIONS defintion of graft polymer, IUPAC Compendium of Chemical Terminology (the "Gold Book"), 1997, Blackwell Scientific Publications, 2nd ed., http://goldbook.iupac.org, accessed online on Jan. 26, 2009.* defintion of graft macromolecule, IUAPC Compendium of Chemical Terminology (the "Gold Book"), 1997, Blackwell Scientific Publications, 2nd ed., http://goldbook.iupac.org, accessed online on Jan. 26, 2009.*

Caroline Lemarchand et al; "Novel polyester-Polysaccharide Nanoparticles"; Pharmaceutical Research, Aug. 2003; pp. 1284-1292; vol. 20 No. 8.

C. Rouzes et al; "Surface modification pf poly (lactic acid) nanospheres using hydorphobically modified dextrans as stabilizers in an o/w emulsion/evaporation technique."; J. Biomed. Mater. Res., 50, 557-565.

* cited by examiner

*Primary Examiner*—Shaojia Anna Jiang
*Assistant Examiner*—Jonathan S Lau
(74) *Attorney, Agent, or Firm*—Browdy and Neimark, PLLC

(57) ABSTRACT

A hyaluronic acid modification product includes a polymer bonded to hyaluronic acid, the polymer being polylactic acid, polyglycolic acid or lactic acid-glycolic acid copolymer, providing a drug carrier which efficiently encapsulates low molecular weight drugs and provides sustained-release over a long term, control of blood residence, is well dispersible in an aqueous solution, and has excellent biocompatibility.

7 Claims, 23 Drawing Sheets

[Fig. 1]
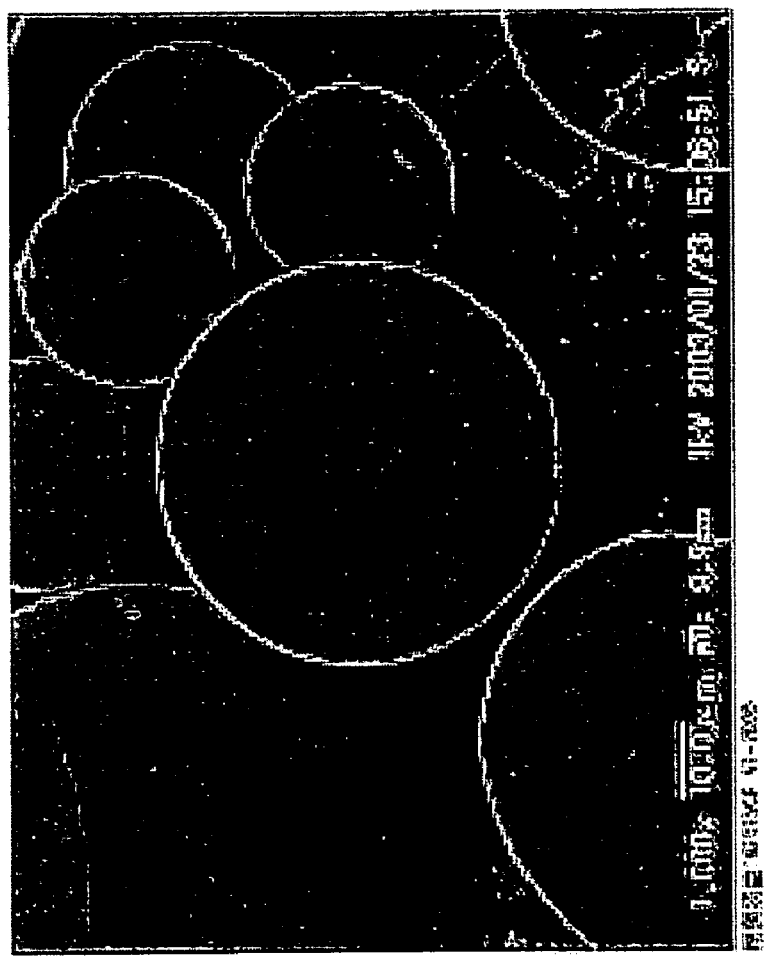

[Fig. 2]
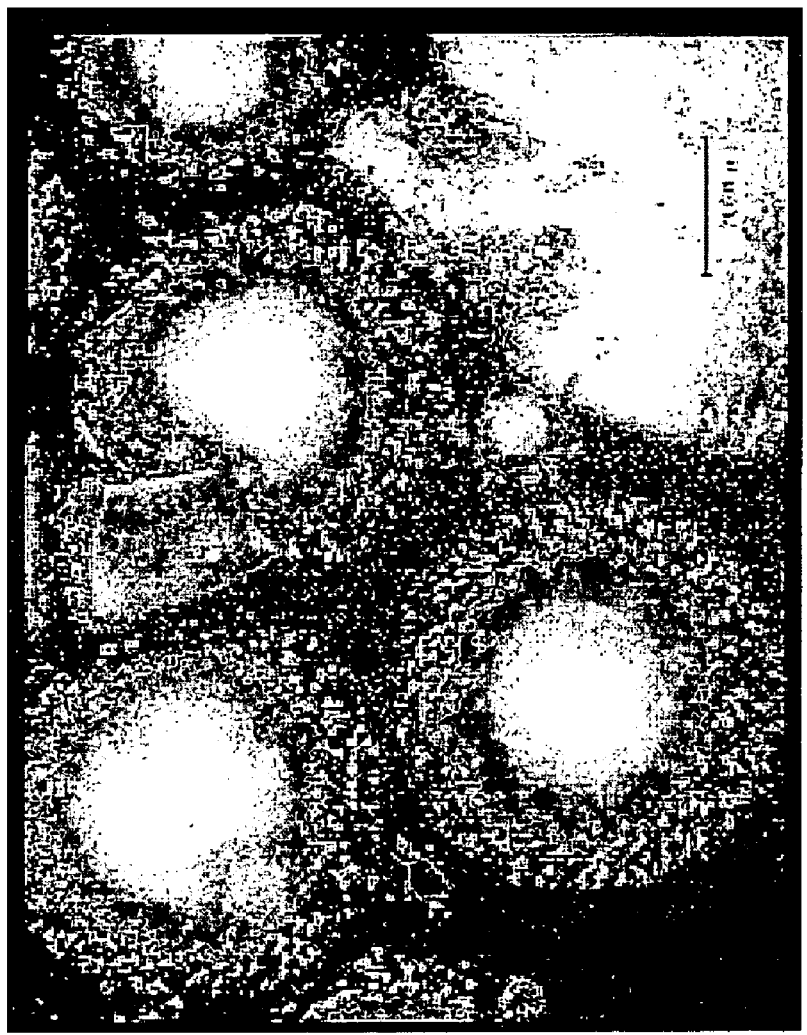

[Fig. 3]
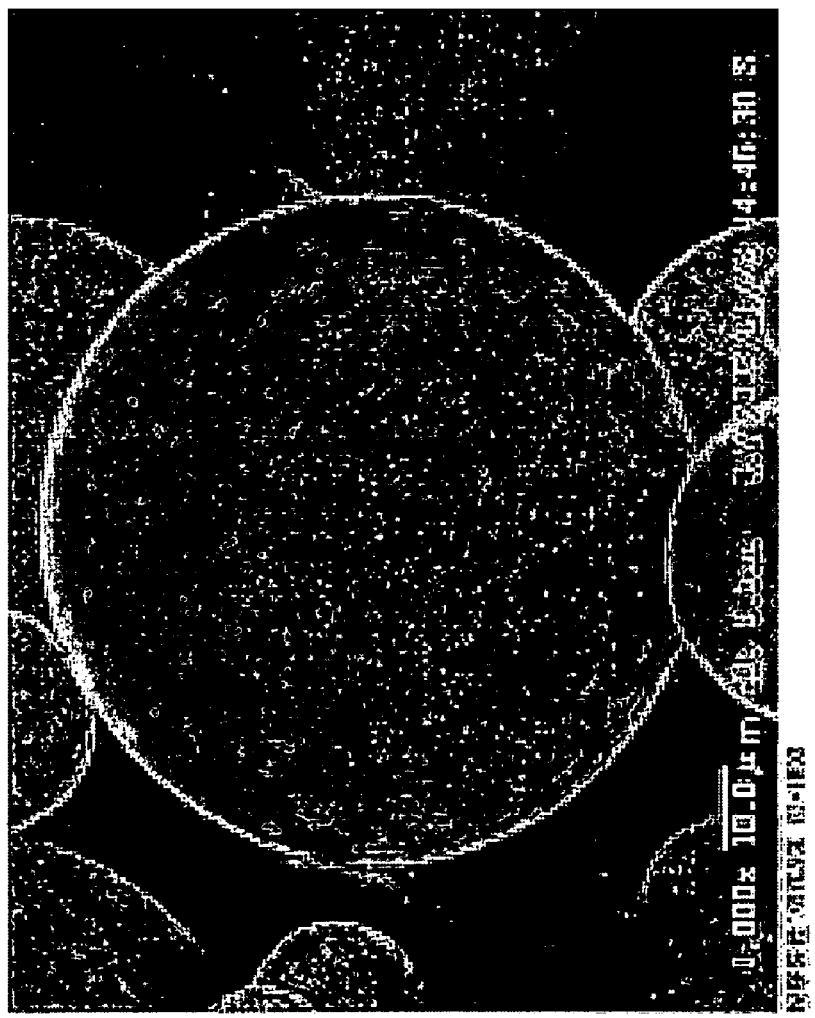

[Fig. 4]
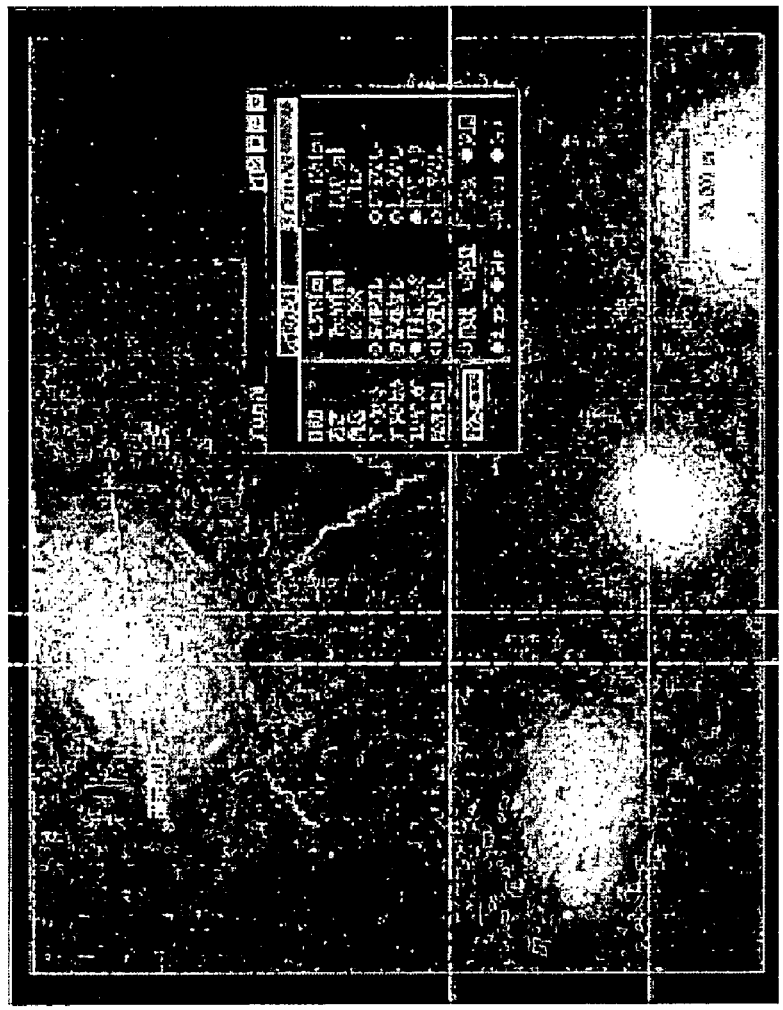

[Fig. 5]
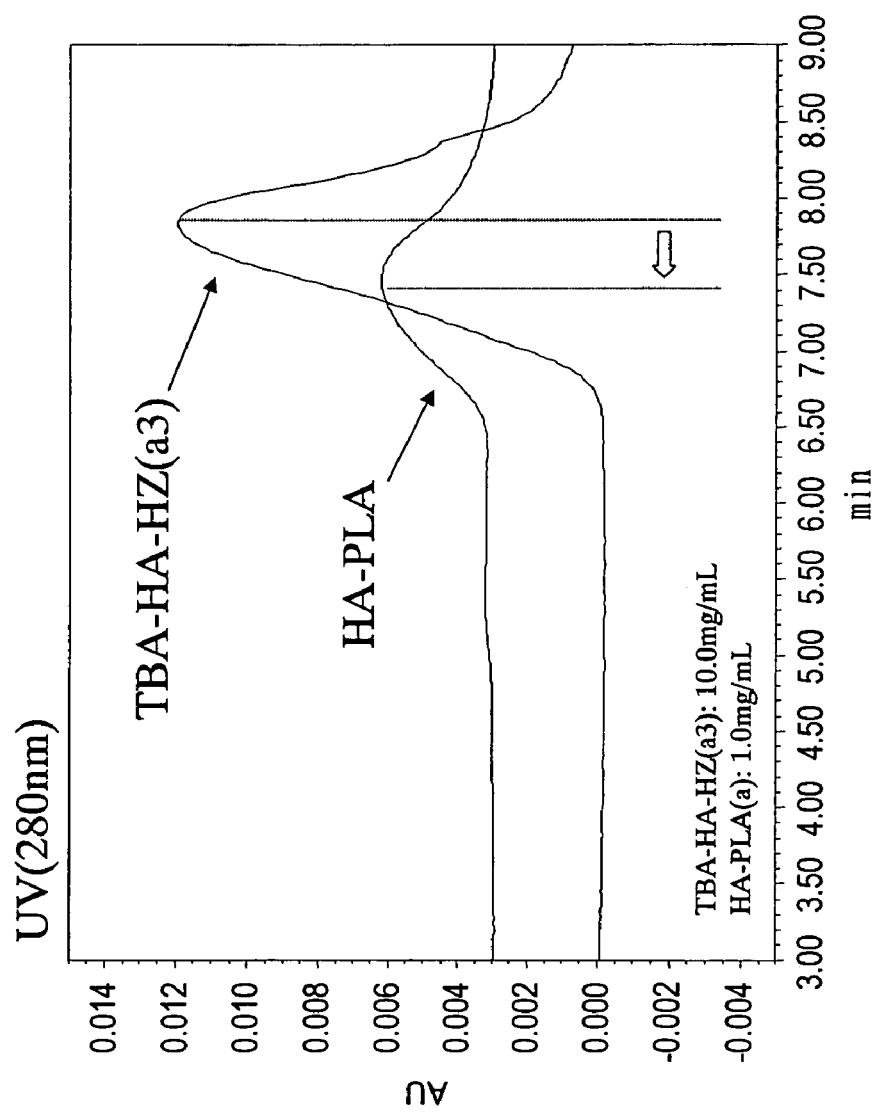

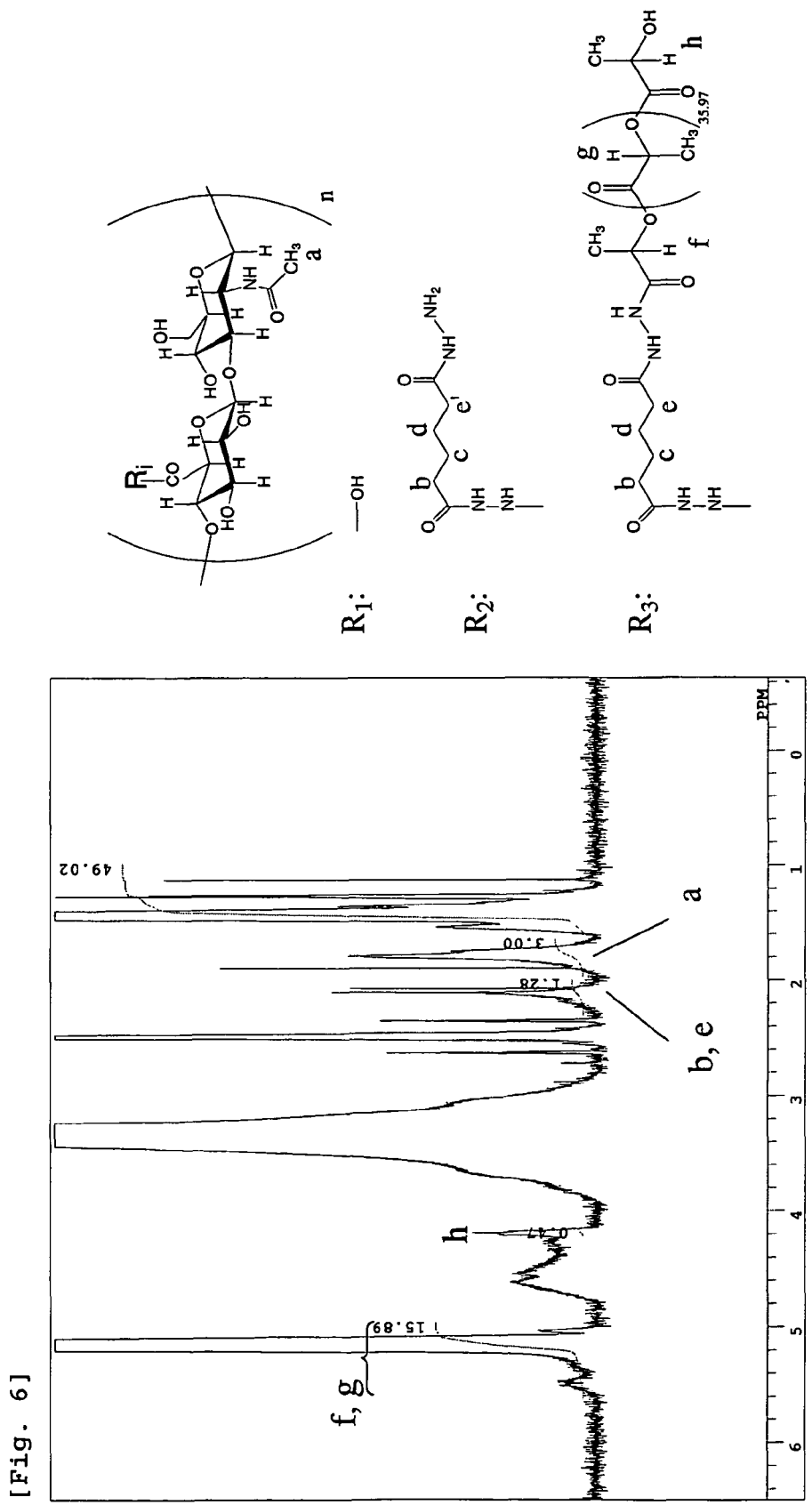

[Fig. 7]

[Fig. 8]

[Fig. 9]
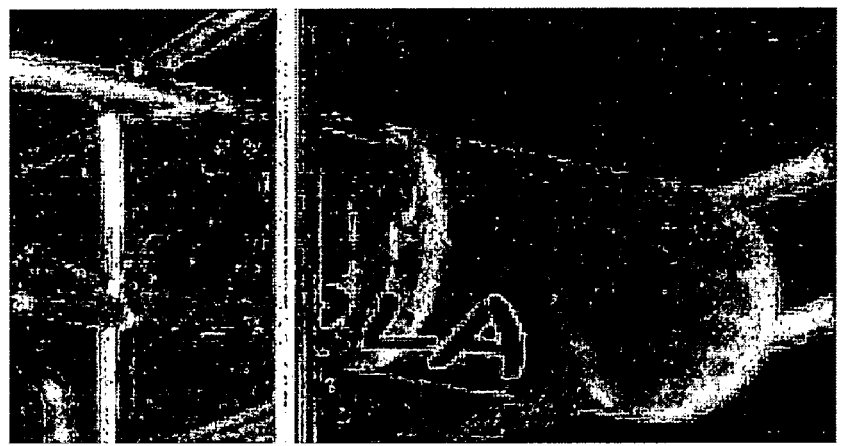

[Fig. 10]
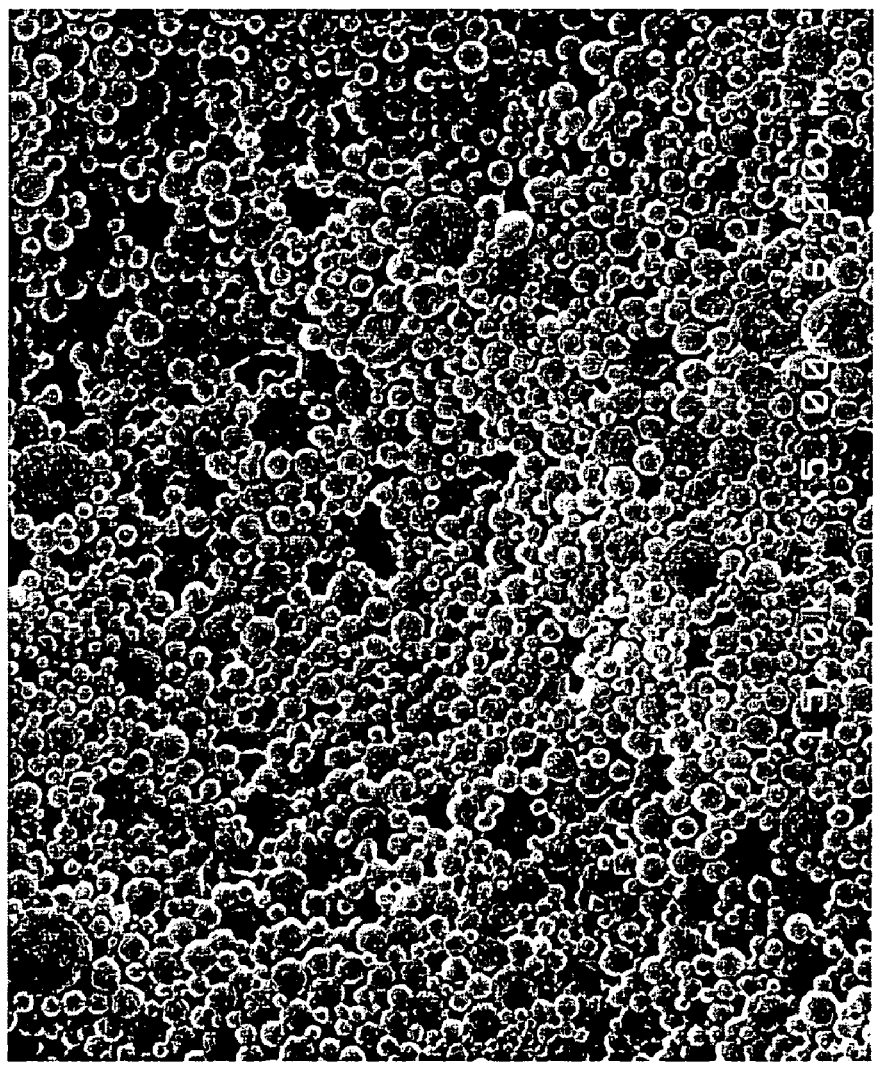

[Fig. 11]
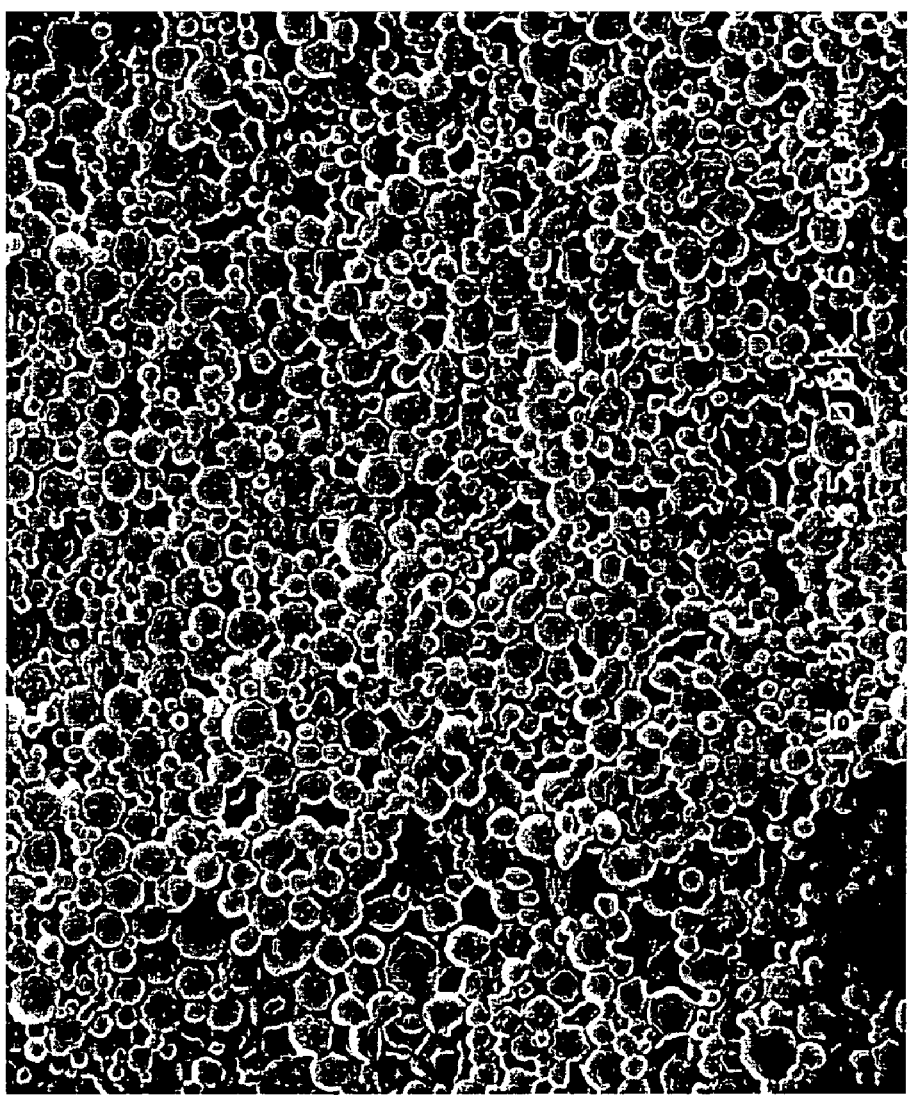

[Fig. 12]
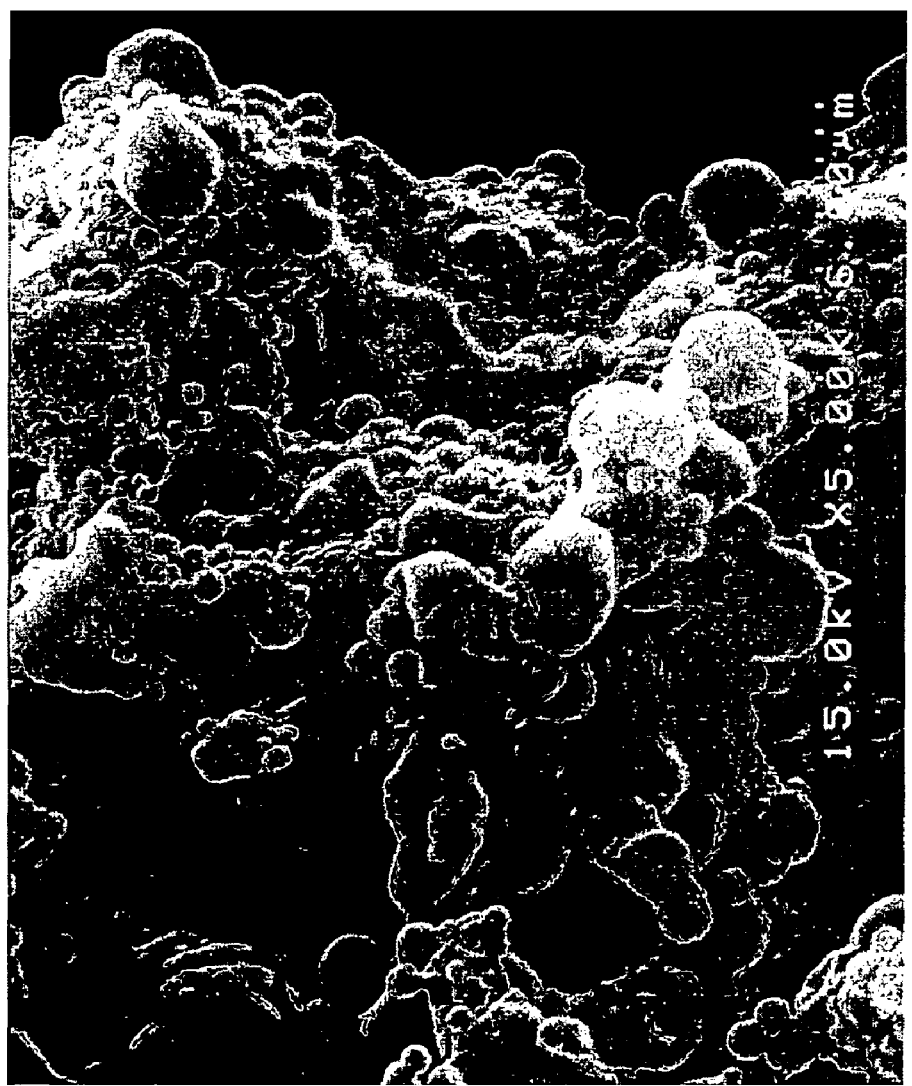

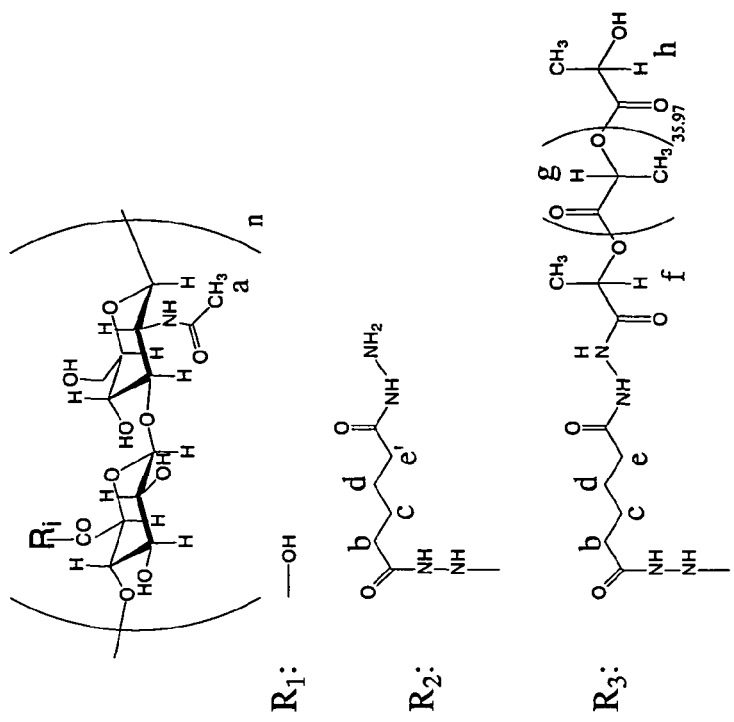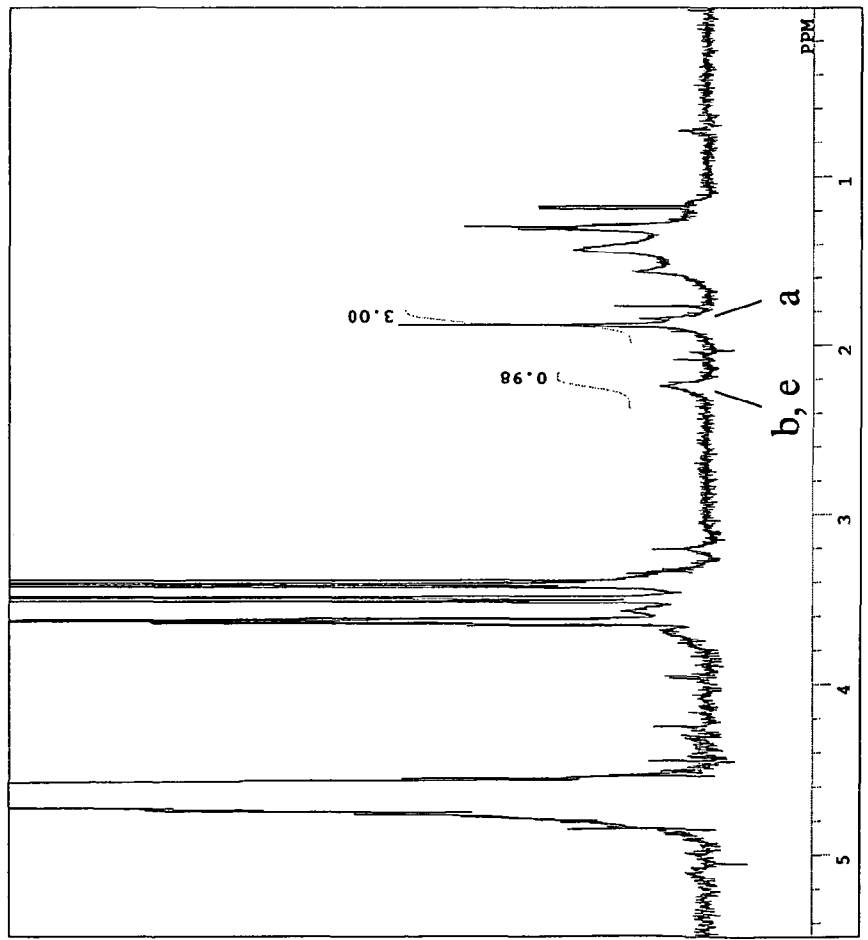
[Fig. 13]
HA-PLANS (D2O)

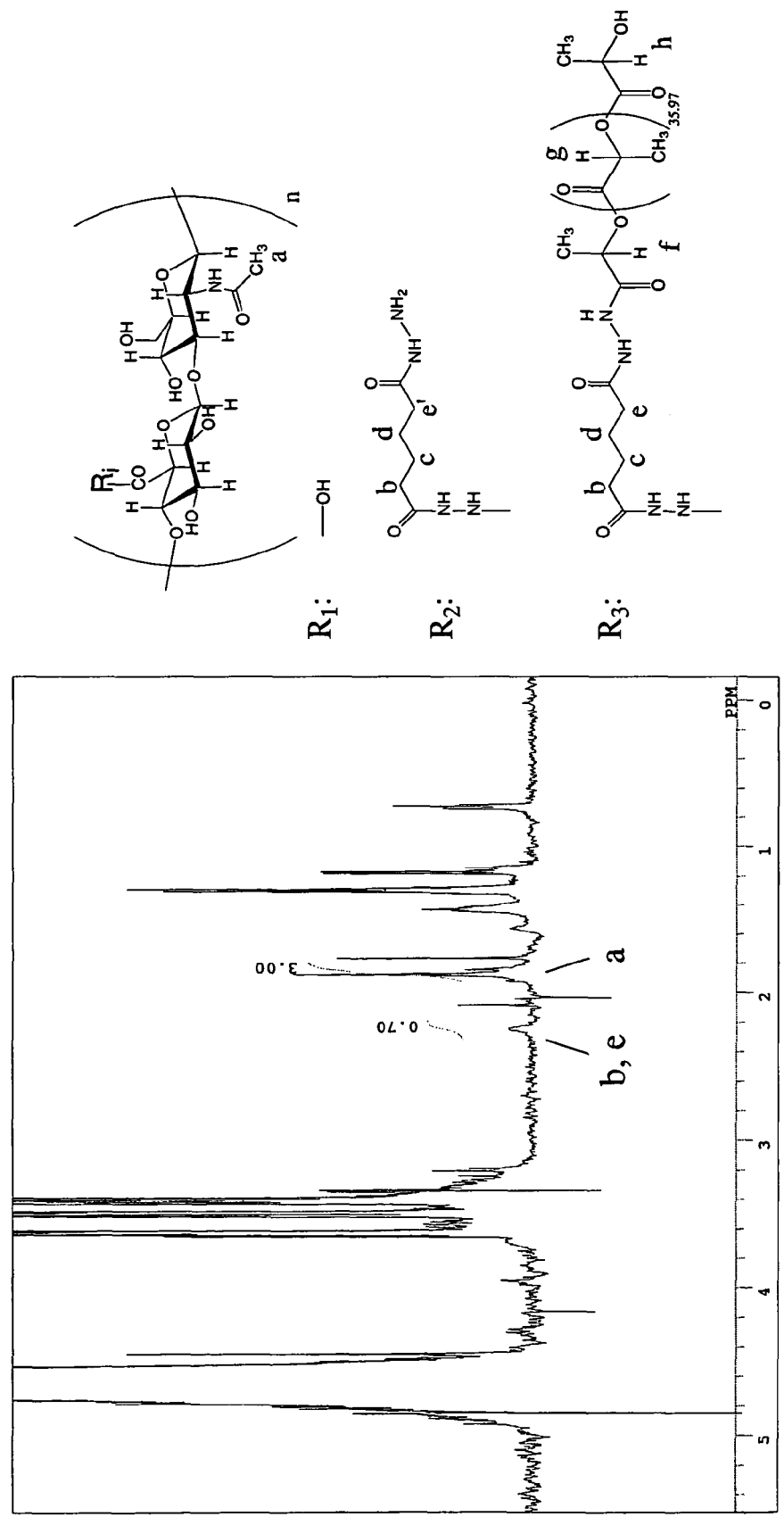
[Fig. 14]
HA-PLA/PLA NS (D₂O)

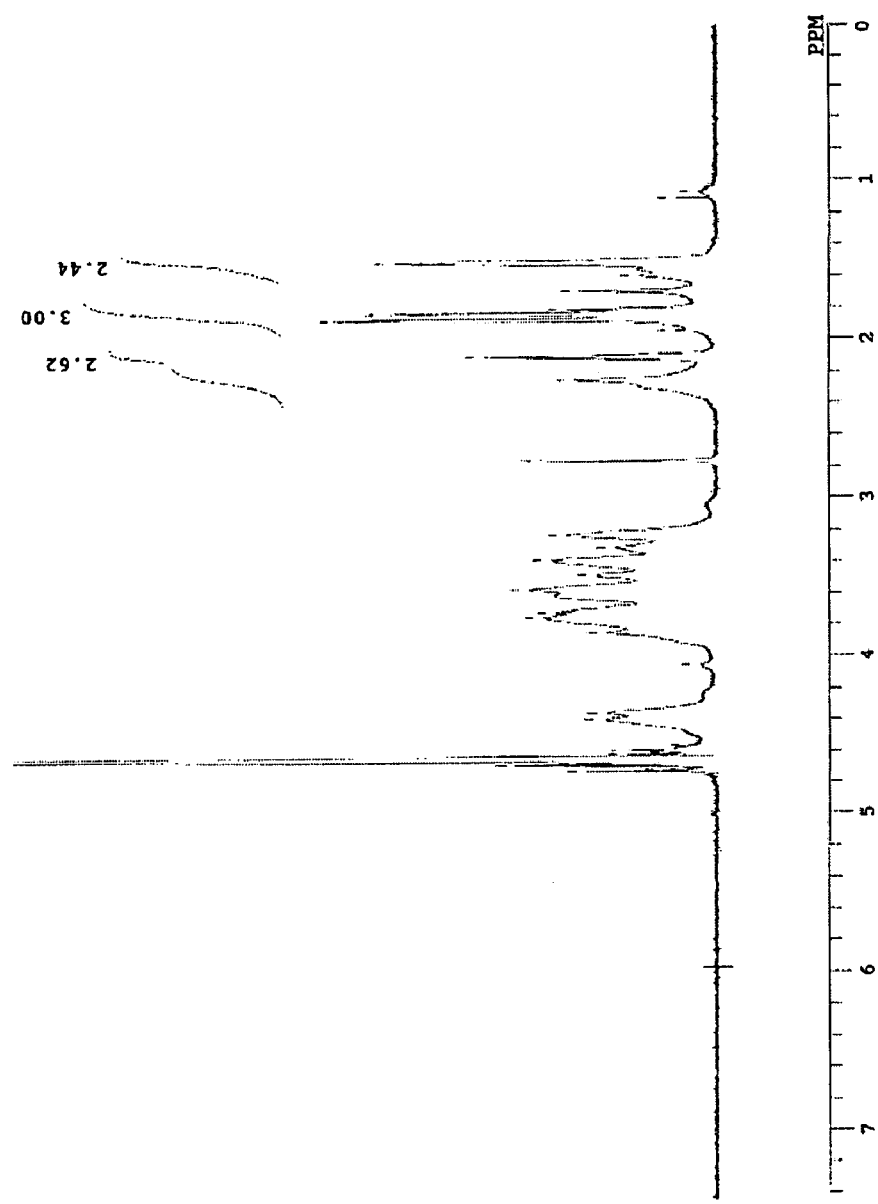
[Fig. 15]

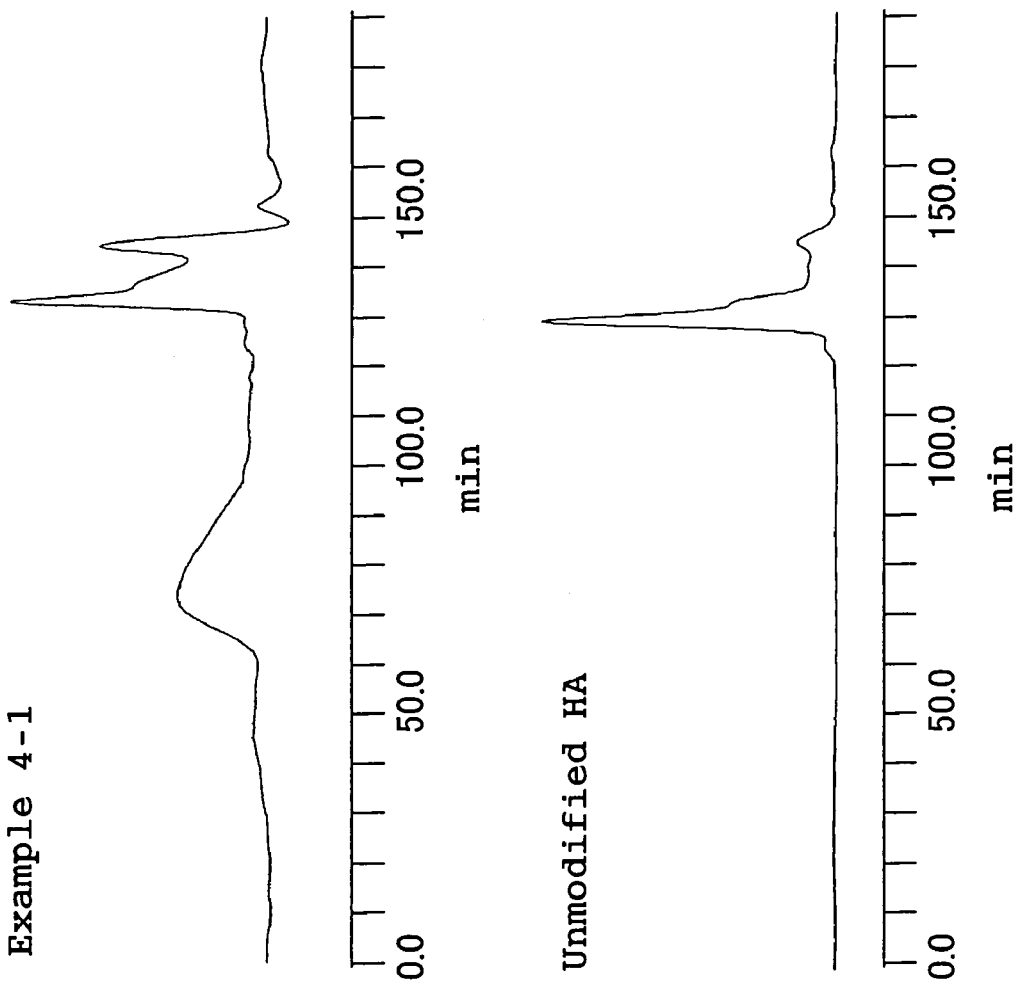
[Fig. 16]

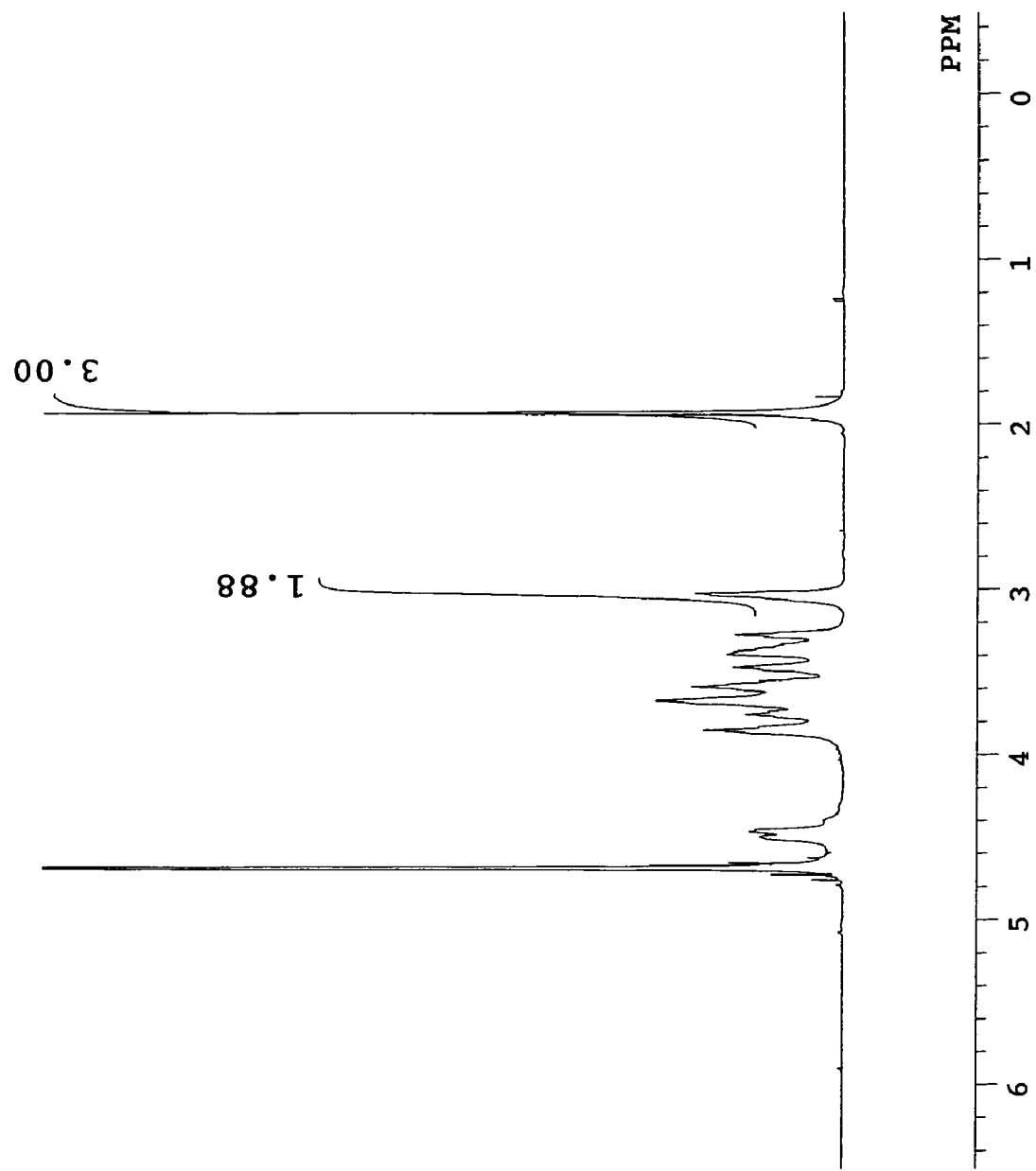
[Fig. 17]

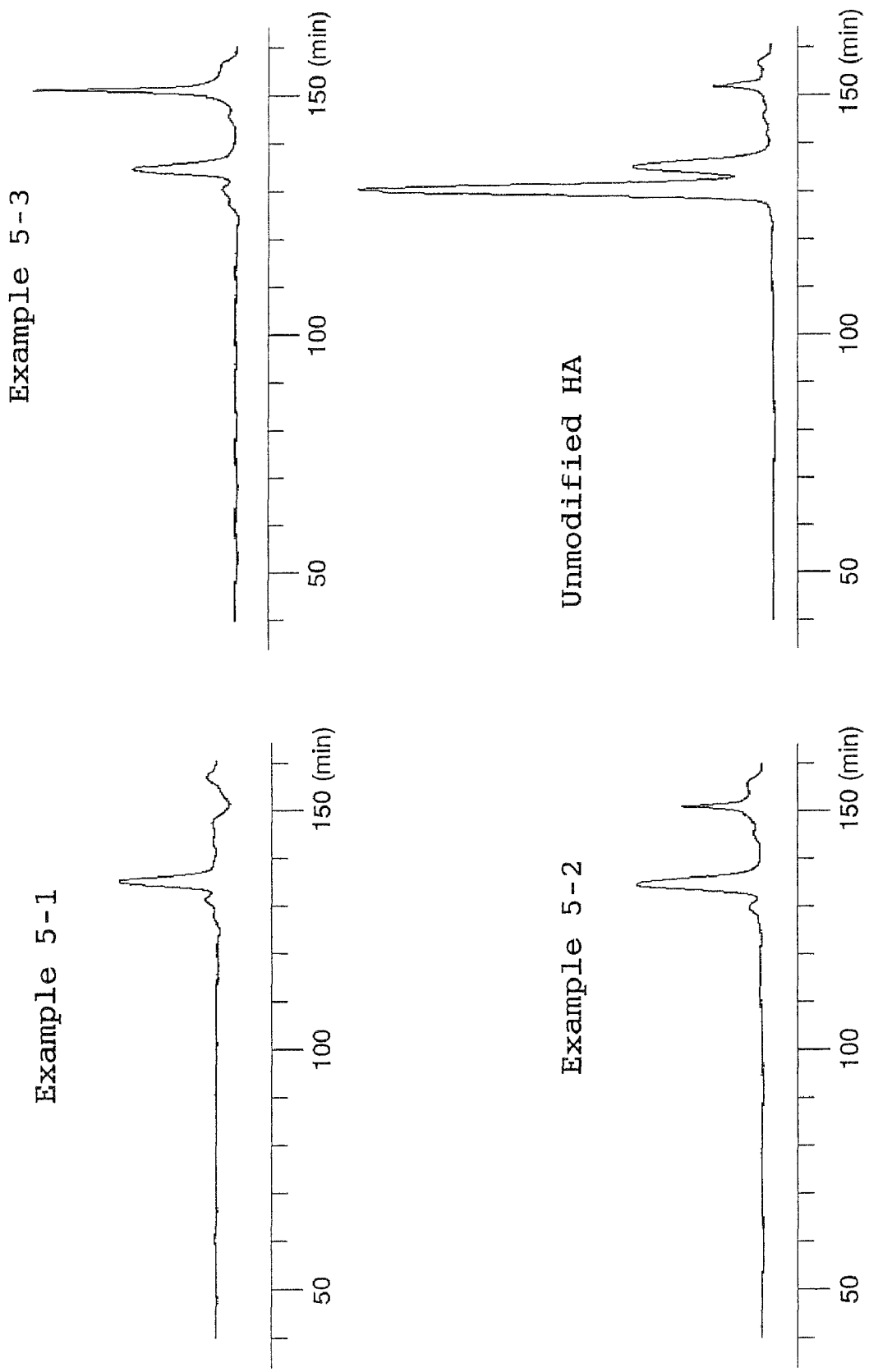
[Fig. 18]

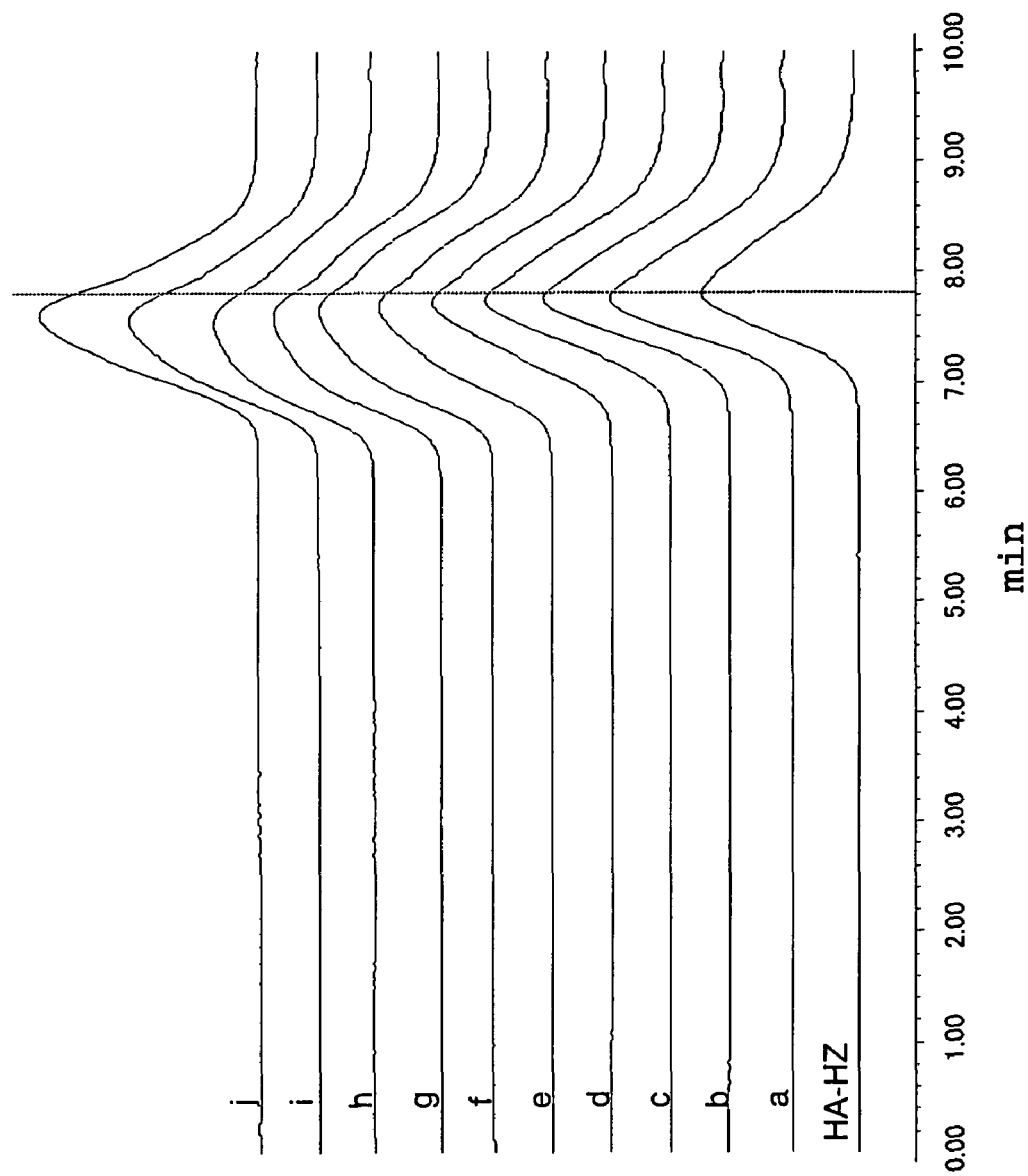
[Fig. 19]

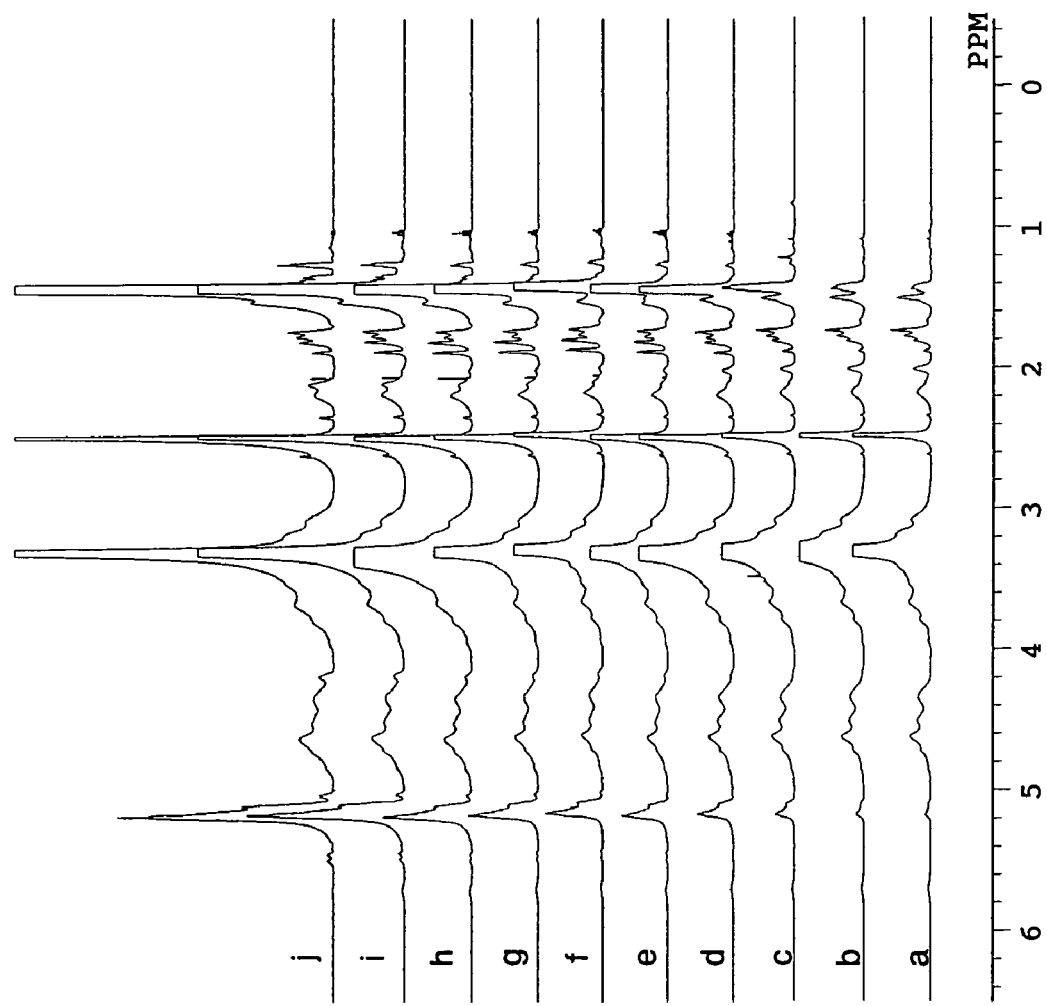
[Fig. 20]

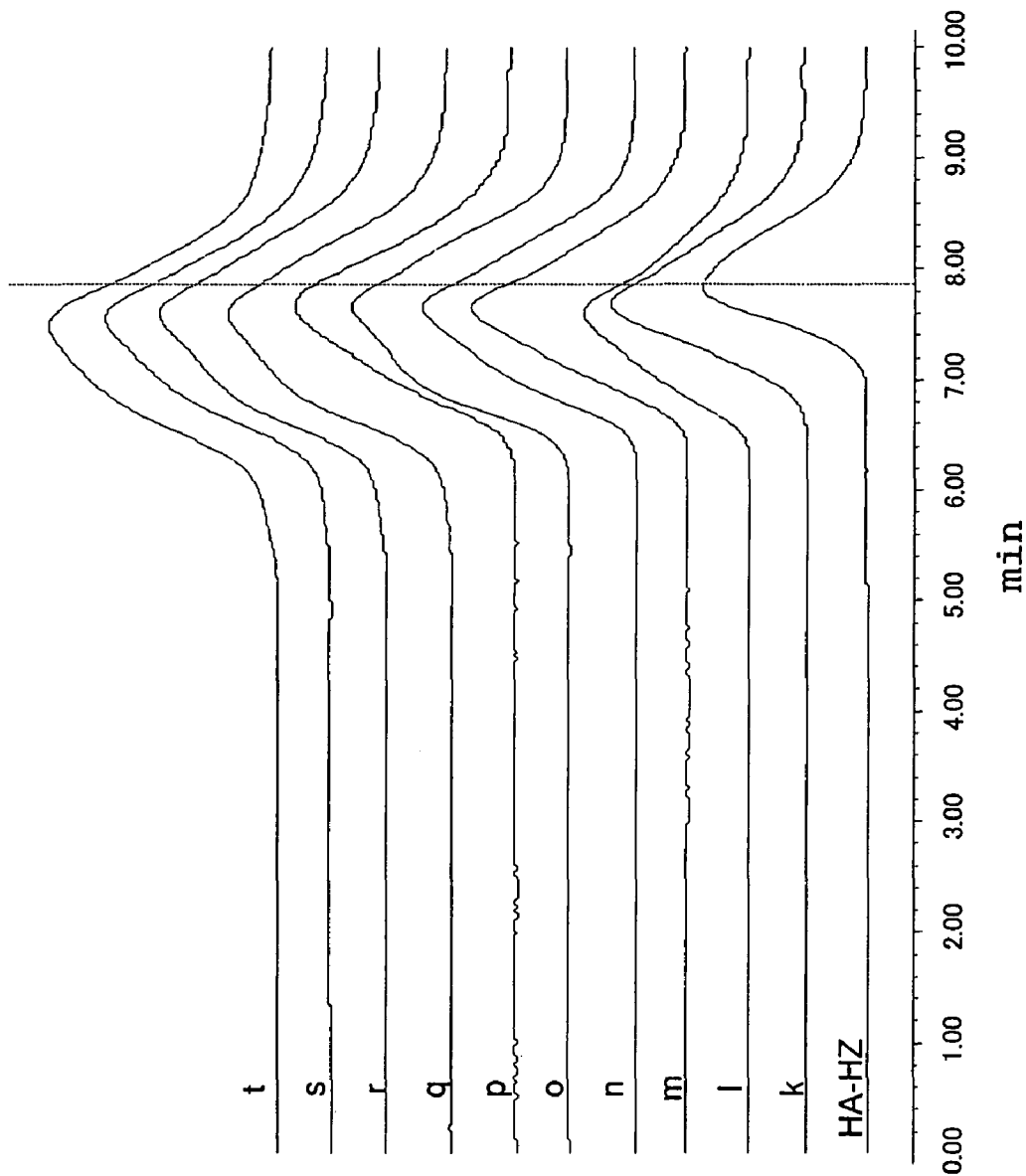
[Fig. 21]

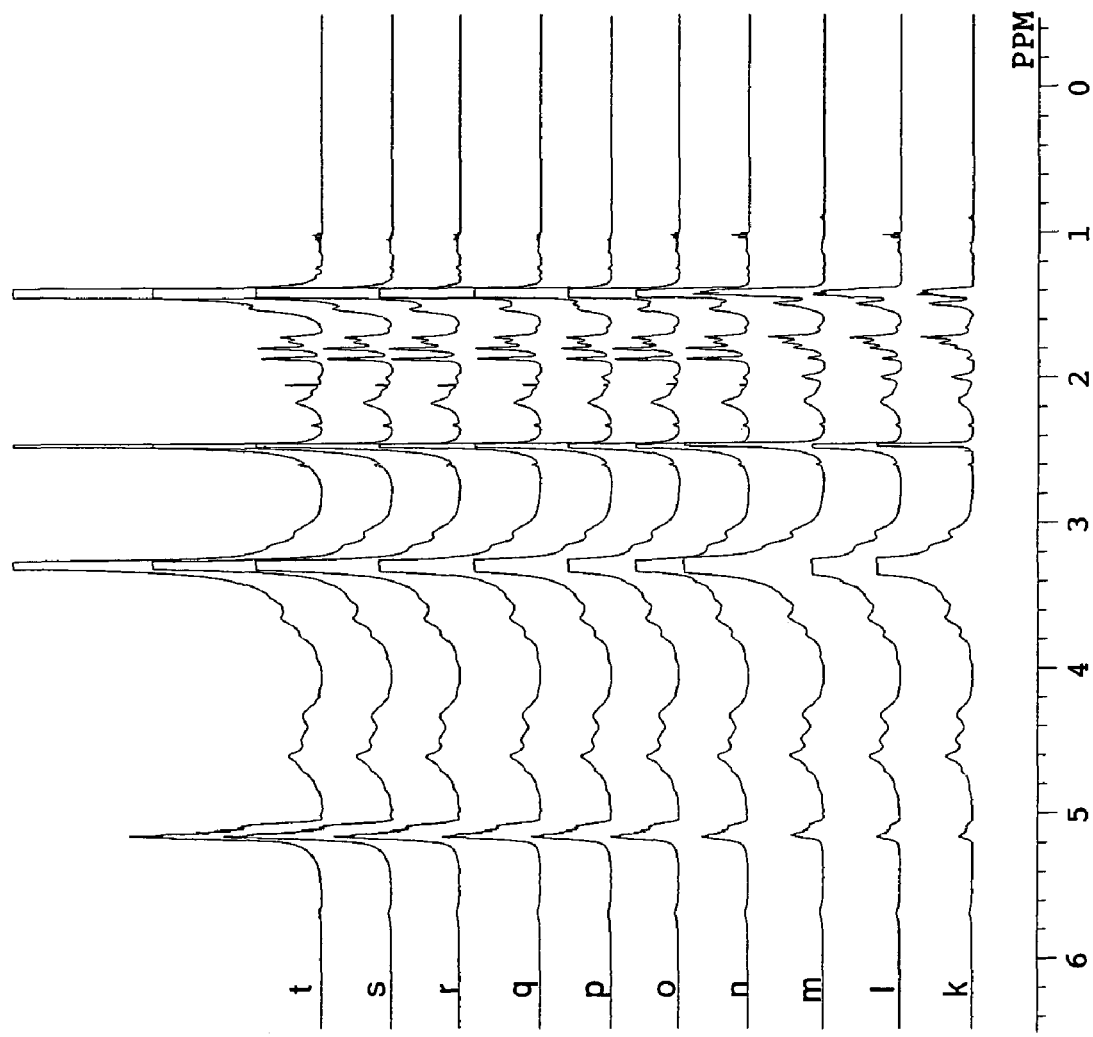
[Fig. 22]

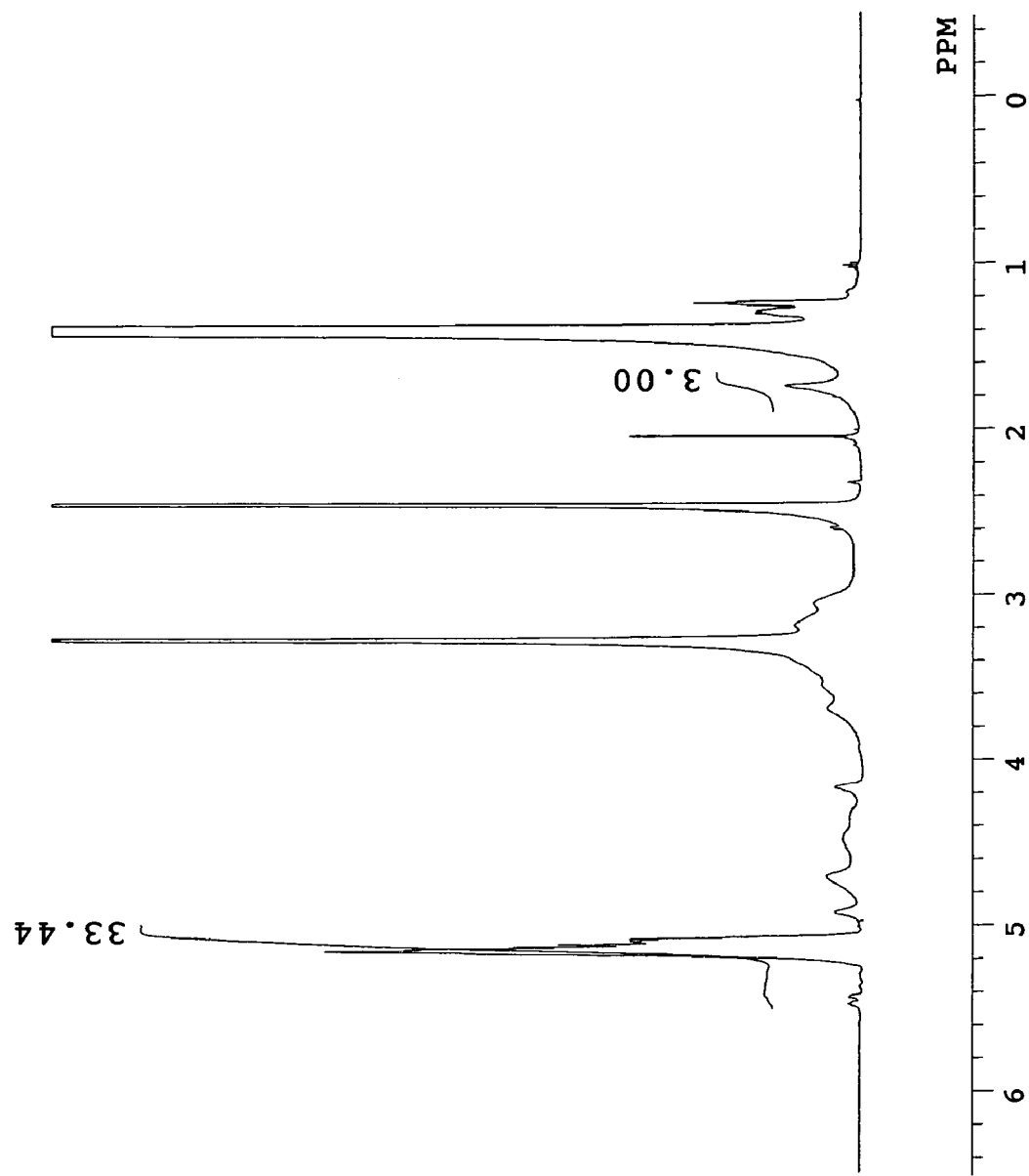
[Fig. 23]

HYALURONIC ACID MODIFICATION PRODUCTS AND DRUG CARRIERS USING THEM

TECHNICAL FIELD

This invention relates to novel hyaluronic acid modification products, and drug carriers using them.

BACKGROUND ART

The utilization of various polymers has been studied in attempts to control the pharmacokinetics of drugs, such as the sustained release, targeting, and prolonged blood residence (stealth effect) of drugs. Of these polymers, biodegradable polymers which are degraded in vivo need not be removed after their introduction in vivo, and thus they are used commonly. Well known biodegradable polymers in practical use include polylactic acid (PLA), polyglycolic acid (PGA), and lactic acid-glycolic acid copolymer (PLGA). These polymers and copolymers have degradation rates controllable by copolymerization ratio, molecular weight, etc., and they are suitable as carriers of hydrophobic drugs. However, when they are formed into injectable fine particles (microspheres or nanospheres), they are prone to agglomerate in aqueous solutions because of their hydrophobicity, thus posing a problem with their dispersibility in administered solutions or in the body after administration. They also present problems with biocompatibility, such as subcutaneous inflammation or tissue blackening.

In arthropathies, such as osteoarthritis and rheumatoid arthritis, synovitis occurs and frequently becomes the cause of pain. Thus, treatment methods are attempted which administer drugs, such as steroidal or nonsteroidal antiinflammatory agents, by the oral route, or directly inject these drugs into the articular cavity. However, clearance in the articular cavity is so rapid (see non-patent document 1 and non-patent document 2) that it is difficult to sustain the effective pharmacodynamic concentration following a single dose, thereby suppressing inflammation for a long term. Thus, there are reports of various attempts at slow release of drugs, such as antiinflammatory agents, by encapsulating them in base materials. For example, reports have been issued on liposome (see non-patent document 3 and non-patent document 4), albumin microspheres (see non-patent document 5), gelatin/chondroitin sulfate microspheres (see non-patent document 6), and lactic acid-glycolic acid copolymer (PLGA) microspheres (see non-patent document 7).

However, such base materials per se are also known to cause pain (crystal-induced pain) (see non-patent document 8). The cause of this pain is unknown, but may be associated with the size or biocompatibility of microspheres. There is also a report of using PLGA nanospheres decreased in size (see non-patent document 9), but the problem of biocompatibility remains unsolved.

Many reports have been presented on drug carriers using biopolymers, such as polysaccharides, collagen, and gelatin. Since they are hydrophilic materials, however, they are not suitable for supporting hydrophobic drugs, and they are inferior to PLA, PGA, PCL and PLGA in terms of the encapsulation efficiency and the duration of slow release. There is a report, for example, of nanospheres using a compound comprising dextran and PLA bonded together (see non-patent document 10 and non-patent document 11). However, PLA is bonded to dextran by ester linkage, so that in vivo hydrolysis of the junction is prompt (1 day or so). Since the compound is a dextran-based material, moreover, it is not suitable for the purposes of targeting and slow release of drugs.

On the other hand, hyaluronic acid (HA) is a biomaterial (polysaccharide) isolated from the vitreous body of the bovine eye by K. Meyer in 1934, and has been known since olden days as a main component of the extracellular matrix. HA is a glucosamidoglycan composed of disaccharide units, each having D-glucuronic acid and N-acetylglucosamine linked by $\beta(1\rightarrow3)$glycosidic linkage. No species difference exists in the chemical or physical structure of HA, and humans have a metabolic system for HA. HA is the safest biomaterial from the aspects of immunity and toxicity. For example, HA is one of the main components of the joint fluid, and shows an analgesic effect in the joint by its viscoelastic effect and antiinflammatory effect. Actually, drugs having HA as an active ingredient have already been marketed and used as drugs for treatment of arthropathy, such as osteoarthritis or rheumatoid arthritis (for example, Suvenyl (trade name): manufactured and sold by CHUGAI PHARMACEUTICAL CO., LTD.).

There are many reports that hydrogels and microspheres comprising HA or its derivatives were applied to sustained release of drugs (see, for example, non-patent document 12, non-patent document 13, patent document 1, patent document 2, patent document 3, and patent document 4). However, their drug release periods are several days or shorter at the longest, and such materials have not reached the level of practical use.

As HA modification products comprising HA and biodegradable polymers in combination, reports have been presented of biomaterials and pharmaceutical sustained release preparations, such as films comprising HA coated with PLGA (see patent document 5), injections comprising PLGA microspheres and HA mixed together (see patent document 6), protein sustained release preparations having PLGA microspheres dispersed in HA hydrogel (see patent document 7), HA coated nanospheres by electrostatic interaction of polycaprolactone (PCL) using a cationic surface active agent, and HA-PLL having HA bonded to a poly-L-lysine side chain (see non-patent document 14).

There are also reports of polysaccharide derivatives comprising polysaccharides grafted to biodegradable polymers, such as PLA, PGA, PCL and PLGA, and fine particles using the polysaccharide derivatives. Among them, examples using HA as the polysaccharide are also disclosed (see patent document 8). Specifically, however, there is only a showing of those comprising PCL ester-linked to HA, and the functions of the resulting HA derivatives are not shown at all.

As described above, HA modification products, which comprise HA and PLA, PGA or PLGA grafted together and which are excellent in all of safety, biodegradability and in vivo stability, are not specifically known. Nor were the methods of their preparation known. Moreover, conventional drug carriers were problematical in the encapsulation efficiency of drugs (especially, lower molecular drugs), sustained release period, dispersibility in aqueous solutions, blood residence period, or safety (occurrence of inflammation in vivo, etc.). Furthermore, drug carriers comprising injectable fine particles with minimal agglomeration between the particles and having excellent biocompatibility were not known.

Patent document 1: International unexamined publication WO98/43664

Patent document 2: International unexamined publication WO00/78356

Patent document 3: Officially Published Patent Gazette 1999-513047

Patent document 4: Officially Published Patent Gazette 2003-525232
Patent document 5: Japanese Patent Application Laid-Open No. 1996-208706
Patent document 6: International unexamined publication WO01/28591
Patent document 7: International unexamined publication WO97/13502
Patent document 8: International unexamined publication WO01/88019
Non-patent document 1: Eur. J. Clin. PHArmacol. 42, 301-305(1992)
Non-patent document 2: Clin. PHArmacol. Ther. 39, 313-317 (1986)
Non-patent document 3: Biochem. J. 158, 473-476(1976)
Non-patent document 4: J. PHArm. PHArmaco. 45, 576-578 (1993)
Non-patent document 5: Int. J. PHArmcol. 39, 129-136 (1987)
Non-patent document 6: Arthritis Rhem. 41, 21. 85-2195 (1998)
Non-patent document 7: Int. J. PHArm. 195, 179-188(2000)
Non-patent document 8: J. Joint Surgery 11, 87-95(1992)
Non-patent document 9: PHArm. Res. 19, 403-410(2002)
Non-patent document 10: J. Biomed. Mater. Res. 50, 557-565 (2000)
Non-patent document 11: PHArm. Res. 20, 1284-1292(2003)
Non-patent document 12: Drug Dev. Ind. PHArm. 25(1), 15-20(1999)
Non-patent document 13: Intern. J. PHArm. 87, 21-29(1992)
Non-patent document 14: Bioconj. Chem. 9, 476-481(1998)

DISCLOSURE OF THE INVENTION

Problems to be Solved by the Invention

An object to be attained by the present invention is to provide a drug carrier which has solved the problems of conventional drug carriers, which can encapsulate a low molecular drug efficiently, which can control a sustained release period for a long term, which can control blood residence, which has high dispersibility in an aqueous solution, and which is not problematical in safety. Another object of the invention is to provide a drug carrier which has similarly solved the problems of conventional drug carriers, which comprises injectable fine particles minimal in agglomeration between the particles, and which has excellent biocompatibility.

Means for Solving the Problems

The inventor diligently proceeded with studies in an attempt to attain the above-mentioned objects. As a result, the inventor found that a hyaluronic acid modification product comprising hyaluronic acid or its derivative, and a polymer bonded together, the polymer being selected from polylactic acid, polyglycolic acid and lactic acid-glycolic acid copolymer, could serve as a drug carrier which encapsulates a low molecular drug efficiently, which can control a sustained release period for a long term, which is well dispersible in an aqueous solution, and which is not problematical in safety. The inventor also found the hyaluronic acid modification product to become a drug carrier forming injectable fine particles minimal in agglomeration between the particles, and having excellent biocompatibility. These findings led the inventor to accomplish the present invention.

According to an aspect of the present invention, there is provided a hyaluronic acid modification product comprising hyaluronic acid or its derivative, and one or more polymers bonded together, the one or more polymers being selected from polylactic acid, polyglycolic acid, and lactic acid-glycolic acid copolymer. In an embodiment of the present invention, the polymer may be grafted as a side chain of hyaluronic acid or its derivative. In another embodiment, most or all of the polymers may be bonded, only at one terminal thereof, to hyaluronic acid or its derivative. In another embodiment of the present invention, the polymer may be bonded to the carboxyl group of hyaluronic acid or its derivative. In still another embodiment, the polymer may be bonded to the carboxyl group of hyaluronic acid or its derivative by an amide bond via a spacer.

Also, the polymer may be bonded to the carboxyl group of hyaluronic acid or its derivative by an amide bond via a spacer.

According to another aspect of the present invention, there is provided
a hyaluronic acid modification product containing in a molecule at least one repeating structure of the formula (I):

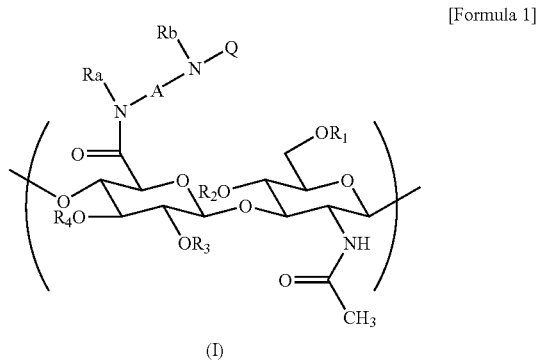

[Formula 1]

(I)

where $R_1$, $R_2$, $R_3$ and $R_4$ are independently selected from a hydrogen atom, a $C_{1-6}$ alkyl group, and a $C_{1-6}$ alkylcarbonyl group, Ra and Rb are independently selected from a hydrogen atom and a $C_{1-6}$ alkyl group, Q is a polymer selected from polylactic acid, polyglycolic acid, and lactic acid-glycolic acid copolymer, and the polymer forms an amide bond with a nitrogen at a terminal carboxyl group thereof, A is a single bond, $-(CH_2)_m-$, $-CH_2-CH_2-(O-CH_2-CH_2)_m-$, or $-NHCO-(CH_2)_n-CONH-$, m is an integer of 1 to 10, and n is an integer of 0 to 10.

The $C_{1-6}$ alkyl group refers to a straight chain or branched chain alkyl group having 1 to 6 carbon atoms and, specifically, includes methyl, ethyl, n-propyl, isopropyl, n-butyl, sec-butyl, isobutyl, t-butyl, n-pentyl, and n-hexyl. The $C_{1-6}$ alkylcarbonyl group refers to an alkylcarbonyl group having the $C_{1-6}$ alkyl group in a molecule and, specifically, includes an acetyl group, a propionyl group, a butyryl group, an isobutyryl group, a valeryl group, an isovaleryl group, and a pivaloyl group. In an embodiment of the present invention, Ra and Rb are each a hydrogen atom, and A is $-(CH_2)_m-$, $-CH_2-CH_2-(O-CH_2-CH_2)_m-$, or $-NHCO-(CH_2)_n-CONH-$.

According to another aspect of the present invention, there is provided a hyaluronic acid modification product in which the aforementioned spacer has two or more amino groups optionally substituted independently, the terminal carboxyl group of the polymer forms an amide bond with one of the amino groups of the spacer, and the carboxyl group of hyaluronic acid or its derivative is bonded to the other amino group of the spacer by an amide bond. Examples of the substituents for the amino groups are, but not limited to, a $C_{1-6}$ alkyl group, a $C_{1-6}$ alkoxyalkyl group, a $C_{1-6}$ haloalkyl group, and a $C_{3-8}$ cycloalkyl group.

According to another aspect of the present invention, there is provided the above-described hyaluronic acid modification product in which the above-mentioned hyaluronic acid derivative contains in a molecule at least one repeating structure of the formula (II):

[Formula 2]

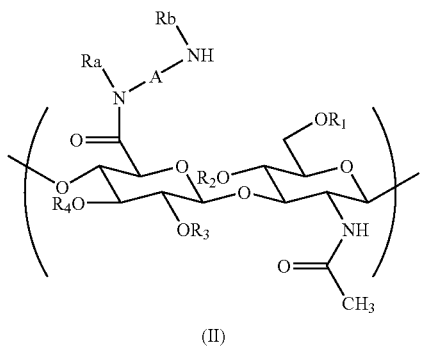

(II)

where $R_1$, $R_2$, $R_3$ and $R_4$, Ra, Rb and A are as defined already.

According to another aspect of the present invention, there is provided the hyaluronic acid derivative in which the hyaluronic acid derivative and/or hyaluronic acid modification product itself have or has resistance to degradation by hyaluronidase, and have or has a mean blood residence time of 18 hours or more, for example, in a mammal.

According to still another aspect of the present invention, there is provided a drug carrier containing the hyaluronic acid modification product. The shape of the drug carrier may be, for example, in the form of fine particles such as microspheres or nanospheres. The drug carrier can have a structure in which the polymer is coated with hyaluronic acid or its derivative in an aqueous solution. The particle size is not limited, but is preferably 200 μm or less, more preferably 100 μm or less, in order to allow the drug carrier to pass through a needle without clogging the needle. In the case of administration to the joint, the drug carrier is apt to cause friction in the joint physically, thereby inducing inflammation anew, so that the particle size is preferably 5 μm or less. In the case of administration by intravenous injection, the particle size is preferably 500 nm or less, more preferably 200 nm or less, so as not to obstruct the peripheral blood vessel. In an embodiment, the drug carrier can have characteristics such as the capacity of targeting HA receptors; resistance to hyaluronidase; and adhesion to the mucosa. The drug carrier can also become a drug carrier with reduced local irritation.

According to still another aspect of the present invention, there is provided a pharmaceutical composition containing the above drug carrier and a drug. In an embodiment, the pharmaceutical composition may further contain one or more polymers selected from polylactic acid, polyglycolic acid, and lactic acid-glycolic acid copolymer and, preferably, the polymer is of the same type as that of the polymer in the hyaluronic acid modification product. In a further embodiment, the drug may be encapsulated in fine particles formed by the hyaluronic acid modification product. The fine particles may be in a form in which a hyaluronic acid portion coats a hydrophobic core formed by a polymer portion of the hyaluronic acid modification product and/or the above polymer. Preferably, in the pharmaceutical composition, the drug is encapsulated in the hydrophobic core portion.

According to still another aspect of the present invention, there is provided a process for producing a hyaluronic acid modification product, comprising the step of reacting a polymer with a hyaluronic acid derivative, the polymer having a carboxyl group at a terminal thereof and being selected from polylactic acid, polyglycolic acid, and lactic acid-glycolic acid copolymer, the hyaluronic acid derivative containing in a molecule at least one repeating structure of the formula (II):

[Formula 3]

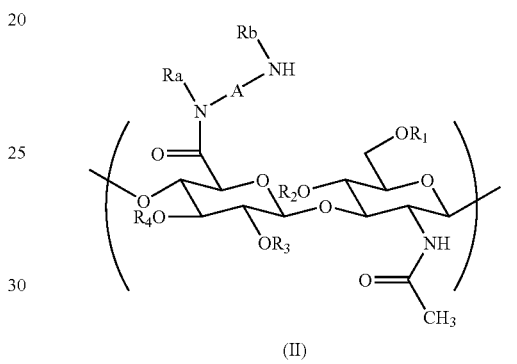

(II)

where $R_1$, $R_2$, $R_3$ and $R_4$, Ra, Rb and A are as defined above. The polymer can be introduced by using a condensing agent, such as N,N'-carbonyldiimidazole (CDI), N,N'-dicyclohexylcarbodiimide (DCC), N-ethoxycarbonyl-2-ethoxy-1,2-dihydroquinoline (EEDQ), 4-(4,6-dimethoxy-1,3,5-triazine)-4-methylmorpholium (DMT-MM), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-tris-pyrrolidino-phosphonium hexafluorophosphate (PyBOP), benzotriazol-1-yl-oxy-tris (dimethylamino)phosphonium hexafluorophosphate (BOP), 1-ethyl-3-(3-dimethylaminopropyl)carbodiimide (EDC), or N-hydroxysuccinimide (NHS), singly or in a suitable combination of any of them. Alternatively, the polymer can be introduced after converting the terminal carboxyl group of the polymer into a highly reactive ester or amide. Also, the polymer may form fine particles in an aqueous solution.

According to still another aspect of the present invention, there is also provided a process for producing the drug carrier by an emulsion solvent evaporation method, a solvent diffusion method, or a dialysis method using the hyaluronic acid modification product.

In an embodiment, the process for producing the drug carrier of the present invention may be performed using the emulsion solvent evaporation method, and may include, for example, the steps of:

a) dissolving one or more polymers, selected from polylactic acid, polyglycolic acid, and lactic acid-glycolic acid copolymer, in an organic phase containing one or more organic solvents and immiscible with water;

b) dissolving or dispersing the hyaluronic acid modification product in an aqueous phase;

c) mixing a polymer solution obtained in the step a and a hyaluronic acid modification product solution or dispersion obtained in the step b to form an emulsion; and d) solvent-evaporating the emulsion obtained in the step c to form drug carrier fine particles, or may include the steps of:

a) dissolving one or more polymers, selected from polylactic acid, polyglycolic acid, and lactic acid-glycolic acid copolymer, in an organic phase containing one or more organic solvents and immiscible with water;

b) mixing a polymer solution obtained in the step a with an aqueous phase to form an emulsion;

c) solvent-evaporating the emulsion obtained in the step b to form polymer fine particles;

d) dissolving or dispersing the hyaluronic acid modification product in another aqueous phase; and e) mixing the polymer fine particles obtained in the step c and a hyaluronic acid modification product solution or dispersion obtained in the step d to form drug carrier fine particles.

In a further embodiment, the process for producing the drug carrier of the present invention may be performed using the solvent diffusion method, and may include, for example, the steps of:

a) dissolving one or more polymers, selected from polylactic acid, polyglycolic acid, and lactic acid-glycolic acid copolymer, in an organic phase containing one or more organic solvents and miscible with water (but containing no water);

b) dissolving or dispersing the hyaluronic acid modification product in an aqueous phase; and c) adding dropwise a polymer solution obtained in the step a to a hyaluronic acid modification product solution or dispersion obtained in the step b to form drug carrier fine particles, or may include the steps of:

a) dissolving one or more polymers, selected from polylactic acid, polyglycolic acid, and lactic acid-glycolic acid copolymer, and the hyaluronic acid modification product in an organic phase containing one or more organic solvents and miscible with water (but containing no water); and b) adding dropwise a polymer-hyaluronic acid modification product solution obtained in the step a to an aqueous phase to form drug carrier fine particles.

In a further embodiment, the process for producing the drug carrier of the present invention by the solvent diffusion method may include the steps of:

a) dissolving the polymer in an organic phase containing one or more organic solvents and miscible with water (but containing no water);

b) adding dropwise a polymer solution obtained in the step a to an aqueous phase to form polymer fine particles;

c) dissolving or dispersing the hyaluronic acid modification product in another aqueous phase; and d) mixing the polymer fine particles obtained in the step b and a hyaluronic acid modification product solution or dispersion obtained in the step c to form drug carrier fine particles.

In a further embodiment, the process for producing the drug carrier of the present invention may be performed using the dialysis method, and may include, for example, the steps of:

a) dissolving the polymer and the hyaluronic acid modification product in an organic phase containing one or more organic solvents and miscible with water (but containing no water); and b) dialyzing a polymer-hyaluronic acid modification product solution, obtained in the step a, against an aqueous phase to form fine particles, or may include the steps of:

a) dissolving the polymer in an organic phase containing one or more organic solvents and miscible with water (but containing no water);

b) dialyzing a polymer solution, obtained in the step a, against an aqueous phase to form polymer fine particles;

c) dissolving or dispersing the hyaluronic acid modification product in another aqueous phase; and d) mixing the polymer fine particles obtained in the step b with a hyaluronic acid modification product solution or dispersion obtained in the step c to form drug carrier fine particles.

In a different aspect of the present invention, there is also provided A process for producing a pharmaceutical composition which includes the above process for producing the drug carrier.

According to a further different aspect of the present invention, there is also provided A process for preparing a hyaluronic acid modification product aqueous solution or dispersion, including the steps of:

a) dissolving the hyaluronic acid modification product in an organic phase containing one or more organic solvents (but containing no water); and b) substituting the solvent of a hyaluronic acid modification product solution, obtained in the step a, by water with the use of the solvent diffusion method or the dialysis method. In an embodiment, the solvent diffusion method can be used in the step b of the preparation method. For example, the preparation method may include the steps of:

a) dissolving the hyaluronic acid modification product in an organic phase containing one or more organic solvents (but containing no water); and b) adding dropwise a hyaluronic acid modification product solution, obtained in the step a, to an aqueous phase to substitute the solvent by water.

In another embodiment, the dialysis method can be used in the step b of the preparation method. For example, the preparation method may include the steps of:

a) dissolving the hyaluronic acid modification product in an organic phase containing one or more organic solvents (but containing no water); and b) dialyzing a hyaluronic acid modification product solution, obtained in the step a, against an aqueous phase to substitute the solvent by water.

According to a further different aspect of the present invention, there is also provided A process for producing a pharmaceutical composition which includes the above process for preparing the hyaluronic acid modification product aqueous solution or dispersion.

According to still another aspect of the present invention, there is provided a hyaluronic acid modification product containing in a molecule at least one repeating structure of the formula (III):

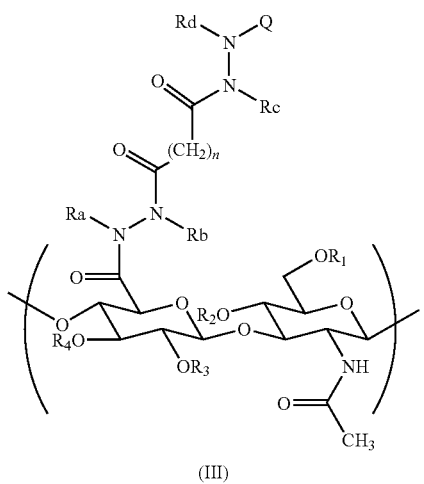

(III)

where $R_1$, $R_2$, $R_3$ and $R_4$ are independently selected from a hydrogen atom, a $C_{1-6}$ alkyl group, and a $C_{1-6}$ alkylcarbonyl group, Ra, Rb, Rc and Rd are independently selected from a hydrogen atom and a $C_{1-6}$ alkyl group, Q is a polymer selected from polylactic acid, polyglycolic acid, polycaprolactone, and a copolymer thereof, and the polymer is bonded to a nitrogen atom at a terminal carboxyl group of the polymer, and n is an integer of 0 to 6.

According to still another aspect of the present invention, there is provided a process for producing a hyaluronic acid modification product, comprising the step of reacting a polymer with a hyaluronic acid derivative, the polymer having a carboxyl group at a terminal thereof and being selected from polylactic acid, polyglycolic acid, polycaprolactone, or a copolymer thereof, and the hyaluronic acid derivative containing in a molecule at least one repeating structure of the formula (IV):

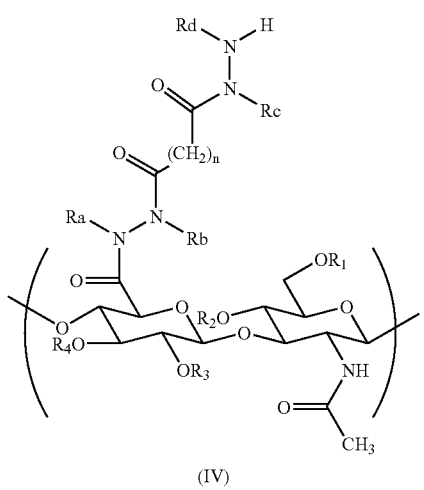

(IV)

where $R_1$, $R_2$, $R_3$, $R_4$, Ra, Rb, Rc, Rd and n are as defined already.

Hereinbelow, the present invention will be described further specifically.

The hyaluronic acid modification product of the present invention comprises hyaluronic acid (HA) or its derivative bonded to one or more polymers selected from polylactic acid (PLA), polyglycolic acid (PGA), and lactic acid-glycolic acid copolymer (PLGA).

In the present invention, hyaluronic acid (HA) or its derivative, and the polymer selected from polylactic acid (PLA), polyglycolic acid (PGA), and lactic acid-glycolic acid copolymer (PLGA) are not bonded together by a physical interaction, such as an electrostatic interaction, but are chemically covalent-bonded. Thus, even upon an environmental change, such as a salt concentration change or a pH change, after administration, the above polymer is not detached from HA or its derivative. When HA or its derivative and the polymer are bonded, they may be bonded via a spacer portion in order to help control bonding. Alternatively, the HA derivative may contain the spacer portion for bonding to the polymer. For example, the spacer portion having a hydrazide group or an amino group can be introduced, for example, by reacting a compound having a plurality of amino groups (dihydrazide compound, diamine compound, hydrazine compound, or the like) with the carboxyl group of the glucuronic acid portion in hyaluronic acid. In a particular embodiment, a diamine compound represented by the formula $H_2N$—$(CH_2)_n$—$NH_2$ (where n is an integer of 0 to 10) or the formula $H_2N$—$CH_2$—$CH_2$—$(O$—$CH_2$—$CH_2)_n$—$NH_2$ (where n is an integer of 0 to 10), a dihydrazide compound represented by the formula $H_2NNHCO$—$(CH_2)_n$—$CONHNH_2$ (where n is an integer of 0 to 10), or a hydrazine compound represented by the formula $NH(R_{10})$—$NH(R_{11})$ (where $R_{10}$ and $R_{11}$ are independently a hydrogen atom or a $C_{1-6}$ alkyl group) can be introduced as the spacer portion.

The use of the method, in which the polymer is introduced after introduction of the spacer portion into the HA derivative, makes it possible to control, independently, the modification rate of the carboxylic acid by the spacer and the modification rate of the spacer by the polymer.

The site where the polymer is bonded to HA or its derivative may be the terminal of HA or its derivative, or may be such that the polymer is introduced as a side chain of HA or its derivative. HA is a very bulky molecule in an aqueous solution. Generally, therefore, when biodegradable fine particles are to be produced using HA or its derivative having the polymer bonded to the terminal thereof, the thickness of the HA layer is large. If HA or its derivative having the polymer grafted thereto as a side chain is used, HA or its derivative is coated in a loop form onto the surfaces of biodegradable fine particles, the thickness of the HA layer can be rendered small. It is preferred for the polymer to be grated to the side chain of HA or its derivative.

The location of introduction of the polymer or the spacer portion into HA or its derivative to be modified is, for example, the hydroxyl group and the carboxyl group in the HA molecule. For introduction into the hydroxyl group, the hydroxyl group is reacted with an activated carboxyl group or the like to form a carboxylic acid ester, whereby the introduction can be achieved. Alternatively, the hydroxyl group is reacted with an isocyanate group or the like to form a carbamic acid ester, whereby the introduction can be achieved.

For introduction into the carboxyl group, an amide group, a hydrazide group, a diacylhydrazide group, or a carboxylic acid ester is formed, whereby the polymer or the spacer portion can be introduced.

In the HA modification product having the polymer or the spacer portion introduced by formation of a carboxylic acid ester among the above-mentioned methods for introduction of the polymer or the spacer portion, detachment of the polymer by hydrolysis in the administered liquid or in vivo occurs in a relatively short time. Generally, therefore, it is preferred that modification be performed via a carbamic acid ester or an amide group or a hydrazide group whose hydrolysis rate is slow.

More preferably, the polymer is bonded to the carboxyl group of hyaluronic acid or its derivative. Particularly preferably, the polymer is bonded to the carboxyl group of hyaluronic acid or its derivative by an amide bond via an amide group or a hydrazide group.

The method of bonding the polymer to the terminal of HA or its derivative is, for example, a method by which a Schiff base formed by an aldehyde at a reducible terminal of HA or its derivative, and a functional group, such as a hydrazide (HZ) group or an amino (AM) group, introduced into the terminal of the polymer or the spacer portion and reactive with an aldehyde group is treated with a reducing agent such as sodium borohydride ($NaBH_4$).

As the method for chemically grafting the polymer as a side chain of HA or its derivative, there can be employed, for example, a method by which a HA derivative having introduced therein the spacer portion containing a functional group reactive with an active ester, such as a hydrazide (HZ) group or an amino (AM) group, is ion-exchanged to form a tetrabutylammonium (TBA) salt, which is reacted in dimethyl sulfoxide (DMSO) with the polymer having the carboxyl group activated by 1-ethyl-3-(3-dimethylaminopropyl) carbodiimide (EDC)/N-hydroxysuccinimide (NHS). In an embodiment of the present invention, the HA derivative having the spacer introduced therein can contain in a molecule the repeating structure of the formula (II):

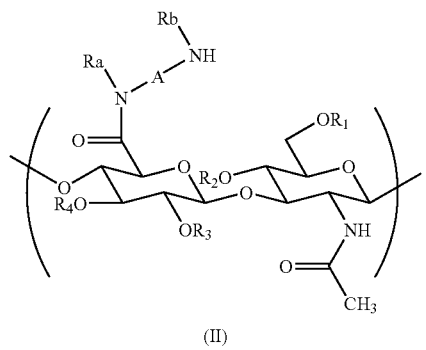

[Formula 6]

(II)

where $R_1$, $R_2$, $R_3$ and $R_4$, Ra, Rb and A are as defined above.

As an alternative introduction method, there can be employed a method which comprises activating the terminal carboxyl group of the polymer with EDC/NHS beforehand, reacting the activated group with diamine or dihydrazide to synthesize the polymer having an amino group or a hydrazide group at the terminal, and directly bonding the polymer to the carboxyl group of HA or its derivative by use of a condensing agent such as EDC/NHS. In an embodiment of the present invention, a compound of the formula (V):

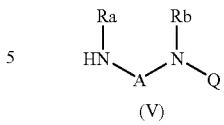

[Formula 7]

(V)

where Ra, Rb, Q and A are as defined above, can be used as the polymer having an amino group or a hydrazide group at the terminal.

In the HA or derivative thereof according to the present invention, most of the polymers are desirably bonded to HA or its derivative only at one terminal thereof. Here, the term "bonded at one terminal" refers to the state of bonding at one of the terminal reactive groups of the polymer. Moreover, the term "most of" is not limited, but specifically, refers to a state where the amount of the polymers bonded to HA or its derivative only at one terminal thereof is 70% w/w or more, preferably 85% w/w or more, particularly preferably 95% w/w or more, based on the amount of all polymers bonded. In any of the cases, the proportion at which both terminals of the polymer are introduced into HA or its derivative is 5 mol % or less, preferably 3 mol % or less, particularly preferably 1 mol % or less, based on the glucuronic acid in HA or its derivative. It goes without saying that the hyaluronic acid modification product of the present invention may be composed only of the hyaluronic acid modification product having the polymer bonded to HA or its derivative only at one terminal thereof.

The method of determining the proportion, at which both terminals of the polymer are introduced into HA or its derivative, to the amount of the polymer bonded to HA or its derivative only at one terminal thereof can be performed by comparing the amount of introduction of the polymer found by proton NMR with the amount of the actual decrease in the hydrazide groups or amino groups in the hydrazide (HZ)- or amino(AM)-incorporated HA derivative before polymer introduction which has been caused by bonding of the polymers. For example, a free hydrazide group-derived peak (2.2 to 2.3 ppm; assay solvent DMSO-$d_6$) obtained by proton NMR of HA-HZ having hydrazide groups introduced by dihydrazide adipate, or a free amino group-derived peak (2.9 to 3.1 ppm; assay solvent DMSO-$d_6$) obtained by proton NMR of HA-AM having amino groups introduced by ethylenediamine should be decreased in proportion to the introduction rate of these polymers. Thus, the ratio between this peak and a HA-derived peak (1.8 to 1.9 ppm; assay solvent DMSO-$d_6$) is actually measured (X). Separately, the ratio of the free hydrazide group or amino group, calculated proportionately from the polymer introduction rate, to the HA-derived peak is calculated (Y), on the assumption that the introduction of the polymers is performed 100% at one terminal. The proportion by which the actually measured ratio is decreased compared with the theoretically calculated ratio is the proportion of the polymers bonded at both terminals. Let the proportion of the polymers introduced into glucuronic acid be Z %, and the proportion of hydrazide group introduction of HA-HZ or the proportion of amino group introduction of HA-AM be H %. In this case, the proportion of the amount of the polymers, bonded to HA or its derivative only at one terminal, to the amount of all polymers bonded is expressed as 1−(HZ)/Z(1−X/Y), while the proportion of introduction of both terminals into HA or its derivative is expressed as (HZ)×(1−X/Y) based on glucuronic acid.

Hyaluronic acid (HA) or its derivative for use in the present invention may be HA or its pharmaceutically acceptable salt, or a derivative form thereof.

Examples of HA or its pharmaceutically acceptable salt are alkali metal salts such as sodium salt, potassium salt, and lithium salt. A particularly preferred salt is the sodium salt in frequent use as a pharmaceutical. HA or its pharmaceutically acceptable salt can be produced by methods for extracting biological materials such as cockscombs and porcine subcutaneous tissue, or various publicly known methods such as biological fermentation. Alternatively, commercially available substances can be purchased (for example, from DENKI KAGAKU KOGYO K.K., Shiseido Co., Ltd., and SEIKAGAKU CORP.).

Examples of the HA derivative derived from HA or its pharmaceutically acceptable salt are products formed by chemically modifying the carboxyl group of the glucuronic acid. The pharmacokinetics can be controlled depending on the modified state of the carboxyl group of the glucuronic acid.

If the carboxyl group modification rate of the glucuronic acid portion of the HA derivative is low (for example, 10 mol % or less), expectation can be placed on a targeting effect on HA receptors, including CD44 expressed in large amounts at inflammation sites or tumor sites, and on the liver and lymphatic tissues which are the main metabolic system for HA. For example, there can be expected targeting at inflamed synovial cells in patients with osteoarthritis or rheumatism, uptake into cells by receptor-dependent endocytosis, and healing of inflammation by drug release in the cells.

If the carboxyl group modification rate of the glucuronic acid portion of the HA derivative is high, the modification product will be drug carrier fine particles whose bonding to HA receptors is suppressed, and which, thus, have a stealth effect and dwell long in vivo. In this case, a targeting effect on tumor cells taking advantage of an EPR effect can also be expected. Furthermore, if the manner of bonding is designed (for example, through an ester or amide linkage) such that after a certain period of time, the modification of the carboxyl group is broken, and the modifying group is detached from HA, passive targeting at tumor tissues takes place owing to the EPR effect, whereafter the fine particles of the present invention incorporating a drug can be delivered into the tumor cells with high efficiency by active targeting via HA receptors.

The method of modifying the carboxyl group of the glucuronic acid portion of HA or its derivative is not limited. However, an example of the method comprises converting the carboxyl group of HA or its derivative into an active ester by use of a condensing agent, such as N,N'-carbonyldiimidazole (CDI), N,N'-dicyclohexylcarbodiimide (DCC), N-ethoxycarbonyl-2-ethoxy-1,2-dihydroquinoline (EEDQ), 4-(4,6-dimethoxy-1,3,5-triazine)-4-methylmorpholium (DMT-MM), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-tris-pyrrolidino-phosphonium hexafluorophosphate (PyBOP), benzotriazol-1-yl-oxy-tris(dimethylamino)phosphonium hexafluorophosphate (BOP), 1-ethyl-3-(3-dimethylamino-propyl)carbodiimide (EDC), or N-hydroxysuccinimide (NHS), singly or in a suitable combination of any of them, before modification of the polymer, and then reacting the active ester with a HA derivative having bonded thereto a functional group reactive with the active ester, such as a hydrazide group or an amino group, thereby bonding them chemically. Alternatively, it is permissible to modify HA or its derivative with the polymer beforehand, and subjecting the remaining carboxyl group of the resulting hyaluronic acid modification product to a similar reaction to carry out modification.

The molecular weight of HA or its derivative used in the present invention is not limited. However, the size, in an aqueous solution, of the molecule of HA or its derivative itself is very large compared with other molecules (for example, HA with a viscosity average molecular weight of 2,000,000 daltons measures 200 to 300 nm). Thus, it is preferred to use HA or its derivative having a low molecular weight (for example, a viscosity average molecular weight of 300,000 daltons or less, e.g., 5,000 to 100,000 daltons) in order to prepare nanospheres with a small particle size.

The molecular weight of the polymer selected from polylactic acid (PLA), polyglycolic acid (PGA), and lactic acid-glycolic acid copolymer (PLGA) for use in the present invention is not limited. However, it is usually preferred to use the polymer having a viscosity average molecular weight of 100,000 daltons or less, for example, 1,000 to 50,000 daltons, from the aspect of the efficiency of reaction with HA or its derivative. Such polymers can be purchased from Alkermes, BirmingHAM Polymers, Inc., Wako Pure Chemical Industries, Ltd., etc.), or can be produced by the non-catalytic dehydration polycondensation method (Japanese Patent Application Laid-Open No. 1986-28521) or the ring opening polymerization using a catalyst from a cyclic diester compound (Encyclopedic Handbook of Biomaterials and Bioengineering Part A Materials, Vol. 2, MarcelDekker, Inc. (1995)).

In connection with the selection of the polymer for use in the present invention, it is preferred to select the polymer having a slow degradation rate (i.e., drug release rate), such as PLA, in order to minimize drug release in vivo until arrival at the targeted site, for example, in the case of the drug carrier intended for targeting. If sustained release of the drug in vivo is aimed at, the drug release rate can be controlled using such a copolymer in order to achieve the drug release rate suited for the intended purpose.

In the present invention, the hyaluronic acid modification product and its salt, in which HA or its derivative and the polymer selected from PLA, PGA and PLGA have been bonded, are soluble in an organic solvent, such as DMSO, DMAc or DMF, or a solvent mixture of the organic solvent and a solvent (e.g., tetrahydrofuran, methanol or ethanol) miscible in a sufficient proportion with the organic solvent, but minimally dissolve in an organic solvent such as acetonitrile, acetone, methylene chloride or ethyl acetate, regardless of the weight ratio of the introduced polymer (PLA, PGA or PLGA).

When, in the present invention, the hyaluronic acid modification product or its salt, in which HA or its derivative and the polymer selected from PLA, PGA and PLGA have been bonded, is to be dissolved or dispersed unchanged in water, it is preferred to use the hyaluronic acid modification product adjusted such that the weight ratio of the polymer (PLA, PGA or PLGA) introduced by covalent bonding is 50% or lower, preferably 30% or lower.

In the present invention, the hyaluronic acid modification product or its salt, in which HA or its derivative and the polymer selected from PLA, PGA and PLGA have been bonded, is dissolved in an organic solvent, such as DMSO, DMAc or DMF, or in a solvent mixture of the organic solvent and a solvent miscible in a sufficient proportion with the organic solvent, and then the solvent is substituted by water by the dialysis method or the solvent diffusion method, whereby the hyaluronic acid modification product and its salt can be dissolved or dispersed in water, regardless of the weight ratio of the introduced polymer (PLA, PGA or PLGA). At this time, the hyaluronic acid modification product is considered, without restriction, to exist in water in such a state that the hydrophobic polymer portion is spontaneously gathered as the core portion, and the hydrophilic HA or its derivative portion faces the surface.

The hyaluronic acid modification product of the present invention can be used as a drug carrier. In accordance with the customary method, a drug is advisably encapsulated, included, supported and/or dispersed in the hyaluronic acid modification product of the present invention.

The drug used in the present invention is not limited, as long as it is a drug which can be supported on a biodegradable polymer. A low molecular compound, a protein, a peptide, etc. can be used.

Examples of the low molecular compound are anticancer drugs (e.g., alkylating agents, metabolic antagonists, alkaloids, etc.), immunosuppressants, antiinflammatory agents (steroids, non-steroidal antiinflammatory agents, etc.), antirheumatic agents, and antimicrobial agents (β-lactam antibiotics, aminoglycoside antibiotics, macrolide antibiotics, tetracycline antibiotics, new quinolone antibiotics, sulfa drugs, etc.).

Examples of the protein and the peptide are erythropoietin (EPO), granulocyte colony stimulating factor (G-CSF), interferon-α, -β and -γ (INF-α, -β and -γ), thrombopoietin (TPO), ciliary neurotrophic factor (CNTF), tumor necrosis factor (TNF), tumor necrosis factor bonding protein (TNFbp), interleukin 10 (IL-10), FMS-like tyrosine kinase (Flt-3), growth hormone (GH), insulin, insulin-like growth factor-1 (IGF-1), platelet-derived growth factor (PDGF), interleukin-1 receptor antagonist (IL-1ra), brain-derived neurotrophic factor (BDNF), keratinocyte growth factor (KGF), stem cell factor (SCF), megakaryocyte growth differentiation factor (MGDF), osteoprotegerin (OPG), leptin, parathyroid hormone (PTH), basic fibroblast growth factor (b-FGF), bone morphogenetic protein (BMP), atrial natriuretic peptide (ANP), brain natriuretic peptide (BNP), C-type natriuretic peptide (CNP), glucagon-like peptide-1 (GLP-1), antibodies, diabodies, minibodies, and fragmented antibodies.

The most preferred embodiment of the present invention is, for example, the drug carrier formed as fine particles. In the hyaluronic acid modification product of the present invention, HA or its derivative portion is hydrophilic, and the polymer is hydrophobic. In an aqueous solution, therefore, the hyaluronic acid modification product of the present invention has a structure in which the surface of the polymer is coated with HA or its derivative, thereby taking the form of fine particles. In these fine particles, the drug can be encapsulated, included, supported and/or dispersed. This drug carrier has the surfaces of the particles coated with hydrophilic HA or its derivative, so that the agglomeration and friction of the particles in the administered aqueous solution or in the in vivo setting are prevented. Moreover, the drug carrier has HA surface of high biocompatibility. Hence, the direct contact of the polymer in the core portion with biological tissue is avoided to mitigate the problem of inflammation or the like.

The particle size of the drug carrier of the present invention in the form of fine particles is preferably 200 μm or less, more preferably 100 μm or less, in order to permit passage through a needle without its clogging. In the case of intraarticular administration, friction in the joint is apt to occur physically, and this friction induces inflammation anew, so that the particle size is preferably 5 μm or less. In the case of intravenous administration by injection, the particle size is preferably 500 nm or less, more preferably 200 nm or less, so as not to obstruct the peripheral blood vessel.

The fine particles of the present invention are highly biocompatible, and free from inflammatory properties, and the hyaluronic acid itself adheres to the mucosa. Thus, the fine particles can be used for noninvasive administration such as transnasal, transpulmonary or peroral administration by controlling the particle size. The mucosal adhesion can be adjusted by the amount of the carboxylic acid of HA. In this case, a larger amount of the carboxylic acid is preferred, and a lower modification rate by the spacer or polymer is preferred.

The method of preparing the fine particles of the present invention is, for example, the emulsion solvent evaporation method, the solvent diffusion method (J. Contr. Rel. 83, 365-375(2002)), or the dialysis method. Specific examples of the method are a method by which to prepare polymer fine particles, and then chemically bond HA or its derivative to their surfaces for coating of the polymer fine particles; and a method by which to synthesize, beforehand, a hyaluronic acid modification product having the polymer chemically bonded to the terminal or side chain of HA or its derivative, and prepare fine particles by the emulsion solvent evaporation method, the solvent diffusion method, or the dialysis method using the hyaluronic acid modification product. During the formation of the fine particles, the fine particles are spontaneously coated with HA. Alternatively, after the formation of the fine particles, the fine particles are spontaneously coated with HA.

In preparing polymer fine particles, and then chemically bonding HA or its derivative to their surfaces for coating of the polymer fine particles, it is common practice to prepare fine particles comprising the polymer in accordance with the customary method, then convert the carboxyl groups on the surfaces of the particles into active esters by use of a condensing agent, such as 1-ethyl-3-(3-dimethylaminopropyl)carbodiimide (EDC), or N-hydroxysuccinimide (NHS), and react the active esters with HA or its derivative incorporating a spacer containing a functional group reactive with the active ester, such as a hydrazide (HZ) group or an amino (AM) group to form bonds chemically. By this procedure, fine particles comprising the hyaluronic acid modification product of the present invention can be produced.

In a different embodiment of the present invention, fine particles further containing one or more polymers selected from PLA, PGA and PLGA and coated with the hyaluronic acid modification product can be prepared by the emulsion solvent evaporation method. That is, PLA, PGA or PLGA is dissolved in an organic solvent immiscible with water, such as methylene chloride or ethyl acetate, or a solvent mixture of the organic solvent and a solvent miscible in a sufficient proportion with the organic solvent. Separately, the hyaluronic acid modification product of the present invention is dissolved or dispersed in an aqueous phase. After preparation of an emulsion, the emulsion is liquid-dried by the emulsion solvent evaporation method, whereby fine particles coated with the hyaluronic acid modification product of the present invention can be prepared. In this preparation method, the hyaluronic acid modification product of the present invention is, although not limited to, an amphipathic molecule having a hydrophobic portion and a hydrophilic portion in a molecule, and is thus considered to show a surface active action.

In a different embodiment of the present invention, fine particles further containing one or more polymers selected from PLA, PGA and PLGA and coated with the hyaluronic acid modification product can be prepared by the solvent diffusion method. That is, PLA, PGA or PLGA is dissolved in an organic solvent miscible with water, such as acetone or acetonitrile, or a solvent mixture of the organic solvent and an organic solvent miscible in a sufficient proportion with the organic solvent, such as ethanol or methanol. When the resulting solution is mixed with an aqueous phase, the organic solvent diffuses to form fine particles. The hyaluronic acid modification product of the present invention can be used as dissolved or dispersed in the aqueous phase. When the fine particles are formed, the fine particles can be coated with the hyaluronic acid modification product of the present invention.

When the organic solvent, such as DMSO, DMAc or DMF, or the solvent mixture of the organic solvent and a solvent miscible in a sufficient proportion with the organic solvent, is used when using the solvent diffusion method or the dialysis method, the hyaluronic acid modification product of the present invention can be used dissolved in the organic phase. The hyaluronic acid modification product of the present invention, or a mixture of the hyaluronic acid modification product and the polymer selected from PLA, PGA and PLGA, which has been dissolved in the organic phase, is dialyzed against, or added dropwise to, the aqueous phase, whereby the solvent is substituted by water. At this time, the hydrophobic polymers gather to form fine particles, and the hydrophilic HA portions gather on the surfaces of the fine particles. As a result, the fine particles can be coated with the hyaluronic acid modification product of the present invention. When the organic solvent, such as DMSO, DMAc or DMF, or the solvent mixture of the organic solvent and a solvent miscible in a sufficient proportion with the organic solvent, is used when using the solvent diffusion method or the dialysis method, the hyaluronic acid modification product of the present invention can be used dissolved or dispersed in the aqueous phase. During formation of the fine particles, the fine particles can be coated with the hyaluronic acid modification product of the present invention.

The surfaces of the fine particles comprising PLA, PGA or PLGA are hydrophobic, regardless of the method of preparing the fine particles. When these fine particles are mixed with an aqueous solution containing the hyaluronic acid modification product of the present invention dissolved or dispersed therein, therefore, adsorption to the surfaces of the fine particles by a hydrophobic interaction takes place, whereby the fine particles coated with the hydrophilic hyaluronic acid modification product of the present invention can be prepared.

The aqueous phase used in the preparation of the fine particles in the present invention may comprise only water, or a solvent mixture of water and a solvent miscible in a sufficient proportion with water. If desired, the aqueous phase may contain additives normally used in the technical field concerned, for example, a surface active agent, a pH regulator, and a buffer, and may have its pH or salt concentration adjusted as appropriate.

Fine particles can be formed using only the hyaluronic acid modification product of the present invention. However, there can be formed fine particles containing the hyaluronic acid modification product of the present invention together with additives normally used in the technical field concerned, for example, a surface active agent, a pH regulator, and an antioxidant. In an embodiment of the present invention, the fine particles containing the hyaluronic acid modification product of the present invention can contain in its core portion the HA-unbonded polymer selected from PLA, PGA and PLGA. By adding the above additives and the polymer, the particle size and the drug supporting capacity of the fine particles can be adjusted.

If the fine particles intended, particularly, for targeting at HA receptors including CD44 are to be prepared among the fine particles coated with the hyaluronic acid modification product of the present invention, their particle size is preferably 5 µm or less, for example, 1 nm to 5 µm, and the dialysis method, the solvent diffusion method, or the emulsion solvent evaporation method can be used as the process for preparation. The hyaluronic acid modification product used at this time, preferably, has the modification rate of the carboxylic acid of the glucuronic acid portion of HA being 10 mol % or less, for example, 0.1 to 10%, so that the bonding to HA receptors will not be suppressed.

If the fine particles intended, particularly, for prolonged blood residence, and accumulation in tumor tissue or inflammatory tissue are to be prepared among the fine particles coated with the hyaluronic acid modification product of the present invention, their particle size is preferably 200 nm or less, for example, 1 nm to 200 nm, and the dialysis method, the solvent diffusion method, or the emulsion solvent evaporation method can be used as the process for preparation. The hyaluronic acid modification product used at this time, preferably, has the carboxylic acid of the glucuronic acid portion of HA modified at a modification rate of 30 to 100%, preferably 50 to 90%, so that the bonding to HA receptors will be suppressed.

If the fine particles intended for diminished local irritation are to be prepared among the fine particles coated with the hyaluronic acid modification product of the present invention, their particle size is preferably 200 µm or less, for example, 1 nm to 200 µm, and the dialysis method, the solvent diffusion method, or the emulsion solvent evaporation method can be used as the process for their preparation.

If the fine particles having mucosal adhesion and intended for application to noninvasive administration are to be prepared among the fine particles coated with the hyaluronic acid modification product of the present invention, their particle size is preferably 200 µm or less, for example, 1 nm to 200 µm, and the dialysis method, the solvent diffusion method, or the emulsion solvent evaporation method can be used as the process for their preparation. The hyaluronic acid modification product used, preferably, has a low modification rate of the carboxylic acid of HA so as to have mucosal adhesiveness.

A method for encapsulating a drug in a polymer is usually used as the method of encapsulation of a drug in these fine particles. For example, it is recommendable to render a drug coexistent when dissolving the polymer in an organic solvent such as DMSO at the time of fine particle preparation, and prepare fine particles unchanged. If the water solubility of the drug is high, for example, the efficiency of encapsulation can be increased by converting the drug into a salt with low solubility in water, or by using the W/O/W emulsion method.

If the fine particles prepared are minimally redispersed after lyophilization, lyophilization can be performed in the copresence of a dispersing agent such as trehalose or mannitol.

In harmony with the applications of the hyaluronic acid modification product of the present invention, the blood residence time of the hyaluronic acid modification product of the present invention may be extended compared with the blood residence time of HA itself. To obtain the hyaluronic acid modification product of the present invention with an extended blood residence time, a hyaluronic acid derivative with an extended blood residence time can be used as the starting material. The blood residence time can be compared, as appropriate, using a publicly known representative parameter, such as a mean blood residence time (may hereinafter be referred to as MRT), a blood half-life (may hereinafter be referred to as t½), or blood clearance (may hereinafter be referred to as Cl). If a stealth effect is expected of the hyaluronic acid modification product of the present invention, the blood residence time in mammals including humans is such that from the practical point of view, the mean blood residence time (MRT) is preferably 18 hours or more, more preferably 30 hours or more.

According to a different aspect, the hyaluronic acid modification product of the present invention may be one having resistance to degradation by hyaluronidase as compared with HA itself, in harmony with its applications. To obtain the hyaluronic acid modification product of the present invention which has resistance to degradation by hyaluronidase as compared with HA itself, a hyaluronic acid derivative having resistance to degradation by hyaluronidase as compared with HA itself can be used as the starting material. The term "having resistance to degradation by hyaluronidase" refers to having the property that the degradation rate is lower than that of HA itself, or degradation does not proceed compared with HA itself, when HA itself, the hyaluronic acid modification product of the present invention, or the hyaluronic acid derivative as the starting material is enzymatically degraded by hyaluronidase. For example, if a disaccharide degradation peak, which is observed with HA itself, is not observed upon hyaluronidase treatment performed for a constant period of time, the property that "degradation does not proceed" (namely, having resistance to degradation by hyaluronidase) can be judged to be possessed. The degradation rate or degradation state of HA can be observed using the customary method such as gel permeation chromatography (may hereinafter be referred to as GPC).

Effects of the Invention

According to the present invention, there is provided a hyaluronic acid modification product having hyaluronic acid or its derivative and one or more polymers bonded together, the polymer being selected from polylactic acid, polyglycolic acid, and lactic acid-glycolic acid copolymer. Using the hyaluronic acid modification product, there is provided a drug carrier which can encapsulate a low molecular drug efficiently, which can control a sustained release period for a long term, which can control blood residence, which has high dispersibility in an aqueous solution, and which is not problematical in safety. The hyaluronic acid modification product of the present invention further provides a drug carrier which comprises injectable fine particles minimal in agglomeration between the particles and controllable in particle size, and which has excellent biocompatibility.

BRIEF DESCRIPTION OF THE DRAWINGS

FIG. 1 is an example of a photograph, taken with SEM, of microspheres comprising the hyaluronic acid modification product of the present invention.

FIG. 2 is an example of a photograph, taken with a 3D laser microscope, of microspheres comprising the hyaluronic acid modification product of the present invention.

FIG. 3 is an example of a photograph, taken with SEM, of PLGA microspheres as a control.

FIG. 4 is an example of a photograph, taken with a 3D laser microscope, of PLGA microspheres as a control.

FIG. 5 is an example of the results of measurement, by GPC, of the hyaluronic acid modification product of the present invention.

FIG. 6 is an example of the results of measurement, by NMR, of the hyaluronic acid modification product of the present invention.

FIG. 7 is an example of a photograph of a dispersed solution of nanospheres (HA(25 kdaltons)-PLA nanospheres) comprising the hyaluronic acid modification product of the present invention after the dispersed solution was stored for 1 month at 4° C.

FIG. 8 is an example of a photograph of a dispersed solution of nanospheres (HA(190 kdaltons)-PLA nanospheres) comprising the hyaluronic acid modification product of the present invention after the dispersed solution was stored for 1 month at 4° C.

FIG. 9 is an example of a photograph of a dispersed solution of PLA nanospheres (control) after the dispersed solution was stored for 1 month at 4° C.

FIG. 10 is an example of an SEM photograph of the dispersed solution of nanospheres (HA(25 kdaltons)-PLA nanospheres) comprising the hyaluronic acid modification product of the present invention after the dispersed solution was stored for 1 month at 4° C.

FIG. 11 is an example of an SEM photograph of the dispersed solution of nanospheres (HA(190 kdaltons)-PLA nanospheres) comprising the hyaluronic acid modification product of the present invention after the dispersed solution was stored for 1 month at 4° C.

FIG. 12 is an example of an SEM photograph of the dispersed solution of PLA nanospheres (control) after the dispersed solution was stored for 1 month at 4° C.

FIG. 13 is an example of the proton NMR spectrum, in an aqueous solution, of a dispersed solution of nanospheres comprising the hyaluronic acid modification product of the present invention.

FIG. 14 is an example of the proton NMR spectrum, in an aqueous solution, of the dispersed solution of nanospheres comprising the hyaluronic acid modification product of the present invention.

FIG. 15 is an example of the NMR spectrum of HA-HZ obtained in Example 4-1.

FIG. 16 is an example of the results of a degradation test of HA-HZ obtained in Example 4-1 against hyaluronidase SD, and the results obtained when unmodified HA was treated with hyaluronidase SD under the same conditions.

FIG. 17 is an example of the proton NMR spectrum of HA-Am obtained in Example 5-1.

FIG. 18 is an example of the results of degradation tests of HA-AM's obtained in Examples 5-1 to 5-3 against hyaluronidase SD, and the results obtained when unmodified HA was treated with hyaluronidase SD under the same conditions.

FIG. 19 is an example of the GPC chromatogram of HA-HZ-PLA obtained in Example 6-2.

FIG. 20 is an example of the proton NMR spectrum of HA-HZ-PLA obtained in Example 6-2.

FIG. 21 is the GPC chromatogram of HA-HZ-PLA obtained in Example 6-3.

FIG. 22 is an example of the proton NMR spectrum of HA-HZ-PLA obtained in Example 6-3.

FIG. 23 is an example of the proton NMR spectrum of HA-AM-PLA obtained in Example 7-7.

EXAMPLES

Preferred examples of the present invention will now be described in further detail, but the present invention is not limited to these examples. In the following descriptions, products comprising HA and PLA bonded together are collectively referred to as HA-PLA, regardless of the manner of bonding. A product containing a dihydrazide compound as a spacer molecule may be referred to as HA-HZ-PLA, while a product containing a diamine compound as a spacer molecule may be referred to as HA-AM-PLA.

The determination of amino groups by trinitrobenzenesulfonic acid (TNBS) complied with the method described on page 37 of "Center of Academic Publications Japan, Biological Chemistry Experimental Methods 12, Chemical Modification of Proteins <Volume One>, 1st edition" (namely, the TNBS method). However, a TNBS solution was adjusted to 0.5M, and the absorbance at 500 nm was measured to determine hydrazide groups.

NMR measurement used JNM-ECA500 (500 MHz spectrometer) as an NMR spectrometer, and was performed under the following conditions (parameters):

NMR Conditions
Data points (X point): 16384
Spectral width (X sweep): 15 ppm
Acquisition time (X acq time): 1.749 s
Pulse delay (Relaxation delay): 30 s
Transients (Scans): 64
Temperature: Room temperature

Example 1

Preparation of Hyaluronic Acid-Coated PLGA Microspheres

Example 1-1

Synthesis of Hyaluronic Acid having Hydrazide Groups (HZ) Introduced Therein (HA-HZ)

Hyaluronic acid (HA) having a molecular weight of $2.5 \times 10^4$ daltons (DENKI KAGAKU KOGYO K.K.; 100 mg) was dissolved in distilled water at a concentration of 1%, and the pH of the solution was adjusted to 4.7 to 4.8 with 5N hydrochloric acid. 1-Ethyl-3-(3-dimethylaminopropyl)carbodiimide (EDC) (Sigma-Aldrich Corp.) and dihydrazide adipate (ADH) (Sigma-Aldrich Corp.) were added to the solution such that the amount of EDC added was at a molar ratio of 5:1, and the amount of ADH added was at a molar ratio of 40:1, to glucuronic acids (carboxyl groups) contained in the Hyaluronic acid used. The mixture was reacted for 2 hours at room temperature, with its pH being kept at 4.7 to 4.8 with 5N hydrochloric acid. The reaction mixture was dialyzed against a 100 mM aqueous solution of sodium chloride and a 25% aqueous solution of ethanol (Spectra/Por 7, molecular cutoff (MWCO): 12 k-14 k daltons), and lyophilized to obtain 88 mg of the captioned hyaluronic acid derivative having hydrazide groups (HZ) introduced therein (HA-HZ).

When the HZ introduction rate of the resulting HA-HZ was determined by the proton NMR method (measuring solvent: $D_2O$), it was found that 65% of the carboxylic acids of HA were converted into HZ (HA:N-acetyl group, 2.1 ppm, HZ: methylene groups of adipic acid portion, 1.7 ppm, 2.4 ppm). Determination by the TNBS method showed the HZ introduction rate to be 34.9%.

Example 1-2

Preparation of PLGA Microspheres

PLGA7510 (Wako Pure Chemical Industries, Ltd.: molecular weight 10,000 daltons) was dissolved with the addition of 10 mL of methylene chloride (JUNSEI CHEMICAL CO., LTD.) to prepare a 10% (w/v) solution. This solution was mixed with 90 mL of a 1% aqueous solution of polyvinyl alcohol (87-89% hydrolyzed, molecular weight 13,000-26,000) (i.e. PVA aqueous solution) at a mixing ratio of 1:9 (v/v). The mixture was stirred at about 700 rpm by a stirrer to obtain an oil-in-water (O/W) emulsion. The emulsion was put in 900 mL of a 1% PVA aqueous solution, and the mixture was stirred overnight at about 200 rpm, followed by distilling off the solvent, to obtain a suspension of microspheres. The suspension was centrifuged for 10 minutes at 1,000 rpm at 4° C., and the supernatant was removed. The residue was thoroughly washed with water, and lyophilized. The lyophilizate was recovered as microspheres. The measurement of the particle size by SEM image analysis showed that the microspheres with a particle size of the order of 30 to 80 μm were obtained.

Example 1-3

Preparation of Hyaluronic Acid-Coated PLGA Microspheres

The surface carboxylic acids of the PLGA microspheres obtained in Example 1-2 were activated using EDC and Sulfo-NHS (N-hydroxysulfosuccinimide) (Pierce Biotechnology Inc.) (PLGA/EDC/Sulfo-NHS=1/5/5 molar ratio, stirred for 1 hour at room temperature in 100 mM phosphate buffer (pH 5.8)). Then, the system was charged into an aqueous solution of the HA-HZ of Example 1-1 (0.1%, 100 mM phosphate buffer (pH 7.0)), and the mixture was stirred for 2 hours at room temperature. The reaction mixture was washed with 100 mM phosphate buffer (pH 7.0) to obtain hyaluronic acid-coated PLGA microspheres. Photographs, taken with SEM and a 3D laser microscope, of the resulting hyaluronic acid-coated PLGA microspheres are shown in FIGS. 1 and 2. The SEM photograph (dry state) (FIG. 1) shows that the HA coating smoothed the surfaces of the PLGA microspheres. The 3D laser microscope photograph (FIG. 2) shows that in the aqueous solution, the resulting hyaluronic acid-coated PLGA microspheres had PLGA particles coated with a gelled shell of HA.

Example 2

Preparation of Hyaluronic Acid-Coated PLA Nanospheres

Example 2-1

Synthesis of Hyaluronic Acid Having PLA Introduced therein (HA-PLA)

HA-HZ (100 mg) obtained in the same manner as in Example 1-1 was dissolved in 20 mL of water (concentration 0.5%), and 4 mL of a cation exchange resin of the H type (Dowex 50WX8-400, 4.8 meq/g) was added (ion exchange capacity 100 times that of the carboxyl groups of HA), followed by allowing the mixture to stand for 3 days at room temperature. The supernatant was recovered, and passed through a 0.22 μm filter. To the filtrate, 150 μL of a 1M TBA-OH (tetra-N-butylammonium hydroxide) solution was added. After being adjusted to pH 8, the mixture was lyophilized. PLA0005 (molecular weight 5,000 daltons), EDC and NHS, each in an amount which was at a molar ratio of 5:1 to glucuronic acids (carboxyl groups) contained in the lyophilized HA-HZ-TBA, were dissolved in 10 mL of DMSO, and the solution was allowed to stand for 2 hours at room temperature to convert the carboxyl groups of PLA into active esters. Separately, the HA-HZ-TBA was dissolved in 20 mL of DMSO, and the resulting solution and the above solution were mixed, followed by allowing the mixture overnight at room temperature. The reaction mixture was dialyzed against DMSO (MWCO: 25,000, room temperature, 10 days) to remove the activating reagent, and then the dialyzate was dialyzed against water (MWCO: 12,000-14,000, room temperature, 3 days). The resulting cloudy solution (a nanosphere-dispersed solution containing HA-PLA derived from HA of 25 Kdaltons) was lyophilized (GPC determination of the resulting cloudy solution showed HA-PLA:PLA to be about 1:9). To remove the unreacted PLA, the lyophilizate was charged into acetone, and the insolubles were washed with acetone and dried to obtain HA-PLA. Data from measurement by gel permeation chromatography (GPC) (solvent: DMSO) are shown in FIG. 5. Based on the positions of the peaks, the molecular weight was estimated, with HA-TBA as standard. The molecular weight was confirmed to change from the initial 25 Kdaltons to 97 Kdaltons upon bonding of PLA. The proton NMR spectrum of the resulting HA-PLA is shown in FIG. 6. When the PLA introduction rate of the HA-PLA was determined by the proton NMR method (measuring solvent: DMSO-$d_6$), it was found that 43 mol % of the carboxylic acids of HA were replaced by PLA (HA:N-acetyl group, 1.5-1.9 ppm, PLA:PLA:methine proton at α-position of carbonyl group (except OH terminal), 5.0-5.6 ppm).

GPC Conditions

Eluant: DMSO or DMSO containing 5 mmols/L of $NaNO_3$

Flow rate: 1.0 mL/min

Detector: RI, UV (280 nm)

Column: TOSOH TSKgel $GMH_{HR}$-H

Column temperature: 40° C.

Sample room temperature: 25° C.

Sample concentration: 10 mg/mL, 50 µL

Example 2-2

Preparation of Hyaluronic Acid-Coated PLA Nanospheres by Dialysis Method

The cloudy solution obtained after dialysis against water in the procedure of Example 2-1 was used as a nanosphere-dispersed solution containing HA-PLA derived from HA of 25 Kdaltons.

Separately, HA-HZ was prepared by the same method as in Example 1-1, except that HA with a molecular weight of 190 Kdaltons was used, and this HA was dissolved in distilled water at a concentration of 0.5%. The HA-HZ was subjected to the same method as in Example 2-1, and a reaction mixture after DMSO dialysis was dialyzed against water (MWCO: 25,000, room temperature, 3 days) to prepare a nanosphere-dispersed solution containing HA-PLA derived from HA with 190 Kdaltons.

The resulting dispersed solutions were both cloudy after the purification operation (no sediment was observed). These solutions were diluted 1:100, and measured for the particle size by DLS (Nicomp370). The particle sizes were 263.8 nm for the dispersed solution using HA of 190 kdaltons, and 243.8 nm for the dispersed solution using HA of 25 kdaltons. Upon storage for 1 month at 4° C., the dispersed solutions showed little agglomerated sediment. Photographs of the dispersed solutions after one month of storage are shown in FIGS. 7 and 8. SEM photographs of the dispersed solutions after one month of storage are shown in FIGS. 10 and 11.

Example 2-3

Preparation of Hyaluronic Acid-Coated PLA Nanospheres by Solvent Dispersion Method Of the products using HA of 25 kdaltons in Example 2-1, the lyophilizate of the dispersed solution before purification by acetone reprecipitation (HA-PLA:PLA=about 1:9), and HA-PLA after reprecipitation from acetone were each weighed (20 mg), and dissolved in 1.0 ML of DMSO. Each solution was added dropwise to 4.0 mL of water with stirring to form a pale white translucent solution. The mixed solution was transferred into a dialysis tube (MWCO: 12,000 to 14,000, Spectra/Por4), where it was dialyzed against water (room temperature, 3 days). When the resulting nanosphere dispersed solution was subjected to DLS measurement (Nicomp370), the particle size of the nanospheres was 17.6 nm for the product before purification, and 15.2 nm for the product after purification. Moreover, the nanosphere dispersed solution was dialyzed against $D_2O$ (4° C., 2 days), and subjected to proton NMR measurement (JNM-ECP500 FT NMR SYSTEM, JOEL, measuring solvent: $D_2O$) (product before purification: FIG. 13, product after purification: FIG. 14). Proton peaks derived from HA-HZ were confirmed in both products, thus suggested that the surfaces of the nanospheres were coated with HA molecules.

Example 3

Preparation of Diclofenac-Encapsulating Hyaluronic Acid-Coated PLA Nanospheres

Example 3-1

Methods for Preparation

Solvent Dispersion Method

A lyophilizate (40 mg) of a nanosphere-dispersed solution (HA-PLA:PLA=about 1:9) containing HA-PLA derived from HA of 25 kdaltons, which was prepared by the same procedure as in Example 2-2, and 10 mg of diclofenac (a product purchased from Sigma was reprecipitated from hydrochloric acid for ion exchange to the H type, washed with pure water, and dried) were each weighed, and dissolved in 1.0 mL of DMSO. The solution was added dropwise to 4.0 mL of water with stirring to form a pale white translucent solution. The mixed solution was transferred into a dialysis tube (MWCO: 12,000 to 14,000, Spectra/Por 4), where it was dialyzed against water (3 days, room temperature). The resulting aqueous solution was separated into a precipitate and a supernatant by centrifugation (1,000 rpm×10 min), whereafter the supernatant was recovered and lyophilized.

Dialysis Method

A lyophilizate (40 mg) of a nanosphere-dispersed solution (HA-PLA:PLA=about 1:9) containing HA-PLA derived from HA of 25 kdaltons, which was prepared by the same procedure as in Example 2-2, and 10 mg of diclofenac were each weighed, and dissolved in 1.0 mL of DMSO. When the solution was transferred into a dialysis tube (MWCO: 12,000 to 14,000, Spectra/Por 4), and dialyzed against water, it soon became cloudy and precipitated (3 days, room temperature). The resulting aqueous solution was separated into a precipitate and a supernatant by centrifugation (1,000 rpm×10 min), whereafter the supernatant was recovered and lyophilized.

Example 3-2

Determination of Diclofenac in Nanospheres

Preparation of Standard Solutions

A series of doubling dilutions (6 dilutions) of diclofenac, 5.13 mg/mL-acetonitrile were prepared (A). As an internal standard (IS) solution, an n-heptyl 4-hydroxybenzoate, 2.60 mg/mL-acetonitrile solution was prepared (B). Mixtures of 200 µL (A) and 20 µL (B) were formed, and used as standard solutions for diclofenac determination (C).

Extraction of Diclofenac from Nanospheres and Preparation of Sample

From the nanospheres prepared by the solvent diffusion method and the dialysis method, 4.91 mg and 5.45 mg were weighed, and each dissolved in 1.0 mL of acetonitrile. After full stirring, each solution was centrifuged (1,500 rpm×5 min) to extract diclofenac in the sample, and the supernatant was recovered (D). A mixture of 200 µL (D) and 20 µL (B) was formed, and used as a sample for diclofenac determination (E).

Determination of Diclofenac by RPHPLC

The RPHPLC measurement of (C) and (E) was made, and the determination of diclofenac by the IS method was made.

HPLC Conditions
Eluant: 0.1% TFA 60% MeCNaq
Detector: UV (280 nm)
Column: Intakt Cadenza CD-C18
Flow rate: 1.0 mL/min
Amount of sample poured: 10 µL As a result, the diclofenac encapsulation rate was 4.9% by weight for the solvent diffusion method, and 1.4% by weight for the dialysis method.

Comparative Example 1

Preparation of PLA Nanospheres

Comparative Example 1-1

Preparation of PLA Nanospheres

PLA was dissolved in DMSO (0.316 g/mL DMSO), and dialyzed against water in the same manner as in Example 2-3. A cloudy aqueous solution was obtained, but a precipitate was also confirmed. The particle size of the dispersed solution was measured, and found to be 273.3 nm. When the solution was stored for 1 month at 4° C., most of the particles agglomerated and precipitated after 1 day of storage. A photograph of the solution after 1 month of storage is shown in FIG. 9, and an SEM photograph of the solution after 1 month of storage is shown in FIG. 12. The particles were seen to agglomerate.

Example 4

Synthesis of Stealthy Hyaluronic Acid Modification Product by Introduction of Hydrazide Groups and its Functional Evaluation

Example 4-1

Synthesis of Hyaluronic Acid Having HZ Groups Introduced therein (HA-HZ)

HA (DENKI KAGAKU KOGYO K.K.: viscosity average molecular weight 25 kdaltons) (840 mg) was dissolved in distilled water/EtOH=50/50 at a concentration of 0.1%. EDC and ADH were added at a molar ratio of HA units:EDC: ADH=1:4:40, and the mixture was reacted for 2 hours at room temperature, with its pH being kept at 4.7 to 4.8 with 5N hydrochloric acid. The reaction mixture was dialyzed against large excess amounts of a 100 mM sodium chloride solution, a 25% ethanol solution, and distilled water in this sequence (MWCO: 12,000-14,000). The dialyzate was lyophilized to obtain 86.6 mg of hyaluronic acid having hydrazide groups introduced therein (HA-HZ). The results of the NMR spectrum measurement of the resulting HA-HZ in $D_2O$ are shown in FIG. 15. The HZ group introduction rate was determined as the ADH introduction rate by the proton NMR method, and found to be 63.0% with respect to the HA units (disaccharide) (HA:methyl proton of N-acetyl group, 1.85 ppm, HZ:four methylene protons derived from ADH, 1.5, 2.1 and 2.25 ppm).

Example 4-2

Enzyme Resistance Evaluation of HA-HZ

The HA-HZ obtained in Example 4-1 was dissolved in 0.1M phosphate buffer (pH 6.2) at a concentration of 0.5 mg/mL. To 80 µL of this solution, 32 µL of a 0.5 U/mL solution of Hyaluronidase SD (SEIKAGAKU CORP.) was added, and the mixture was incubated for 24 hours at 37° C. An enzyme-free group as a control was similarly treated (data omitted). The samples were each subjected to gel permeation chromatography (may hereinafter be referred to as GPC) and observed for changes in the molecular weight of HA-HZ, and degradation product formation patterns. The conditions for GPC will be shown below.

GPC Conditions
GPC columns: Superdex 200 10/300 GL, Superdex 75 HR 10/30, Superdex Peptide HR 10/30 (all from Amersham Bioscience) (3 columns connected together)
Mobile phase: PBS (pH 7.4)
Elution mode: Isocratic
Flow rate: 0.4 mL/min
Amount of sample injected: 50 µL
Detector: UV, Abs. at 232 nm The GPC profiles of the enzymatic degradation products are shown in FIG. 16. Under the GPC conditions in the studies, the peak top of HA-HZ is observed in about 75 minutes during the retention time, and the disaccharide as the enzymolysis product is observed in about 130 minutes during the retention time.

The sample obtained in Example 4-1 was shown to be markedly inhibited from an enzymolysis-associated decrease in the molecular weight.

Example 4-3

Synthesis of FITC-Incorporated HA-HZ for Pharmacokinetic Studies

The HA-HZ (38.9 mg) obtained in Example 4-1 was dissolved in 50 mM carbonate buffer (pH 9.0) at a concentration of 2.0 mg/mL. Fluorescein isothiocyanate (may hereinafter be referred to as FITC; Pierce Biotechnology Inc.) in an amount of 0.15 mol per mol of the HA units was added as a ⅟₁₀ volume, based on the HA-HZ solution, of a dimethyl sulfoxide (may hereinafter be referred to as DMSO) solution, and the mixture was stirred for 1 hour at room temperature. After the unreacted FITC was removed by a desalting column PD-10 (Amersham Bioscience), succinic anhydride (Wako Pure Chemical Industries, Ltd.) in an amount of 40 mols per mol of the HA units was added as a 1/10 volume, based on the solution roughly purified by PD-10, of a DMSO solution. The mixture was stirred for 1 hour at room temperature to carry out the reaction, and then the reaction mixture was dialyzed against a large excess amount of water for purification, followed by lyophilization, to obtain fluorescence-labeled HA-HZ (380 mg) having the HA-HZ of Example 4-1 labeled with FITC.

The resulting fluorescence-labeled HA-HZ was dissolved at a concentration of 0.25 mg/mL in 50 mM carbonate buffer (pH 9.0). The FITC concentration was determined by the absorbance at 494 nm of the solution, and the following simultaneous equations were solved to calculate the concentration of each unit. Further, the concentration was converted to the molar fraction, and the weight fraction derived from HA in the HA modification product was calculated.

Unmodified HA units: x nmol/mL
HA-SUC units: y nmol/mL (units having residual HZ treated with succinic anhydride)

$(379.3 \times x)+(635.57 \times y)+(924.88 \times (\text{FITC concentration}))=250 \text{ mg}$     Equation 1

$x/(y+(\text{FITC concentration}))=(100-\text{HZ}(\%))/\text{HZ}(\%)$     Equation 2

The fluorescence-labeled HA-HZ of Example 4-3 was shown to have a HZ introduction rate of 63% and a FITC introduction rate of 1.5%.

Example 4-4

Stealth Evaluation by Pharmacokinetic Studies

HA-Administered Rat Plasma Sample

The fluorescence-labeled HA derivative of Example 4-3 was intravenously administered to rats at a single dose of 10 mg/kg (calculated as hyaluronic acid). Before administration, and 0.25, 1, 2, 4, 6, 8, 10, 12, 24, 30 and 54 hours after administration, the blood was drawn (heparinized), and centrifuged to obtain plasmas. These plasma samples were stored in frozen condition at −20° C. or lower until measurement.

Measuring Method

Standard samples for a calibration curve and samples for measurement are analyzed by GPC. The conditions are shown below.

GPC Conditions
GPC column: TSKgel G6000PWXL
Mobile phase: PBS (pH 7.4)
Elution mode: Isocratic
Flow rate: 0.5 mL/min
Amount of sample injected: 40 μL
Detector: Fluorescence (EX:490, EM:518)

Samples for calibration curve: Each fluorescence-labeled HA derivative was diluted with PBS (pH 7.4) to prepare standard solutions containing 1, 5, 10, 50, 100, 500 μg/mL and 0 μg/mL (control, PBS (pH 7.4)). To these standard solutions, an equal volume of normal rat plasma was added to prepare samples for a calibration curve.

Preparation of samples for measurement: To the HA modification product administered rat plasma samples, an equal volume of PBS (pH 7.4) was added to prepare samples for measurement.

Calculation of HA modification product concentration in plasma: Using an analytic software Millenium, the peak area was calculated. The HA modification product concentration in the plasma was calculated from a calibration curve obtained from the peak areas of the respective standard samples.

Pharmacokinetic Data

In connection with the data on blood concentration changes of the fluorescence-labeled HA derivative of Example 4-3, pharmacokinetic parameters were calculated by WinNonlin Ver 3.3 (Pharsight). Using the data at the last three measurement points in each individual, model-undependent analysis was conducted to calculate the half-life (t½), and the mean blood residence time (MRT). The calculated pharmacokinetic parameters are shown in Table 1.

TABLE 1

| Pharmacokinetic parameters of FITC-labeled HA derivative | | | | |
|---|---|---|---|---|
| HAMw (kdalton) | HZ (%:NMR) | Cl (mL/hr/kg) | MRT (h) | t½ (h) |
| Ex. 4-3 | | | | |
| 25 | 63 | 4.03 ± 0.3 | 32.8 ± 1.7 | 25.2 ± 2.0 |

The pharmacokinetic studies using the fluorescence-labeled HA derivative confirmed that the HA derivative having hydrazide groups introduced therein was improved in the blood residence time after rat single-dose intravenous administration, in comparison with the unmodified HA. The blood half-life (t½) of the unmodified HA was as short as several minutes, whereas the blood half-life increased to 25.2±2.0 (hours) after introduction of hydrazide groups.

Example 5

Synthesis of Stealthy Hyaluronic Acid Modification Product by Introduction of Amino Groups and its Functional Evaluation

Example 5-1

Synthesis-1 of Hyaluronic Acid Having AM Groups Introduced therein (HA-AM)

HA-TBA (305.2 mg), which prepared with HA (DENKI KAGAKU KOGYO K.K.: viscosity average molecular weight 19 kdaltons) by forming tetrabutylammonium (TBA) salt using TBA-incorporated DOWEX 50WX8-400 (Aldrich Chemical Co., Inc.), was dissolved at a concentration of 2 mg/mL in DMSO. Ethylenediamine (EDA) (Sigma-Aldrich Corp.) and BOP (Wako Pure Chemical Industries, Ltd.) were added in this order at a molar ratio of HA units:BOP:EDA=1:1.1:50, and the mixture was reacted overnight at room temperature. Then, 80 mL was pipetted from the reaction mixture, and a 1M aqueous solution of NaCl was added in an amount of 40 mL, half of 80 mL. Then, the pH value of the mixture was decreased to pH 3 with 5N HCl, and further neutralized with 2N NaOH. The mixture was dialyzed against a large excess amount of water (Spectra/Por 7, MWCO: 12,000-14,000 daltons) for purification, and subjected to ultrafiltration. Then, the filtrate was lyophilized to obtain 110 mg of the captioned hyaluronic acid having amino groups introduced therein. The results of the NMR spectrum measurement of the resulting HA-AM in $D_2O$ are shown in FIG. 17.

The HZ group introduction rate was determined as the AM introduction rate by the proton NMR method, and found to be 94.0% with respect to the HA units (disaccharide) (HA: methyl proton of N-acetyl group, 1.85 ppm, AM: one methylene proton derived from EDA, 2.98 ppm). The NMR measurement was conducted under the same conditions (parameters) as in Example 4-1 using JNM-ECA500 (500 MHZ spectroscope) as an NMR spectroscope.

Example 5-2

Synthesis-2 of Hyaluronic Acid Having AM Groups Introduced therein (HA-AM)

Hyaluronic acid having amino groups introduced therein (HA-AM) was obtained by the same method as in Example 5-1, except that HA-TBA prepared by forming a TBA salt with HA (DENKI KAGAKU KOGYO K.K.: viscosity average molecular weight 200 kdaltons) was used, and the molar ratio of HA units:BOP:ethylenediamine (EDA)=1:1.08:50. Determination by the proton NMR method (measuring solvent: $D_2O$) showed the AM group introduction rate to be 68.0% with respect to the HA units (disaccharide) (HA:methyl proton of N-acetyl group, 1.89 ppm, HZ:one methylene proton derived from AM, 3.00 ppm).

Example 5-3

Synthesis-3 of Hyaluronic Acid Having AM Groups Introduced therein (HA-AM)

Hyaluronic acid having amino groups introduced therein (HA-AM) was obtained by the same method as in Example 5-1, except that the molar ratio of HA units:BOP:2,2-(ethylenedioxy)bis(ethylamine) (EDOBEA) (Sigma-Aldrich Corp.)=1:1.0:50. Determination by the proton NMR method (measuring solvent: $D_2O$) showed the AM group introduction rate to be 58.0% with respect to the HA units (disaccharide) (HA:methyl proton of N-acetyl group, 1.89 ppm, HZ:one methylene proton derived from AM, 3.05 ppm).

Example 5-4

Enzyme Resistance Evaluation of HA-AM

The HA-AM products obtained in Examples 5-1 to 5-3 were each dissolved in water at a concentration of 2 mg/mL. To 55 μL of this solution, 132 μL of 0.2M phosphate buffer (pH 6.2) and 77 μL of water were added. Further, 44 μL of a 1 U/mL solution of Hyaluronidase SD (SEIKAGAKU CORP.) (0.05M phosphate buffer (pH 6.2) containing 0.01% BSA) was added, and the mixture was incubated for 24 hours at 37° C. An enzyme-free group as a control was similarly treated (data omitted). The samples were each subjected to gel permeation chromatography (may hereinafter be referred to as GPC) and observed for changes in the molecular weight of HA-AM, and degradation product formation patterns. GPC was performed under the same conditions (parameters) as in Example 4-2.

The GPC profiles of the enzymatic degradation products are shown in FIG. 18. Under the GPC conditions in the present studies, the disaccharide as the enzymolysis product is observed in about 130 minutes during the retention time. The samples obtained in Examples 5-1 to 5-3 were shown to be markedly inhibited from enzymolysis-associated decreases in the molecular weight.

Example 6

Synthesis and Solubility Evaluation of Hyaluronic Acid having PLA Incorporated therein

Example 6-1

TBA Salt Formation of Hyaluronic Acid Having HZ Groups Introduced therein (HA-HZ)

HA-HZ (1000 mg) obtained in the same manner as in Example 4-1 was dissolved in 1,000 mL of distilled water (concentration 0.1%), and 37.5 mL of a cation exchange resin of the H type (Dowex 50WX8-400, 2.1 meq/g) was added (ion exchange capacity 100 times that of the carboxyl groups of HA), followed by allowing the mixture to stand overnight at room temperature. The supernatant was recovered, and filtered through a 0.22 μm filter. Then, the filtrate was adjusted to pH 7.0 with the addition of 1.85 μL of a 40 wt. % TBA-OH aqueous solution. The resulting aqueous solution was lyophilized to obtain a white powder of TBA salt-converted HA-HZ. The yield was 932.8 mg.

Example 6-2

Synthesis of Hyaluronic Acid Having PLA (Viscosity Average Molecular Weight 5 Kdaltons) Introduced therein (HA-HZ-PLA)

PLA0005 (Wako Pure Chemical Industries, Ltd.: viscosity average molecular weight 5 kdaltons, number average molecular weight 2.83 kdaltons), EDC and NHS were dissolved in anhydrous DMSO at a PLA concentration of 25 mg/mL and at PLA/EDC/NHS=1/1/1 (molar ratio). The solution, while being tightly stoppered, was stirred for 3 hours at room temperature to convert the terminal carboxyl groups of PLA into active esters. Separately, the TBA salt-converted HA-HZ prepared in Example 6-1 was dissolved in anhydrous DMSO at a concentration of 5 mg/mL. To the TBA salt-converted HA-HZ solution, anhydrous DMSO and the active ester-converted PLA solution were added sequentially in proportions shown in Table 2 (a to j) (final TBA salt-converted HA-HZ concentration, 1.5 mg/mL). These substances were mixed and, while being tightly stoppered, the mixture was stirred overnight at room temperature. The reaction mixture was dialyzed against distilled water (MWCO: 12,000-14,000, room temperature, 3 days), and the resulting cloudy solution was lyophilized. The lyophilizate was washed with an excess of acetone, and then washed with an excess of ethanol. The insolubles were dried under reduced pressure to obtain a white powder of HA-HZ-PLA. GPC chromatograms of the respective products, obtained using DMSO as a solvent, are shown in FIG. 19. The conditions for GPC are as shown below.

GPC Conditions
GPC column: GMHHR-H (TOSOH)
Mobile phase: 10 mM $NaNO_3$ (pH 7.4)
Elution mode: Isocratic
Flow rate: 1.0 mL/min
Amount of sample injected: 50 μL
Detector: UV, Abs. at 280 nm
Sample concentration: 5.0 mg/mL Since the peaks are shifted to the high molecular side, it was suggested that the molecular weight was increased by introducing PLA. The proton NMR spectra of the resulting HA-HZ-PLA products in DMSO-$d_6$ are shown in FIG. 20. When the PLA introduction rates of the HA-HZ-PLA's were determined by the NMR method, they ranged from 1.0 to 46.1% with respect to the HA units (disaccharide), as shown in Table 3, on the assumption that the molecular weight distribution of PLA is not different between the starting material and the PLA-introduced product. The weight ratio of PLA in the HA-HZ-PLA molecules was 5.7 to 73.4% w/w (HA: methyl proton of N-acetyl group, 1.85 ppm, PLA:methine proton at α-position of carbonyl group (except OH terminal), 5.0-5.6 ppm).

TABLE 2

Conditions for Synthesis of HA-HZ-PLA in Example 6-2

| Sample | Equivalent ratio (PLA/HA unit) | Amount of TBA HA-HZ solution used (mL) | Amount of anhydrous DMSO used (mL) | Amount of activated PLA solution used (mL) |
|---|---|---|---|---|
| a | 1.3 | 6.0 | 13.92 | 0.08 |
| b | 2.6 | 6.0 | 13.84 | 0.16 |
| c | 6.5 | 6.0 | 13.61 | 0.39 |
| d | 13.0 | 6.0 | 13.21 | 0.79 |
| e | 26.0 | 6.0 | 12.42 | 1.58 |
| f | 39.0 | 6.0 | 11.64 | 2.36 |
| g | 52.0 | 6.0 | 10.85 | 3.15 |
| h | 65.0 | 6.0 | 10.06 | 3.94 |
| i | 130.0 | 6.0 | 6.12 | 7.88 |
| j | 195.0 | 6.0 | 2.18 | 11.82 |

TABLE 3

Results of synthesis of HA-HZ-PLA obtained in Example 6-2

| Sample | Yield (mg) | PLA introduction rate (%) | PLA weight ratio (% w/w) |
|---|---|---|---|
| a | 15.3 | 1.0 | 5.7 |
| b | 15.8 | 2.0 | 10.6 |
| c | 19.6 | 4.1 | 19.6 |
| d | 22.2 | 7.3 | 30.0 |
| e | 25.8 | 12.5 | 42.5 |
| f | 28.3 | 13.6 | 44.6 |
| g | 26.9 | 17.1 | 50.4 |
| h | 29.8 | 20.8 | 55.3 |
| i | 32.6 | 35.4 | 67.9 |
| j | 35.3 | 46.1 | 73.4 |

Example 6-3

Synthesis of Hyaluronic Acid Having PLA (Viscosity Average Molecular Weight 20 Kdaltons) Introduced therein (HA-HZ-PLA)

A white powder of HA-HZ-PLA was obtained in the same manner as in Example 6-2, except that PLA-0005 was replaced by PLA-0020 (Wako Pure Chemical Industries, Ltd.: viscosity average molecular weight 20 kdaltons, number average molecular weight 8.73 kdaltons), and the mixing ratio of TBA salt-converted HA-HZ solution, anhydrous DMSO, and the active ester-converted PLA solution was changed as in Table 4 (k to t). GPC chromatograms of the respective products are shown in FIG. 21. The proton NMR spectra of these products are shown in FIG. 22. When the PLA introduction rates of the HA-HZ-PLA's were determined by the NMR method (measuring solvent: DMSO-$d_6$), they ranged from 0.9 to 12.8% for the HA units (disaccharide), as shown in Table 5, on the assumption that the molecular weight distribution of PLA is not different between the starting material and the PLA-introduced product. The weight ratio of PLA in the HA-HZ-PLA molecules was 13.5 to 69.9% w/w (HA:methyl proton of N-acetyl group, 1.85 ppm; PLA: methine proton at α-position of carbonyl group (except OH terminal), 5.0-5.6 ppm).

TABLE 4

Conditions for Synthesis of HA-HZ-PLA in Example 6-3

| Sample | Equivalent ratio (PLA/HA unit) | Amount of TBA HA-HZ solution used (mL) | Amount of anhydrous DMSO used (mL) | Amount of activated PLA solution used (mL) |
|---|---|---|---|---|
| k | 1.3 | 12.0 | 27.52 | 0.48 |
| l | 2.6 | 12.0 | 27.04 | 0.96 |
| m | 6.5 | 12.0 | 25.59 | 2.41 |
| n | 13.0 | 12.0 | 23.18 | 4.82 |
| o | 19.5 | 12.0 | 20.77 | 7.23 |
| p | 26.0 | 12.0 | 18.37 | 9.63 |
| q | 32.5 | 12.0 | 15.96 | 12.04 |
| r | 39.0 | 12.0 | 13.55 | 14.45 |
| s | 52.0 | 12.0 | 8.73 | 19.27 |
| t | 65.0 | 12.0 | 3.92 | 24.08 |

TABLE 5

Yield, PLA introduction rate and PLA weight ratio of HA-HZ-PLA obtained in Example 6-3

| Sample | Yield (mg) | PLA introduction rate (%) | PLA weight ratio (% w/w) |
|---|---|---|---|
| k | 40.2 | 0.9 | 13.5 |
| l | 25.2 | 1.1 | 17.2 |
| m | 44.1 | 1.7 | 23.4 |
| n | 48.0 | 2.7 | 33.2 |
| o | 52.2 | 3.9 | 41.2 |
| p | 55.4 | 4.9 | 47.2 |
| q | 58.7 | 5.5 | 49.9 |
| r | 62.1 | 6.6 | 54.5 |
| s | 57.7 | 9.7 | 63.7 |
| t | 75.3 | 12.8 | 69.9 |

Example 6-4

Dispersibility or Solubility of HA-HZ-PLA in Water and DMSO

HA-HZ obtained by the same method as in Example 4-1, and the white powders of HA-HZ-PLA prepared in Examples 6-2 and 6-3 were each weighed (about 5 mg), and distilled water was added to a concentration of 5 mg/mL, followed by stirring the mixture overnight at room temperature. Stirring was stopped, and the appearance after the mixture was allowed to stand for 3 days at room temperature was inspected visually. The results are shown in Table 6. As a result, HA-HZ-PLA was suggested to be easily uniformly dispersible in water at a PLA weight ratio of 5.7 to 19.6% w/w, and difficultly dispersible in water at a higher PLA weight ratio. In connection with the products showing no precipitate, their solutions were centrifuged (1,500 g, 10 min), whereby all of the solutions showed a white precipitate, with the exception of the HA-HZ aqueous solution. The results suggested HA-HZ-PLA to be minimally soluble in water and, if dispersed, have low dispersion stability, in the ranges practiced in Examples 6-2 and 6-3 (PLA weight ratio 5.7 to 73.4% w/w).

Next, HA-HZ obtained by the same method as in Example 4-1, and the white powders of HA-HZ-PLA prepared in Examples 6-2 and 6-3 were each weighed (about 5 mg), and DMSO was added to a concentration of 5 mg/mL, followed by stirring the mixture overnight at room temperature. The solubility of the mixture during this process was inspected visually. The results are shown in Table 6. As a result, HA-HZ-PLA was suggested to have solubility in DMSO when PLA was at least at a weight ratio of 5.7 to 73.4% w/w.

TABLE 6

Appearance of solution or dispersion of HA-HZ-PLA obtained in Examples 6-2 and 6-3

| Sample | PLA weight ratio (% w/w) | Appearance of aqueous solution (5 mg/mL) (after stirring, followed by allowing to stand) | Appearance of aqueous solution (5 mg/mL) (after centrifugation) | Appearance of DMSO solution (5 mg/mL) |
|---|---|---|---|---|
| HA-HZ | 0.0 | colorless, transparent | colorless, transparent | colorless, transparent |
| a | 5.7 | pale white | pale white (white precipitate present) | colorless, transparent |
| b | 10.6 | pale white | pale white (white precipitate present) | colorless, transparent |
| c | 19.6 | pale white | pale white (white precipitate present) | colorless, transparent |
| d | 30.0 | pale white (white precipitate present) | — | colorless, transparent |
| e | 42.5 | pale white (white precipitate present) | — | colorless, transparent |
| f | 44.6 | pale white (white precipitate present) | — | colorless, transparent |
| g | 50.4 | pale white (white precipitate present) | — | colorless, transparent |
| h | 55.3 | pale white (white precipitate present) | — | colorless, transparent |
| i | 67.9 | colorless, transparent (white precipitate present) | — | colorless, transparent |
| j | 73.4 | colorless, transparent (white precipitate present) | — | colorless, transparent |
| k | 13.5 | pale white | pale white (white precipitate present) | colorless, transparent |
| l | 17.2 | pale white | pale white (white precipitate present) | colorless, transparent |
| m | 23.4 | pale white (white precipitate present) | — | colorless, transparent |
| n | 33.2 | pale white (white precipitate present) | — | colorless, transparent |
| o | 41.2 | pale white (white precipitate present) | — | colorless, transparent |
| p | 47.2 | colorless, transparent (white precipitate present) | — | colorless, transparent |
| q | 49.9 | colorless, transparent (white precipitate present) | — | colorless, transparent |
| r | 54.5 | colorless, transparent (white precipitate present) | — | colorless, transparent |
| s | 63.7 | colorless, transparent (white precipitate present) | — | colorless, transparent |
| t | 69.9 | colorless, transparent (white precipitate present) | — | colorless, transparent |

Example 6-5

Solubilization of HA-HZ-PLA in Water by Solvent Substitution

HA-HZ obtained by the same method as in Example 4-1, and the white powders of HA-HZ-PLA prepared in Examples 6-2 and 6-3 were each weighed (about 5 mg), and dissolved in DMSO to a concentration of 5 mg/mL. This DMSO solution (0.6 mL) was mixed with 2.4 mL of distilled water, and the mixture was dialyzed against distilled water (MWCO: 12,000-14,000, room temperature, 3 days). The resulting aqueous solutions were all colorless, transparent solutions. Each of the aqueous solutions was centrifuged (40,000 g, 10 min), but no precipitate was observed. As a result, it was suggested that HA-HZ-PLA, with its PLA weight ratio being in the range of 5.7 to 73.4% w/w, could be dissolved in water by dissolving it in DMSO once, and then substituting the solvent by water.

Example 7

Synthesis of Hyaluronic Acid Modification Product Having PLA Introduced therein for Study of Process for Preparing Hyaluronic Acid-Coated PLA (PLGA) Fine Particles

Example 7-1

Synthesis of HA-HZ Having Functions of Intact HA Remaining

HA (DENKI KAGAKU KOGYO K.K.: viscosity average molecular weight 23 kdaltons) (101217 mg) was dissolved at a concentration of 0.1% in distilled water/EtOH=50/50. EDC and ADH were added at a molar ratio of HA units:EDC: ADH=1:0.1:40, and the mixture was reacted for 2 hours at room temperature, with its pH being maintained at 4.7 to 4.8 with 5N hydrochloric acid. The reaction mixture was dialyzed against large excess amounts of a 100 mM sodium chloride solution, a 25% ethanol solution, and distilled water in this sequence (MWCO: 12,000-14,000). The dialyzate (about 10 mL) was lyophilized for measurement of the HZ group introduction rate. The HZ group introduction rate was determined as the ADH introduction rate by the proton NMR method (measuring solvent: $D_2O$), and found to be 9.0% with respect to the HA units (disaccharide) (HA: methyl proton of N-acetyl group, 1.85 ppm, HZ: four methylene protons derived from ADH, 1.5, 2.1 and 2.25 ppm).

Example 7-2

TBA Salt Formation of HA-HZ Having Functions of Intact HA Remaining

To an aqueous solution of the HA-HZ (concentration: about 0.1%) prepared in Example 7-1, 50 mL of a cation exchange resin of the H type (Dowex 50WX8-400, 2.1 meq/g) was added, and the mixture was allowed to stand overnight at room temperature. The supernatant was recovered, and filtered through a 0.22 µm filter. Then, the filtrate was adjusted to pH 7.0 with the addition of 1,150 µL of a 40 wt. % TBA-OH aqueous solution. The resulting aqueous solution was lyophilized to obtain a white powder of TBA salt-converted HA-HZ. The yield was 1,113.6 mg.

Example 7-3

Synthesis of Hyaluronic Acid Having PLA (5 Kdaltons) Introduced therein and Having Functions of Intact HA Remaining (HA-HZ-PLA)

A white powder of HA-HZ-PLA was obtained in the same manner as in Example 6-2, except that the TBA salt-converted HA-HZ prepared in Example 7-2 was used, and the mixing ratio of TBA salt-converted HA-HZ solution, anhydrous DMSO, and the active ester-converted PLA solution was changed as in Table 7. When the PLA introduction rate of the HA-HZ-PLA was determined by the NMR method (measuring solvent: $DMSO-d_6$), it was 8.0% with respect to the HA units (disaccharide), on the assumption that the molecular weight distribution of PLA is not different between the starting material and the PLA-introduced product. The weight ratio of PLA in the HA-HZ-PLA molecules was 36.7% w/w (HA:methyl proton of N-acetyl group, 1.85 ppm; PLA: methine proton at α-position of carbonyl group (except OH terminal), 5.0-5.6 ppm).

Example 7-4

Synthesis of Hyaluronic Acid Having PLA (20 Kdaltons) Introduced therein and Having Functions of Intact HA Remaining (HA-HZ-PLA)

A white powder of HA-HZ-PLA was obtained in the same manner as in Example 6-2, except that the TBA salt-converted HA-HZ prepared in Example 7-2 was used, PLA-0005 of Example 6-2 was replaced by PLA-0020, and the mixing ratio of TBA salt-converted HA-HZ solution, anhydrous DMSO, and the active ester-converted PLA solution was changed as in Table 7. When the PLA introduction rate of the HA-HZ-PLA was determined by the NMR method (measuring solvent: $DMSO-d_6$), it was 1.9% with respect to the HA units (disaccharide), on the assumption that the molecular weight distribution of PLA is not different between the starting material and the PLA-introduced product. The weight ratio of PLA in the HA-HZ-PLA molecules was 29.5% w/w (HA:methyl proton of N-acetyl group, 1.85 ppm; PLA:methine proton at α-position of carbonyl group (except OH terminal), 5.0-5.6 ppm).

Example 7-5

Synthesis of Stealthy Hyaluronic Acid Having PLA (5 Kdaltons) Introduced therein at a Low Introduction Rate (HA-HZ-PLA)

A white powder of HA-HZ-PLA was obtained in the same manner as in Example 6-2, except that TBA salt-converted HA-HZ prepared in the same manner as in Example 6-1 was used, and the mixing ratio of TBA salt-converted HA-HZ solution, anhydrous DMSO, and the active ester-converted PLA solution in Example 6-2 was changed as in Table 7. When the PLA introduction rate of the HA-HZ-PLA was determined by the NMR method (measuring solvent: $DMSO-d_6$), it was 4.5% with respect to the HA units (disaccharide), on the assumption that the molecular weight distribution of PLA is not different between the starting material and the PLA-introduced product. The weight ratio of PLA in the HA-HZ-PLA molecules was 21.1% w/w (HA:methyl proton of N-acetyl group, 1.85 ppm; PLA:methine proton at α-position of carbonyl group (except OH terminal), 5.0-5.6 ppm).

Example 7-6

Synthesis of Stealthy Hyaluronic Acid Having PLA (5 Kdaltons) Introduced therein at a High Introduction Rate (HA-HZ-PLA)

A white powder of HA-HZ-PLA was obtained in the same manner as in Example 6-2, except that TBA salt-converted HA-HZ prepared in the same manner as in Example 6-1 was used, and the mixing ratio of TBA salt-converted HA-HZ solution, anhydrous DMSO, and the active ester-converted PLA solution in Example 6-2 was changed as in Table 7. When the PLA introduction rate of the HA-HZ-PLA was determined by the NMR method (measuring solvent: DMSO-$d_6$), it was 30.9% for the HA units (disaccharide), on the assumption that the molecular weight distribution of PLA is not different between the starting material and the PLA-introduced product. The weight ratio of PLA in the HA-HZ-PLA molecules was 65.1% w/w (HA:methyl proton of N-acetyl group, 1.85 ppm; PLA:methine proton at α-position of carbonyl group (except OH terminal), 5.0-5.6 ppm).

tion was stirred for 20 minutes at room temperature to convert the terminal carboxyl groups of PLA into active esters.

The active ester solution was added to the HA-AM solution such that the amount of carboxylic acids was twice the amount of the amino groups of the HA-AM, followed by stirring the mixture overnight at room temperature.

The reaction mixture was dialyzed (MWCO: 12,000-14,000, room temperature, 2 days) against DMSO four times and against water five times, and the resulting cloudy solution was lyophilized. The lyophilizate was washed with an excess of acetone, and then washed with an excess of ethanol. The insolubles were dried under reduced pressure to obtain 365.1 mg of a white powder of HA-AM-PLA.

The proton NMR spectrum of the resulting HA-AM-PLA in DMSO-$d_6$ is shown in FIG. 23. When the PLA introduction rate of the HA-AM-PLA was determined by the NMR method (measuring solvent: DMSO-$d_6$), it was 87.2% with respect to the HA units (disaccharide) on the assumption that the molecular weight distribution of PLA is not different between the starting material and the PLA-introduced product. The weight ratio of PLA in the HA-AM-PLA molecules was 86.1% w/w (HA:methyl proton of N-acetyl group, 1.85

TABLE 7

Conditions for Synthesis of HA-HZ-PLA in Examples 7-3 to 7-6

| Sample | HZ (%) | PLA molecular weight (kdaltons) | Equivalent ratio (PLA/HA unit) | TBA HA-HZ solution (mL) | Anhydrous DMSO (mL) | Activated PLA solution (mL) |
|---|---|---|---|---|---|---|
| Ex. 7-3 | 9.0 | 5 | 10.0 | 80.0 | 179.5 | 7.5 |
| Ex. 7-4 | 9.0 | 20 | 10.0 | 80.0 | 164.2 | 22.8 |
| Ex. 7-5 | 63.0 | 5 | 6.5 | 100.0 | 226.4 | 6.6 |
| Ex. 7-6 | 63.0 | 5 | 130.0 | 100.0 | 101.7 | 131.3 |

TABLE 8

Results of synthesis of HA-HZ-PLA in Examples 7-3 to 7-6

| Sample | Yield (mg) | PLA introduction rate (%) | PLA weight ratio (% w/w) |
|---|---|---|---|
| Ex. 7-3 | 331.6 | 8.0 | 36.7 |
| Ex. 7-4 | 313.1 | 1.9 | 29.5 |
| Ex. 7-5 | 420.1 | 4.5 | 21.1 |
| Ex. 7-6 | 750.0 | 30.9 | 65.1 |

Example 7-7

Synthesis of Stealthy Hyaluronic Acid Having PLA (5 Kdaltons) Introduced therein at a High Introduction Rate (HA-AM-PLA)

A DMSO solution of HA-AM obtained in the same manner as in Example 5-1 was dialyzed against 1 L of DMSO four times (MWCO: 12,000-14,000, room temperature) to remove impurities such as unreacted EDA and BOP.

PLA0005 (Wako Pure Chemical Industries, Ltd.: viscosity average molecular weight 5 kdaltons, number average molecular weight 2.83 kdaltons), EDC and NHS were dissolved in anhydrous DMSO at a PLA concentration of 10 mg/mL and at PLA/EDC/NHS=1/1/1 (molar ratio). The soluppm, PLA:methine proton at α-position of carbonyl group (except OH terminal), 5.0-5.6 ppm).

Example 8

Preparation of HA-HZ-PLA Aqueous Solution for Study of Process for Preparing Hyaluronic Acid-Coated PLA (PLGA) Fine Particles

Example 8-1

Preparation of HA-HZ-PLA Aqueous Solution

Of the HA-HZ-PLA prepared in Example 7-3, 250 mg was weighed, and distilled water was added to a concentration of 40 mg/mL, followed by stirring the mixture overnight at room temperature to dissolve the mixture. The resulting aqueous solution was a transparent solution in a slightly white color.

Example 8-2

Preparation-1 of HA-HZ-PLA Aqueous Solution by DMSO Solvent Diffusion Method

Of the HA-HZ-PLA prepared in Example 7-4, 250 mg was weighed, and DMSO was added to a concentration of 5.0 mg/mL to dissolve the HA-HZ-PLA. The solution was mixed with distilled water whose amount was 4 times the amount of the DMSO added, and then the mixture was dialyzed against distilled water (MWCO: 10,000, room temperature, 1 day). The resulting aqueous solution was a colorless, transparent solution. This aqueous solution was filtered through a 5.0 μm filter, and then subjected to ultrafiltration (Vivaspin 20 MWCO: 10,000, Vivascience) for concentration. The determination of the concentration was performed by lyophilizing 200 μL of the resulting concentrated solution, and measuring the weight of the dry powder. The concentration was found to be 5.7 mg/mL, and distilled water was added to the concentrated solution to a concentration of 2.0 mg/mL, whereafter the system was thoroughly mixed.

Example 8-3

Preparation-2 of HA-HZ-PLA Aqueous Solution by DMSO Solvent Diffusion Method

Of the HA-HZ-PLA prepared in Example 7-5, 150 mg was weighed, and DMSO was added to a concentration of 5.0 mg/mL to dissolve the HA-HZ-PLA. The solution was mixed with distilled water, whose amount was 4 times the amount of the DMSO added, and then the mixture was dialyzed against distilled water (MWCO: 10,000, room temperature, 3 days). The resulting aqueous solution was a colorless, transparent solution. This aqueous solution was filtered through a 5.0 μm filter, and then subjected to ultrafiltration (Vivaspin 20 MWCO: 10,000, Vivascience) for concentration. The determination of the concentration was performed by lyophilizing 200 μL of the resulting concentrated solution, and measuring the weight of the dry powder. The concentration was found to be 7.2 mg/mL, and distilled water was further added to the concentrated solution to a concentration of 2.0 mg/mL, whereafter the system was thoroughly mixed.

Example 8-4

Preparation-3 of HA-HZ-PLA Aqueous Solution by DMSO Solvent Diffusion Method

Of the HA-HZ-PLA prepared in Example 7-6, 150 mg was weighed, and DMSO was added to a concentration of 5.0 mg/mL to dissolve the HA-HZ-PLA. The solution was mixed with distilled water, whose amount was 4 times the amount of the DMSO added, and then the mixture was dialyzed against distilled water (MWCO: 10,000, room temperature, 3 days). The resulting aqueous solution was a colorless, transparent solution. This aqueous solution was filtered through a 5.0 μm filter, and then subjected to ultrafiltration (Vivaspin 20 MWCO: 10,000, Vivascience) for concentration. The determination of the concentration was performed by lyophilizing 200 μL of the resulting concentrated solution, and measuring the weight of the dry powder. The concentration was found to be 6.5 mg/mL, and distilled water was further added to the concentrated solution to a concentration of 2.0 mg/mL, whereafter the system was thoroughly mixed.

Example 8-5

Preparation of HA-AM-PLA Aqueous Solution by DMSO Solvent Diffusion Method

Of the HA-AM-PLA prepared in Example 7-7, 20 mg was weighed, and DMSO was added to a concentration of 5.0 mg/mL to dissolve the HA-AM-PLA. The solution was mixed with distilled water, whose amount was 4 times the amount of the DMSO added, and then the mixture was dialyzed against distilled water (MWCO: 10,000, room temperature, 3 days). The resulting aqueous solution was a colorless, transparent solution. This aqueous solution was filtered through a 5.0 μm filter, and then subjected to ultrafiltration (Vivaspin 20 MWCO: 10,000, Vivascience) for concentration. The determination of the concentration was performed by lyophilizing 200 μL of the resulting concentrated solution, and measuring the weight of the dry powder. The concentration was found to be 10.4 mg/mL, and distilled water was further added to the concentrated solution to a concentration of 2.0 mg/mL, whereafter the system was thoroughly mixed.

Example 9

Preparation of Hyaluronic Acid-Coated PLA (PLGA) Fine Particles Intended for Targeting CD44

Example 9-1

Preparation of Hyaluronic Acid-Coated PLA Fine Particles by DMSO Dialysis Method The HA-HZ-PLA prepared in Example 7-4 (12 mg), and 108 mg of PLA-0005 were weighed, and dissolved in 3 mL of DMSO. The solution was dialyzed against distilled water (MWCO: 10,000, room temperature, 3 days), and the dialyzate was put through a 32 μm sieve to remove agglomerates. Then, a washing operation, which comprised centrifugation (1,500 g, 10 min), removal of the supernatant, and addition of distilled water, was repeated about 3 times. Then, the precipitate (hyaluronic acid-coated PLA fine particles) was recovered, and lyophilized. The yield of the resulting white powder was 53.2 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 153 μg (proportion of HA-HZ-PLA in the fine particles, 0.29% w/w). The particle size of the fine particles was measured by redispersing the white powder composed of the Hyaluronic acid-coated PLA fine particles in distilled water, picking up 50 of the fine particles randomly by optical microscopic observation, and analyzing their images. The mean value of the particle sizes, and the standard deviation were found to be 1.0±0.1 μm.

Example 9-2

Preparation-1 of Hyaluronic Acid-Coated PLA Fine Particles by DMSO Solvent Diffusion Method PLA-0005 (40 mg) was weighed, and dissolved in 1 mL of DMSO. The solution was added dropwise to, and mixed with, 4 mL of the HA-HZ-PLA aqueous solution, which was prepared in Example 8-1, with stirrer agitation. The resulting mixed solution was dialyzed against distilled water (MWCO: 10,000, room temperature, 3 days), and the dialyzate was filtered through a 5.0 μm filter to remove agglomerates. Then, a washing operation, which comprised centrifugation (40,000 g, 10 min), removal of the supernatant, and addition of distilled water, was repeated about 3 times. Then, the precipitate (hyaluronic acid-coated PLA fine particles) was recovered, and lyophilized. The yield of the resulting white powder was 140 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 60 μg (proportion of HA-HZ-PLA in the fine particles, 0.43% w/w). DLS measurement (Nicomp370) of the dialyzate showed the measured value of the particle size to be 225.3 nm.

Example 9-3

Preparation-2 of Hyaluronic Acid-Coated PLA Fine Particles by DMSO Solvent Diffusion Method PLA-0005 (40 mg) was weighed, and dissolved in 1 mL of DMSO. The solution was added dropwise to, and mixed with, 4 mL of distilled water with stirrer agitation. The resulting mixed solution was dialyzed against distilled water (MWCO: 10,000, room temperature, 3 days), and the dialyzate was filtered through a 5.0 µm filter to remove agglomerates. Then, the filtrate was added dropwise to, and mixed with, 4 mL of the HA-HZ-PLA aqueous solution prepared in Example 8-1, followed by stirring the mixture for about 15 minutes. Then, a washing operation, which comprised centrifugation (40,000 g, 10 min), removal of the supernatant, and addition of distilled water, was repeated about 3 times. Then, the precipitate (hyaluronic acid-coated PLA fine particles) was recovered, and lyophilized. The yield of the resulting white powder was 23.9 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 22 µg (proportion of HA-HZ-PLA in the fine particles, 0.09% w/w). DLS measurement (Nicomp370) of the dialyzate showed the measured value of the particle size to be 308.9 nm.

Example 9-4

Preparation-3 of Hyaluronic Acid-Coated PLA Fine Particles by DMSO Solvent Diffusion Method The HA-HZ-PLA prepared in Example 7-4 (4 mg), and 36 mg of PLA-0005 were weighed, and dissolved in 1 mL of DMSO. The solution was added dropwise to, and mixed with, 4 mL of distilled water with stirrer agitation. The resulting mixed solution was dialyzed against distilled water (MWCO: 10,000, room temperature, 3 days), and the dialyzate was filtered through a 5.0 µm filter to remove agglomerates. Then, a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 3.7 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 70 µg (proportion of HA-HZ-PLA in the fine particles, 1.89% w/w). DLS measurement (Nicomp370) of the dialyzate showed the measured value of the particle size to be 288.2 nm.

Example 9-5

Preparation-4 of Hyaluronic Acid-Coated PLA Fine Particles by DMSO Solvent Diffusion Method PLA-0005 (40 mg) was weighed, and dissolved in 1 mL of DMSO. The solution was added dropwise to, and mixed with, 4 mL of the HA-HZ-PLA aqueous solution, which was prepared in Example 8-2, with stirrer agitation. The resulting mixed solution was dialyzed against distilled water (MWCO: 10,000, room temperature, 3 days), and the dialyzate was filtered through a 5.0 µm filter to remove agglomerates. Then, a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 16.7 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 1 µg (proportion of HA-HZ-PLA in the fine particles, 0.01% w/w). DLS measurement (Nicomp370) of the dialyzate showed the measured value of the particle size to be 220.2 nm.

Example 9-6

Preparation-5 of Hyaluronic Acid-Coated PLA Fine Particles by DMSO Solvent Diffusion Method PLA-0005 (40 mg) was weighed, and dissolved in 1 mL of DMSO. The solution was added dropwise to, and mixed with, 4 mL of distilled water with stirrer agitation. The resulting mixed solution was dialyzed against distilled water (MWCO: 10,000, room temperature, 3 days), and the dialyzate was filtered through a 5.0 µm filter to remove agglomerates. Then, the filtrate was added dropwise to, and mixed with, 4 mL of the HA-HZ-PLA aqueous solution prepared in Example 8-2, followed by stirring the mixture for about 15 minutes. Then, a washing operation, which comprised centrifugation (40,000 g, 10 min), removal of the supernatant, and addition of distilled water, was repeated about 3 times. Then, the precipitate (hyaluronic acid-coated PLA fine particles) was recovered, and lyophilized. The yield of the resulting white powder was 26.3 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 7 µg (proportion of HA-HZ-PLA in the fine particles, 0.03% w/w). DLS measurement (Nicomp370) of the dialyzate showed the measured value of the particle size to be 196.9 nm.

Example 9-7

Preparation-1 of Hyaluronic Acid-Coated PLA Fine Particles by Acetone Solvent Diffusion Method PLA-0005 (40 mg) was weighed, and dissolved in 1 mL of acetone. The solution was added dropwise to, and mixed with, 4 mL of the HA-HZ-PLA aqueous solution, which was prepared in Example 8-1, with stirrer agitation. After stirring for about 15 minutes, the resulting mixed solution was subjected to evaporation to remove acetone. The residue was filtered through a 5.0 µm filter to remove agglomerates, and then a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 14.5 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 104 µg (proportion of HA-HZ-PLA in the fine particles, 0.72% w/w). DLS measurement (Nicomp370) of the solution after evaporation showed the measured value of the particle size to be 367.8 nm.

Example 9-8

Preparation-2 of Hyaluronic Acid-Coated PLA Fine Particles by Acetone Solvent Diffusion Method PLA-0005 (40 mg) was weighed, and dissolved in 1 mL of acetone. The solution was added dropwise to, and mixed with, 4 mL of distilled water with stirrer agitation. After stirring for about 15 minutes, the resulting mixed solution was subjected to evaporation to remove acetone. The residue was filtered through a 5.0 μm filter to remove agglomerates. Then, the filtrate was added dropwise to, and mixed with, 4 mL of the HA-HZ-PLA aqueous solution prepared in Example 8-1. After stirring for about 15 minutes, a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 20.1 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 99 μg (proportion of HA-HZ-PLA in the fine particles, 0.49% w/w). DLS measurement (Nicomp370) of the solution after evaporation showed the measured value of the particle size to be 336.9 nm.

Example 9-9

Preparation-3 of Hyaluronic Acid-Coated PLA Fine Particles by Acetone Solvent Diffusion Method PLA-0005 (40 mg) was weighed, and dissolved in 1 mL of acetone. The solution was added dropwise to, and mixed with, 4 mL of the HA-HZ-PLA aqueous solution, which was prepared in Example 8-2, with stirrer agitation. After stirring for about 15 minutes, the resulting mixed solution was subjected to evaporation to remove acetone. The residue was filtered through a 5.0 μm filter to remove agglomerates, and then a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 20.9 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 18 μg (proportion of HA-HZ-PLA in the fine particles, 0.09% w/w). DLS measurement (Nicomp370) of the solution after evaporation showed the measured value of the particle size to be 328.3 nm.

Example 9-10

Preparation-4 of Hyaluronic Acid-Coated PLA Fine Particles by Acetone Solvent Diffusion Method PLA-0005 (40 mg) was weighed, and dissolved in 1 mL of acetone. The solution was added dropwise to, and mixed with, 4 mL of distilled water with stirrer agitation. After stirring for about 15 minutes, the resulting mixed solution was subjected to evaporation to remove acetone. The residue was filtered through a 5.0 μm filter to remove agglomerates. Then, the filtrate was added dropwise to, and mixed with, 4 mL of the HA-HZ-PLA aqueous solution prepared in Example 8-2. After stirring for about 15 minutes, a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 22.9 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 27 μg (proportion of HA-HZ-PLA in the fine particles, 0.12% w/w). DLS measurement (Nicomp370) of the solution after evaporation showed the measured value of the particle size to be 328.1 nm.

Example 9-11

Preparation-1 of Hyaluronic Acid-Coated PLGA Fine Particles by Emulsion Solvent Evaporation Method PLGA-7520 (Wako Pure Chemical Industries, Ltd.: viscosity average molecular weight 20 kdaltons, lactide ratio 75% mols/mol) was weighed (80 mg), and dissolved in 2 mL of methylene chloride. The solution was mixed with the HA-HZ-PLA aqueous solution prepared in Example 8-1, and the mixture was emulsified (10,000 rpm, 5 min) by use of a rotary homogenizer (POLYTRON PT3100). The emulsion was stirred overnight in an open system by a stirrer to remove methylene chloride. The stirred emulsion was sifted through a 32 μm sieve to remove agglomerates. Then, a washing operation, which comprised centrifugation (1,500 g, 10 min), removal of the supernatant, and addition of distilled water, was repeated about 3 times. Then, the precipitate (hyaluronic acid-coated PLGA fine particles.) was recovered, and lyophilized. The yield of the resulting white powder was 62.1 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 675 μg (proportion of HA-HZ-PLA in the fine particles, 1.09% w/w). The particle size of the fine particles was measured by redispersing the white powder composed of the hyaluronic acid-coated PLA fine particles in distilled water, picking up 50 of the fine particles randomly by optical microscopic observation, and analyzing their images. The mean value of the particle sizes, and the standard deviation were found to be 2.7±1.1 μm.

Example 9-12

Preparation-2 of Hyaluronic Acid-Coated PLGA Fine Particles by Emulsion Solvent Evaporation Method PLGA-7520 was weighed (80 mg), and dissolved in 2 mL of methylene chloride. The solution was mixed with 8 mL of a 1% w/v PVA aqueous solution, and the mixture was emulsified (10,000 rpm, 5 min) by use of a rotary homogenizer (POLYTRON PT3100). The emulsion was stirred overnight in an open system by a stirrer to remove methylene chloride. The stirred emulsion was sifted through a 32 μm sieve to remove agglomerates. Then, a washing operation, which comprised centrifugation (1,500 g, 10 min), removal of the supernatant, and addition of distilled water, was repeated about 3 times. PLGA fine particles obtained as the precipitate and 8 mL of the HA-HZ-PLA aqueous solution prepared in Example 8-1 were mixed, and stirred for about 15 minutes. Then, a washing operation, which comprised centrifugation (1,500 g, 10 min), removal of the supernatant, and addition of distilled water, was repeated again about 3 times. The precipitate (hyaluronic acid-coated PLGA fine particles) was recovered, and lyophilized. The yield of the resulting white powder was 61.3 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 140 µg (proportion of HA-HZ-PLA in the fine particles, 0.23% w/w). The particle size of the fine particles was measured by redispersing the white powder composed of the hyaluronic acid-coated PLGA fine particles in distilled water, picking up 50 of the fine particles randomly by optical microscopic observation, and analyzing their images. The mean value of the particle sizes, and the standard deviation were found to be 1.2±0.2 µm.

Example 9-13

Preparation-3 of Hyaluronic Acid-Coated PLGA Fine Particles by Emulsion Solvent Evaporation Method PLGA-7520 was weighed (80 mg), and dissolved in 2 mL of methylene chloride. The solution was mixed with 8 mL of the HA-HZ-PLA aqueous solution prepared in Example 8-2, and the mixture was emulsified (10,000 rpm, 5 min) by use of a rotary homogenizer (POLYTRON PT3100). The emulsion was stirred overnight in an open system by a stirrer to remove methylene chloride. The stirred emulsion was sifted through a 32 µm sieve to remove agglomerates. Then, a washing operation, which comprised centrifugation (1,500 g, 10 min), removal of the supernatant, and addition of distilled water, was repeated about 3 times. The precipitate (hyaluronic acid-coated PLGA fine particles) was recovered, and lyophilized. The yield of the resulting white powder was 55.0 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 251 µg (proportion of HA-HZ-PLA in the fine particles, 0.46% w/w). Measurement of the particle size was conducted by redispersing the white powder composed of the hyaluronic acid-coated PLGA fine particles in distilled water, picking up 50 of the fine particles randomly by optical microscopic observation, and analyzing their images. The mean value of the particle sizes, and the standard deviation were found to be 3.0±1.2 µm.

Example 9-14

Preparation-4 of Hyaluronic Acid-Coated PLGA Fine Particles by Emulsion Solvent Evaporation Method PLGA-7520 was weighed (80 mg), and dissolved in 2 mL of methylene chloride. The solution was mixed with 8 mL of a 1% w/v PVA aqueous solution, and the mixture was emulsified (10,000 rpm, 5 min) by use of a rotary homogenizer (POLYTRON PT3100). The emulsion was stirred overnight in an open system by a stirrer to remove methylene chloride. The stirred emulsion was sifted through a 32 µm sieve to remove agglomerates. Then, a washing operation, which comprised centrifugation (1,500 g, 10 min), removal of the supernatant, and addition of distilled water, was repeated about 3 times. PLGA fine particles obtained as the precipitate and 8 mL of the HA-HZ-PLA aqueous solution prepared in Example 8-2 were mixed, and stirred for about 15 minutes. Then, a washing operation, which comprised centrifugation (1,500 g, 10 min), removal of the supernatant, and addition of distilled water, was repeated again about 3 times. The precipitate (hyaluronic acid-coated PLGA fine particles) was recovered, and lyophilized. The yield of the resulting white powder was 56.3 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 608 µg (proportion of HA-HZ-PLA in the fine particles, 1.08% w/w). The particle size of the fine particles was measured by redispersing the white powder composed of the hyaluronic acid-coated PLGA fine particles in distilled water, picking up 50 of the fine particles randomly by optical microscopic observation, and analyzing their images. The mean value of the particle sizes, and the standard deviation were found to be 1.7±0.4 µm.

Comparative Example 2

Preparation of PLGA Fine Particles

Comparative Example 2-1

Preparation of PLGA Fine Particles by Emulsion Solvent Evaporation Method

PLGA-7520 was weighed (80 mg), and dissolved in 2 mL of methylene chloride. The solution was mixed with 18 mL of a 1% w/v PVA aqueous solution, and the mixture was emulsified (10,000 rpm, 5 min) by use of a rotary homogenizer (POLYTRON PT3100). The emulsion was stirred overnight in an open system by a stirrer to remove methylene chloride. The stirred emulsion was sifted through a 32 µm sieve to remove agglomerates. Then, a washing operation, which comprised centrifugation (1,500 g, 10 min), removal of the supernatant, and addition of distilled water, was repeated about 3 times. The precipitate (PLGA fine particles) was recovered, and lyophilized. The yield of the resulting white powder was 57.3 mg. Measurement of the particle size was carried out by redispersing the white powder composed of the PLGA fine particles in distilled water, picking up 50 of the fine particles randomly by optical microscopic observation, and analyzing their images. The mean value of the particle sizes, and the standard deviation were found to be 1.7±0.3 µm.

TABLE 9

Method of preparation, conditions for preparation, and results of preparation of fine particles prepared in Example 9

| | Method of preparing fine particles | Organic phase | PLA weight ratio of HA-HZ-PLA (% w/w) | HA coating method (method for using HA-HZ-PLA) | Mean particle size of fine particles | HA-HZ-PLA content (% w/w) |
|---|---|---|---|---|---|---|
| Ex. 9-1 | Dialysis method | DMSO | 29.5 | Dissolve HA-HZ-PLA in organic phase. Spontaneously coat during fine particle formation | 1.0 μm | 0.29 |
| Ex. 9-2 | Solvent diffusion method | DMSO | 36.7 | Dissolve HA-HZ-PLA in aqueous phase. Spontaneously coat during fine particle formation | 225.3 nm | 0.43 |
| Ex. 9-3 | Solvent diffusion method | DMSO | 36.7 | After fine particle preparation, add HA-HZ-PLA aqueous solution | 308.9 nm | 0.09 |
| Ex. 9-4 | Solvent diffusion method | DMSO | 29.5 | Dissolve HA-HZ-PLA in organic phase. Spontaneously coat during fine particle formation | 288.2 nm | 1.89 |
| Ex. 9-5 | Solvent diffusion method | DMSO | 29.5 | Dissolve HA-HZ-PLA in aqueous phase. Spontaneously coat during fine particle formation | 220.2 nm | 0.01 |
| Ex. 9-6 | Solvent diffusion method | DMSO | 29.5 | After fine particle preparation, add HA-HZ-PLA aqueous solution | 196.9 nm | 0.03 |
| Ex. 9-7 | Solvent diffusion method | Acetone | 36.7 | Dissolve HA-HZ-PLA in aqueous phase. Spontaneously coat during fine particle formation | 367.8 nm | 0.72 |
| Ex. 9-8 | Solvent diffusion method | Acetone | 36.7 | After fine particle preparation, add HA-HZ-PLA aqueous solution | 336.9 nm | 0.49 |
| Ex. 9-9 | Solvent diffusion method | Acetone | 29.5 | Dissolve HA-HZ-PLA in aqueous phase. Spontaneously coat during fine particle formation | 328.3 nm | 0.09 |
| Ex. 9-10 | Solvent diffusion method | Acetone | 29.5 | After fine particle preparation, add HA-HZ-PLA aqueous solution | 328.1 nm | 0.12 |
| Ex. 9-11 | Emulsion solvent evaporation method | Methylene chloride | 36.7 | Dissolve HA-HZ-PLA in aqueous phase. Spontaneously coat during emulsion formation | 2.7 μm | 1.09 |
| Ex. 9-12 | Emulsion solvent evaporation method | Methylene chloride | 36.7 | After fine particle preparation, add HA-HZ-PLA aqueous solution | 1.2 μm | 0.23 |
| Ex. 9-13 | Emulsion solvent evaporation method | Methylene chloride | 29.5 | Dissolve HA-HZ-PLA in aqueous phase. Spontaneously coat during emulsion formation | 3.0 μm | 0.46 |
| Ex. 9-14 | Emulsion solvent evaporation method | Methylene chloride | 29.5 | After fine particle preparation, add HA-HZ-PLA aqueous solution | 1.7 μm | 1.08 |

Example 10

Preparation of Hyaluronic Acid-Coated PLA Nanospheres Intended for Prolongation of Blood Residence and Accumulation in Tumor Tissue and Inflammatory Tissue

Example 10-1

Preparation-1 of Hyaluronic Acid-Coated PLA Nanospheres by DMSO Solvent Diffusion Method The HA-HZ-PLA prepared in Example 7-6 (4 mg), and 36 mg of PLA-0005 were weighed, and dissolved in 1 mL of DMSO. The solution was added dropwise to, and mixed with, 4 mL of distilled water with stirrer agitation. The resulting mixed solution was dialyzed against distilled water (MWCO: 10,000, room temperature, 3 days), and the dialyzate was filtered through a 5.0 μm filter to remove agglomerates. Then, a washing operation, which comprised centrifugation (40,000 g, 10 min), removal of the supernatant, and addition of distilled water, was repeated about 3 times. Then, the precipitate (hyaluronic acid-coated PLA fine particles) was recovered, and lyophilized. The yield of the resulting white powder was 27.8 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 2,178 μg (proportion of HA-HZ-PLA in the fine particles, 7.82% w/w). Measurement of the particle size was conducted by DLS measurement (Nicomp370) of the dialyzate. The particle size was found to be 304.0 nm.

Example 10-2

Preparation-2 of Hyaluronic Acid-Coated PLA Nanospheres by DMSO Solvent Diffusion Method PLA-0005 was weighed (40 mg), and dissolved in 1 mL of DMSO. The solution was added dropwise to, and mixed with, 4 mL of the HA-HZ-PLA aqueous solution, which was prepared in Example 8-3, with stirrer agitation. The resulting mixed solution was dialyzed against distilled water (MWCO: 10,000, room temperature, 3 days), and the dialyzate was filtered through a 5.0 μm filter to remove agglomerates. Then, a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 240 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 1,257 μg (proportion of HA-HZ-PLA in the fine particles, 5.24% w/w). Measurement of the particle size was conducted by DLS measurement (Nicomp370) of the dialyzate. The particle size was found to be 166.9 nm.

Example 10-3

Preparation-3 of Hyaluronic Acid-Coated PLA Nanospheres by DMSO Solvent Diffusion Method PLA-0005 was weighed (40 mg), and dissolved in 1 mL of DMSO. The solution was added dropwise to, and mixed with, 4 mL of distilled water with stirrer agitation. The resulting mixed solution was dialyzed against distilled water (MWCO: 10,000, room temperature, 3 days), and the dialyzate was filtered through a 5.0 μm filter to remove agglomerates. Then, the filtrate was added dropwise to, and mixed with, 4 mL of the HA-HZ-PLA aqueous solution prepared in Example 8-3, and the mixture was stirred for about 15 minutes. Then, a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 26.6 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 841 μg (proportion of HA-HZ-PLA in the fine particles, 3.16% w/w). Measurement of the particle size was conducted by DLS measurement (Nicomp370) of the dialyzate. The particle size was found to be 198.3 nm.

Example 10-4

Preparation-4 of Hyaluronic Acid-Coated PLA Nanospheres by DMSO Solvent Diffusion Method PLA-0005 was weighed (40 mg), and dissolved in 1 mL of DMSO. The solution was added dropwise to, and mixed with, 4 mL of the HA-HZ-PLA aqueous solution, which was prepared in Example 8-4, with stirrer agitation. The resulting mixed solution was dialyzed against distilled water (MWCO: 10,000, room temperature, 3 days), and the dialyzate was filtered through a 5.0 μm filter to remove agglomerates. Then, a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 35.0 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 3,581 μg (proportion of HA-HZ-PLA in the fine particles, 10.23% w/w). DLS measurement (Nicomp370) of the dialyzate was performed, showing the particle size to be 183.5 nm.

Example 10-5

Preparation-5 of Hyaluronic Acid-Coated PLA Nanospheres by DMSO Solvent Diffusion Method PLA-0005 was weighed (40 mg), and dissolved in 1 mL of DMSO. The solution was added dropwise to, and mixed with, 4 mL. of distilled water with stirrer agitation. The resulting mixed solution was dialyzed against distilled water (MWCO: 10,000, room temperature, 3 days), and the dialyzate was filtered through a 5.0 μm filter to remove agglomerates. Then, the filtrate was added dropwise to, and mixed with, 4 mL of the HA-HZ-PLA aqueous solution prepared in Example 8-4, and the mixture was stirred for about 15 minutes. Then, a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 28.2 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 342 µg (proportion of HA-HZ-PLA in the fine particles, 1.21% w/w). DLS measurement (Nicomp370) of the dialyzate was performed, and the particle size was found to be 70.4 nm.

Example 10-6

Preparation-1 of Hyaluronic Acid-Coated PLA Nanospheres by Acetone Solvent Diffusion Method PLA-0005 (10 mg) was weighed, and dissolved in 2 mL of acetone. The solution was added dropwise to, and mixed with, 2 mL of the HA-HZ-PLA aqueous solution, which was prepared in Example 8-3, with stirrer agitation. After stirring for about 15 minutes, the resulting mixed solution was subjected to evaporation to remove acetone. The residue was filtered through a 5.0 µm filter to remove agglomerates, and then a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 7.9 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 882 µg (proportion of HA-HZ-PLA in the fine particles, 11.15% w/w). DLS measurement (Nicomp370) of the solution after evaporation showed the measured value of the particle size to be 198.3 nm.

Example 10-7

Preparation-2 of Hyaluronic Acid-Coated PLA Nanospheres by Acetone Solvent Diffusion Method PLA-0005 (10 mg) was weighed, and dissolved in 2 mL of acetone. The solution was added dropwise to, and mixed with, 2 mL of distilled water with stirrer agitation. After stirring for about 15 minutes, the resulting mixed solution was subjected to evaporation to remove acetone. The residue was filtered through a 5.0 µm filter to remove agglomerates. Then, the filtrate was added dropwise to, and mixed with, 2 mL of the HA-HZ-PLA aqueous solution prepared in Example 8-3. After stirring for about 15 minutes, a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 36 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 137 µg (proportion of HA-HZ-PLA in the fine particles, 3.83% w/w). DLS measurement (Nicomp370) of the solution after evaporation showed the measured value of the particle size to be 195.6 nm.

Example 10-8

Preparation-3 of Hyaluronic Acid-Coated PLA Nanospheres by Acetone Solvent Diffusion Method PLA-0005 (10 mg) was weighed, and dissolved in 2 mL of acetone. The solution was added dropwise to, and mixed with, 2 mL of the HA-HZ-PLA aqueous solution, which was prepared in Example 8-4, with stirrer agitation. After stirring for about 15 minutes, the resulting mixed solution was subjected to evaporation to remove acetone. The residue was filtered through a 5.0 µm filter to remove agglomerates, and then a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 7.2 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 1063 µg (proportion of HA-HZ-PLA in the fine particles, 14.85% w/w). DLS measurement (Nicomp370) of the solution after evaporation showed the measured value of the particle size to be 163.1 nm.

Example 10-9

Preparation-4 of Hyaluronic Acid-Coated PLA Nanospheres by Acetone Solvent Diffusion Method PLA-0005 (10 mg) was weighed, and dissolved in 2 mL of acetone. The solution was added dropwise to, and mixed with, 2 mL of distilled water with stirrer agitation. After stirring for about 15 minutes, the resulting mixed solution was subjected to evaporation to remove acetone. The residue was filtered through a 5.0 µm filter to remove agglomerates. Then, the filtrate was added dropwise to, and mixed with, 2 mL of the HA-HZ-PLA aqueous solution prepared in Example 8-4. After stirring for about 15 minutes, a washing operation, which comprised centrifugation (40,000 g, 10 min), removal of the supernatant, and addition of distilled water, was repeated about 3 times. The precipitate (hyaluronic acid-coated PLA fine particles) was recovered, and lyophilized. The yield of the resulting white powder was 7.9 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 398 µg (proportion of HA-HZ-PLA in the fine particles, 5.04% w/w). DLS measurement (Nicomp370) of the solution after evaporation showed the measured value of the particle size to be 182.1 nm.

TABLE 10

Method of preparation, conditions for preparation, and results of preparation of fine particles prepared in Example 10

| | Method of preparing fine particles | Organic phase | PLA weight ratio of HA-HZ-PLA (% w/w) | HA coating method (method for using HA-HZ-PLA) | Mean particle size of fine particles | HA-HZ-PLA content (% w/w) |
|---|---|---|---|---|---|---|
| Ex. 10-1 | Solvent diffusion method | DMSO | 65.1 | Dissolve HA-HZ-PLA in organic phase. Spontaneously coat during fine particle formation | 304.0 μm | 7.82 |
| Ex. 10-2 | Solvent diffusion method | DMSO | 21.1 | Dissolve HA-HZ-PLA in aqueous phase. Spontaneously coat during fine particle formation | 166.9 nm | 5.24 |
| Ex. 10-3 | Solvent diffusion method | DMSO | 21.1 | After fine particle preparation, add HA-HZ-PLA aqueous solution | 198.3 nm | 3.16 |
| Ex. 10-4 | Solvent diffusion method | DMSO | 65.1 | Dissolve HA-HZ-PLA in aqueous phase. Spontaneously coat during fine particle formation | 183.5 nm | 10.23 |
| Ex. 10-5 | Solvent diffusion method | DMSO | 65.1 | After fine particle preparation, add HA-HZ-PLA aqueous solution | 70.4 nm | 1.21 |
| Ex. 10-6 | Solvent diffusion method | Acetone | 21.1 | Dissolve HA-HZ-PLA in aqueous phase. Spontaneously coat during fine particle formation | 198.3 nm | 11.15 |
| Ex. 10-7 | Solvent diffusion method | Acetone | 21.1 | After fine particle preparation, add HA-HZ-PLA aqueous solution | 195.6 nm | 3.83 |
| Ex. 10-8 | Solvent diffusion method | Acetone | 65.1 | Dissolve HA-HZ-PLA in aqueous phase. Spontaneously coat during fine particle formation | 163.1 nm | 14.85 |
| Ex. 10-9 | Solvent diffusion method | Acetone | 65.1 | After fine particle preparation, add HA-HZ-PLA aqueous solution | 182.1 nm | 5.04 |

Example 11

Preparation of Hyaluronic Acid-Coated PLGA Microspheres Intended for Reducing Local Irritation Example 11-1

Preparation-1 of Hyaluronic Acid-Coated PLGA Microspheres by Dialysis Method

Hyaluronic acid-coated PLGA microspheres were prepared by the same procedure as in Example 9-1.

Example 11-2

Preparation-1 of Hyaluronic Acid-Coated PLGA Microspheres by Emulsion Solvent Evaporation Method PLGA-7520 was weighed (80 mg), and dissolved in 2 mL of methylene chloride. The solution was mixed with 8 mL of the HA-HZ-PLA aqueous solution prepared in Example 8-1, and the mixture was emulsified (400 rpm, 15 min) by use of a mechanical stirrer (EYEL4, MAZERA Z). The emulsion was stirred overnight in an open system by a stirrer to remove methylene chloride. The stirred emulsion was sifted through a 300 μm sieve to remove agglomerates. Then, a washing operation, which comprised centrifugation (1,500 g, 10 min), removal of the supernatant, and addition of distilled water, was repeated about 3 times. The precipitate (hyaluronic acid-coated PLGA fine particles) was recovered, and lyophilized. The yield of the resulting white powder was 52.4 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 28 μg (proportion of HA-HZ-PLA in the fine particles, 0.05% w/w). The particle size of the fine particles was measured by redispersing the white powder composed of the hyaluronic acid-coated PLGA fine particles in distilled water, picking up 50 of the fine particles randomly by optical microscopic observation, and analyzing their images. The mean value of the particle sizes, and the standard deviation were found to be 6.8±3.6 μm.

Example 11-3

Preparation-2 of Hyaluronic Acid-Coated PLGA Microspheres by Emulsion Solvent Evaporation Method PLGA-7520 was weighed (80 mg), and dissolved in 2 mL of methylene chloride. The solution was mixed with 8 mL of a 1% w/v PVA aqueous solution, and the mixture was emulsified (400 rpm, 15 min) by use of a mechanical stirrer (EYEL4, MAZERA Z). The emulsion was stirred overnight in an open system by a stirrer to remove methylene chloride. The stirred emulsion was sifted through a 300 μm sieve to remove agglomerates. Then, a washing operation, which comprised centrifugation (1,500 g, 10 min), removal of the supernatant, and addition of distilled water, was repeated about 3 times. PLGA fine particles obtained as the precipitate, and 8 mL of the HA-HZ-PLA aqueous solution prepared in Example 8-1 were mixed, and the mixture was stirred for about 15 minutes. Then, a washing operation, which comprised centrifugation (1,500 g, 10 min), removal of the supernatant, and addition of distilled water, was repeated again about 3 times. The precipitate (hyaluronic acid-coated PLGA fine particles) was recovered, and lyophilized. The yield of the resulting white powder was 58.8 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 188 µg (proportion of HA-HZ-PLA in the fine particles, 0.32% w/w). The particle size of the fine particles was measured by redispersing the white powder composed of the hyaluronic acid-coated PLGA fine particles in distilled water, picking up 50 of the fine particles randomly by optical microscopic observation, and analyzing their images. The mean value of the particle sizes, and the standard deviation were found to be 7.4±2.7 µm.

Example 11-4

Preparation-3 of Hyaluronic Acid-Coated PLGA Microspheres by Emulsion Solvent Evaporation Method PLGA-7520 was weighed (80 mg), and dissolved in 2 mL of methylene chloride. The solution was mixed with 8 mL of the HA-HZ-PLA aqueous solution prepared in Example 8-2, and the mixture was emulsified (400 rpm, 15 min) by use of a mechanical stirrer (EYEL4, MAZERA Z). The emulsion was stirred overnight in an open system by a stirrer to remove methylene chloride. The stirred emulsion was sifted through a 300 µm sieve to remove agglomerates. Then, a washing operation, which comprised centrifugation (1,500 g, 10 min), removal of the supernatant, and addition of distilled water, was repeated about 3 times. The precipitate (hyaluronic acid-coated PLGA fine particles) was recovered, and lyophilized. The yield of the resulting white powder was 55.4 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 83 µg (proportion of HA-HZ-PLA in the fine particles, 0.15% w/w). The particle size of the fine particles was measured by redispersing the white powder composed of the hyaluronic acid-coated PLGA fine particles in distilled water, picking up 50 of the fine particles randomly by optical microscopic observation, and analyzing their images. The mean value of the particle sizes, and the standard deviation were found to be 6.8±3.3 µm.

Example 11-5

Preparation-4 of Hyaluronic Acid-Coated PLGA Microspheres by Emulsion Colvent Evaporation Method PLGA-7520 was weighed (80 mg), and dissolved in 2 mL of methylene chloride. The solution was mixed with 8 mL of a 1% w/v PVA aqueous solution, and the mixture was emulsified (400 rpm, 15 min) by use of a mechanical stirrer (EYEL4, MAZERA Z). The emulsion was stirred overnight in an open system by a stirrer to remove methylene chloride. The stirred emulsion was sifted through a 300 µm sieve to remove agglomerates. Then, a washing operation, which comprised centrifugation (1,500 g, 10 min), removal of the supernatant, and addition of distilled water, was repeated about 3 times. PLGA fine particles obtained as the precipitate, and 8 mL of the HA-HZ-PLA aqueous solution prepared in Example 8-2 were mixed, and the mixture was stirred for about 15 minutes. Then, a washing operation, which comprised centrifugation (1,500 g, 10 min), removal of the supernatant, and addition of distilled water, was repeated again about 3 times. The precipitate (hyaluronic acid-coated PLGA fine particles) was recovered, and lyophilized. The yield of the resulting white powder was 60.8 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 83 µg (proportion of HA-HZ-PLA in the fine particles, 0.14% w/w). The particle sizes of the fine particles were measured by redispersing the white powder composed of the hyaluronic acid-coated PLGA fine particles in distilled water, picking up 50 of the fine particles randomly by optical microscopic observation, and analyzing their images. The mean value of the particle sizes, and the standard deviation were found to be 7.8±5.4 µm.

Example 11-6

Preparation-1 of Hyaluronic Acid-Coated PLGA Microspheres by Dialysis Method

The HA-HZ-PLA prepared in Example 7-6 (12 mg), and 108 mg of PLA-0005 were weighed, and dissolved in 3 mL of DMSO. The solution was dialyzed against distilled water (MWCO:10,000, room temperature, 3 days), and the dialyzate was sifted through a 32 µm sieve to remove agglomerates. Then, a washing operation, which comprised centrifugation (1,500 g, 10 min), removal of the supernatant, and addition of distilled water, was repeated about 3 times. The precipitate (hyaluronic acid-coated PLA fine particles) was recovered, and lyophilized. The yield of the resulting white powder was 91.7 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 2,560 µg (proportion of HA-HZ-PLA in the fine particles, 2.79% w/w). The particle sizes of the fine particles were measured by redispersing the white powder composed of the hyaluronic acid-coated PLA fine particles in distilled water, picking up 50 of the fine particles randomly by optical microscopic observation, and analyzing their images. The mean value of the particle sizes, and the standard deviation were found to be 1.6±0.4 µm.

Example 11-7

Preparation-5 of Hyaluronic Acid-Coated PLGA Microspheres by Emulsion Solvent Evaporation Method PLGA-7520 was weighed (80 mg), and dissolved in 2 mL of methylene chloride. The solution was mixed with 8 mL of the HA-HZ-PLA aqueous solution prepared in Example 8-3, and the mixture was emulsified (400 rpm, 15 min) by use of a mechanical stirrer (EYEL4, MAZERA Z). The emulsion was stirred overnight in an open system by a stirrer to remove methylene chloride. The stirred emulsion was sifted through a 300 μm sieve to remove agglomerates. Then, a washing operation, which comprised centrifugation (1,500 g, 10 min), removal of the supernatant, and addition of distilled water, was repeated about 3 times. The precipitate (hyaluronic acid-coated PLGA fine particles) was recovered, and lyophilized. The yield of the resulting white powder was 580 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 261 μg (proportion of HA-HZ-PLA in the fine particles, 0.45% w/w). The particle sizes of the fine particles were measured by redispersing the white powder composed of the hyaluronic acid-coated PLGA fine particles in distilled water, picking up 50 of the fine particles randomly by optical microscopic observation, and analyzing their images. The mean value of the particle sizes, and the standard deviation were found to be 6.1±6.2 μm.

Example 11-8

Preparation-6 of Hyaluronic Acid-Coated PLGA Microspheres by Emulsion Solvent Evaporation Method PLGA-7520 was weighed (80 mg), and dissolved in 2 mL of methylene chloride. The solution was mixed with 8 mL of a 1% w/v PVA aqueous solution, and the mixture was emulsified (400 rpm, 15 min) by use of a mechanical stirrer (EYEL4, MAZERA Z). The emulsion was stirred overnight in an open system by a stirrer to remove methylene chloride. The stirred emulsion was sifted through a 300 μm sieve to remove agglomerates. Then, a washing operation, which comprised centrifugation (1,500 g, 10 min), removal of the supernatant, and addition of distilled water, was repeated about 3 times. PLGA fine particles obtained as the precipitate, and 8 mL of the HA-HZ-PLA aqueous solution prepared in Example 8-3 were mixed, and the mixture was stirred for about 15 minutes. Then, a washing operation, which comprised centrifugation (1,500 g, 10 min), removal of the supernatant, and addition of distilled water, was repeated again about 3 times. The precipitate (hyaluronic acid-coated PLGA fine particles) was recovered, and lyophilized. The yield of the resulting white powder was 58.6 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 158 μg (proportion of HA-HZ-PLA in the fine particles, 0.27% w/w). The particle sizes of the fine particles were measured by redispersing the white powder composed of the hyaluronic acid-coated PLGA fine particles in distilled water, picking up 50 of the fine particles randomly by optical microscopic observation, and analyzing their images. The mean value of the particle sizes, and the standard deviation were found to be 7.7±5.7 μm.

Example 11-9

Preparation-7 of Hyaluronic Acid-Coated PLGA Microspheres by Emulsion Solvent Evaporation Method PLGA-7520 was weighed (80 mg), and dissolved in 2 mL of methylene chloride. The solution was mixed with 8 mL of the HA-HZ-PLA aqueous solution prepared in Example 8-4, and the mixture was emulsified (400 rpm, 15 min) by use of a mechanical stirrer (EYEL4, MAZERA Z). The emulsion was stirred overnight in an open system by a stirrer to remove methylene chloride. The stirred emulsion was sifted through a 300 μm sieve to remove agglomerates. Then, a washing operation, which comprised centrifugation (1,500 g, 10 min), removal of the supernatant, and addition of distilled water, was repeated about 3 times. The precipitate (hyaluronic acid-coated PLGA fine particles) was recovered, and lyophilized. The yield of the resulting white powder was 57.5 mg. This white powder was thoroughly washed with an excess of acetone, and centrifuged (10,000 g, 10 min). The supernatant was removed, and the insolubles (HA-HZ-PLA) were dried under reduced pressure. The weight of the resulting fine particles was found to be 3,068 μg (proportion of HA-HZ-PLA in the fine particles, 5.34% w/w). The particle sizes of the fine particles were measured by redispersing the white powder composed of the hyaluronic acid-coated PLGA fine particles in distilled water, picking up 50 of the fine particles randomly by optical microscopic observation, and analyzing their images. The mean value of the particle sizes, and the standard deviation were found to be 6.9±3.5 μm.

Example 11-10

Preparation-8 of Hyaluronic Acid-Coated PLGA Microspheres by Emulsion Solvent Evaporation Method PLGA-7520 was weighed (80 mg), and dissolved in 2 mL of methylene chloride. The solution was mixed with 8 mL of a 1% w/v PVA aqueous solution, and the mixture was emulsified (400 rpm, 15 min) by use of a mechanical stirrer (EYEL4, MAZERA Z). The emulsion was stirred overnight in an open system by a stirrer to remove methylene chloride. The stirred emulsion was sifted through a 300 μm sieve to remove agglomerates. Then, a washing operation, which comprised centrifugation (1,500 g, 10 min), removal of the supernatant, and addition of distilled water, was repeated about 3 times. PLGA fine particles obtained as the precipitate, and 8 mL of the HA-HZ-PLA aqueous solution prepared in Example 8-4 were mixed, and the mixture was stirred for about 15 minutes. Then, a washing operation, which comprised centrifugation (1,500 g, 10 min), removal of the supernatant, and addition of distilled water, was repeated again about 3 times. The precipitate (hyaluronic acid-coated PLGA fine particles) was recovered, and lyophilized. The yield of the resulting white powder was 65.0 mg. This white powder was thoroughly washed with an excess of acetone, and then centrifuged (10,000 g, 10 min). The supernatant was removed, and the insolubles (HA-HZ-PLA) were dried under reduced pressure. The weight of the resulting fine particles was found to be 390 μg (proportion of HA-HZ-PLA in the fine particles, 0.60% w/w). The particle sizes of the fine particles were measured by redispersing the white powder composed of the hyaluronic acid-coated PLGA fine particles in distilled water, picking up 50 of the fine particles randomly by optical microscopic observation, and analyzing their images. The mean value of the particle sizes, and the standard deviation were found to be 5.6±2.3 μm.

Comparative Example 3

Preparation of PLGA Microspheres

Comparative Example 3-1

Preparation of PLGA Microspheres by Emulsion Solvent Evaporation Method

PLGA-7520 was weighed (80 mg), and dissolved in 2 mL of methylene chloride. The solution was mixed with 18 mL of a 1% w/v PVA aqueous solution, and the mixture was emulsified (400 rpm, 15 min) by use of a mechanical stirrer (EYEL4, MAZERA Z). The emulsion was stirred overnight in an open system by a stirrer to remove methylene chloride. The stirred emulsion was sifted through a 300 μm sieve to remove agglomerates. Then, a washing operation, which comprised centrifugation (1,500 g, 10 min), removal of the supernatant, and addition of distilled water, was repeated about 3 times. The precipitate (PLGA fine particles) was recovered, and lyophilized. The yield of the resulting white powder was 53.9 mg. The particle sizes of the fine particles were measured by redispersing the white powder composed of the PLGA fine particles in distilled water, picking up 50 of the fine particles randomly by optical microscopic observation, and analyzing their images. The mean value of the particle sizes, and the standard deviation were found to be 5.3±2.5 μm.

TABLE 11

Method of preparation, conditions for preparation, and results of preparation of fine particles prepared in Example 11

| | Method of preparing fine particles | Organic phase | PLA weight ratio of HA-HZ-PLA (% w/w) | HA coating method (method for using HA-HZ-PLA) | Mean particle size of fine particles | HA-HZ-PLA content (% w/w) |
|---|---|---|---|---|---|---|
| Ex. 11-1 | Dialysis method | DMSO | 29.5 | Dissolve HA-HZ-PLA in organic phase. Spontaneously coat during fine particle formation | 1.0 μm | 0.29 |
| Ex. 11-2 | Emulsion solvent evaporation method | Methylene chloride | 36.7 | Dissolve HA-HZ-PLA in aqueous phase. Spontaneously coat during fine particle formation | 6.8 μm | 0.05 |
| Ex. 11-3 | Emulsion solvent evaporation method | Methylene chloride | 36.7 | After fine particle preparation, add HA-HZ-PLA aqueous solution | 7.4 μm | 0.32 |
| Ex. 11-4 | Emulsion solvent evaporation method | Methylene chloride | 29.5 | Dissolve HA-HZ-PLA in aqueous phase. Spontaneously coat during fine particle formation | 6.8 μm | 0.15 |
| Ex. 11-5 | Emulsion solvent evaporation method | Methylene chloride | 29.5 | After fine particle preparation, add HA-HZ-PLA aqueous solution | 7.8 μm | 0.14 |
| Ex. 11-6 | Dialysis method | DMSO | 65.1 | Dissolve HA-HZ-PLA in organic phase. Spontaneously coat during fine particle formation | 1.6 μm | 2.79 |
| Ex. 11-7 | Emulsion solvent evaporation method | Methylene chloride | 21.1 | Dissolve HA-HZ-PLA in aqueous phase. Spontaneously coat during fine particle formation | 6.1 μm | 0.45 |
| Ex. 11-8 | Emulsion solvent evaporation method | Methylene chloride | 21.1 | After fine particle preparation, add HA-HZ-PLA aqueous solution | 7.7 μm | 0.27 |
| Ex. 11-9 | Emulsion solvent evaporation method | Methylene chloride | 65.1 | Dissolve HA-HZ-PLA in aqueous phase. Spontaneously coat during fine particle formation | 6.9 μm | 5.34 |
| Ex. 11-10 | Emulsion solvent evaporation method | Methylene chloride | 65.1 | After fine particle preparation, add HA-HZ-PLA aqueous solution | 5.6 μm | 0.60 |

Example 12

Encapsulation of Hyaluronic Acid-Coated PLA Nanospheres in Paclitaxel (PTX)

Example 12-1

Preparation-1 by Acetone Solvent Diffusion Method

Paclitaxel (may hereinafter be referred to as PTX) (Natural Pharmaceuticals, Inc., Lot No. 150206602-1) was weighed (10 mg), and dissolved in 2 mL of acetone. PLA-0005 was weighed (9.0 mg), and dissolved in the acetone solution of PTX. The solution was added dropwise to, and mixed with, 2 mL of the HA-HZ-PLA aqueous solution, which was prepared by the same method as in Example 7-6 and obtained by the same method as in Example 8-4, with stirrer agitation. After stirring for about 15 minutes, the resulting mixed solution was subjected to evaporation to remove acetone. Then, the residue was purified by a desalting column (PD-10), and centrifuged (40,000 g, 10 min). The precipitate (PTX-encapsulating hyaluronic acid-coated PLA fine particles) was recovered, and lyophilized. The yield of the resulting white powder was 8.3 mg. Measurement of the particle size was conducted by DLS measurement (Nicomp370) of the solution after evaporation, whereby the particle size was found to be 99.0±41.3 μm. The resulting white powder was weighed (6.8 mg), thoroughly washed with an excess of acetone, and then centrifuged (10,000 g, 10 min). The supernatant was removed, and the residue was dried under reduced pressure. The weight of the resulting fine particles was found to be 1.3 mg (proportion of HA-HZ-PLA in the fine particles, 19.1% w/w).

Determination of PTX was performed by the internal standard (IS) method using reversed phase chromatography (RP-HPLC). As an IS solution, an acetonitrile solution of about 0.7 mg/mL of n-hexyl-p-hydroxybenzoate was prepared. As standard solutions for drawing a calibration curve, 1:5 serial dilutions (eight dilutions) of an acetonitrile solution of 10 mg/mL PTX were prepared. The white powder composed of the PTX-encapsulating hyaluronic acid-coated PLA fine particles was weighed (1.5 mg), and 1 mL acetonitrile was added. After thorough stirring, the mixture was centrifuged (10,000 g, 10 min), and the supernatant was used as a solution for determination of the PTX concentration. The IS solution was mixed in a proportion of 25 μL to 400 μL of the standard solution and the solution for determination of the PTX concentration, and RP-HPLC measurement was carried out. The PTX content of the nanospheres was 9.9% w/w. The conditions for the RP-HPLC measurement are as follows:

RP-HPLC Conditions
Column: Cadenza-C-18C (Imtakt)
Flow rate: 0.75 mL/min
Eluant:
A: MeCN, B: Ultrapure water (MilliQ water)
A:B=
50:50 (0-10 min, isocratic)
50:50→0:100 (10-12 min, linear gradient)
0:100 (12-19 min, isocratic)
0:100→50:50 (19-20 min, linear gradient)
50:50 (20-25 min, isocratic) Total 25 minutes
Detector: UV (230 nm)
Column temperature: 40° C.
Sample temperature: 4° C.
Amount of sample injected: 10 μL

Example 12-2

Preparation-2 by Acetone Solvent Diffusion Method

PTX was weighed (10 mg), and dissolved in 2 mL of acetone. PLA-0005 was weighed (9.0 mg), and dissolved in the acetone solution of PTX. The solution was added dropwise to, and mixed with, 2 mL of distilled water with stirrer agitation. After stirring for about 15 minutes, the resulting mixed solution was subjected to evaporation to remove acetone. Then, the residue was added dropwise to, and mixed with, 2 mL of the HA-HZ-PLA aqueous solution which was prepared by the same method as in Example 7-6 and obtained by the same method as in Example 8-4. After stirring for about 15 minutes, the mixture was purified by a desalting column (PD-10), and centrifuged (40,000 g, 10 min). The precipitate (PTX-encapsulating hyaluronic acid-coated PLA fine particles) was recovered, and lyophilized. The yield of the resulting white powder was 8.4 mg. Measurement of the particle size was conducted by DLS measurement (Nicomp370) of the solution after evaporation, whereby the particle size was found to be 142.7±44.4 nm. The resulting white powder was weighed (6.9 mg), thoroughly washed with an excess of acetone, and then centrifuged (10,000 g, 10 min). The supernatant was removed, and the residue was dried under reduced pressure. The weight of the resulting fine particles was found to be 0.7 mg (proportion of HA-HZ-PLA in the fine particles, 10.7% w/w). Determination of PTX was performed in the same manner as in Example 12-1, showing that the PTX content of the nanospheres was 9.9% w/w.

INDUSTRIAL APPLICABILITY

A hyaluronic acid modification product comprising hyaluronic acid or its derivative, and a polymer bonded together, the polymer being selected from polylactic acid, polyglycolic acid and lactic acid-glycolic acid copolymer, according to the present invention, can provide a drug carrier which encapsulates a low molecular drug efficiently, which can control a sustained release period for a long term, which can control blood residence, which is well dispersible in an aqueous solution, and which is not problematical in safety. The hyaluronic acid modification product of the present invention also provides a drug carrier comprising injectable fine particles minimal in agglomeration between the particles, and having excellent biocompatibility.

The invention claimed is:
1. A hyaluronic acid modification product,
in which one or more polymers are introduced into glucuronic acid moieties in hyaluronic acid or a derivative thereof, the one or more polymers being selected from the group consisting of polylactic acid, polyglycolic acid, and lactic acid-glycolic acid copolymer;
wherein said hyaluronic acid modification product has resistance to degradation by hyaluronidase compared with an unmodified hyaluronic acid; and
wherein the polymer is bonded to the carboxyl group of the hyaluronic acid or derivative thereof by an amide bond via a spacer, resulting in a repeating structure of the formula (I):

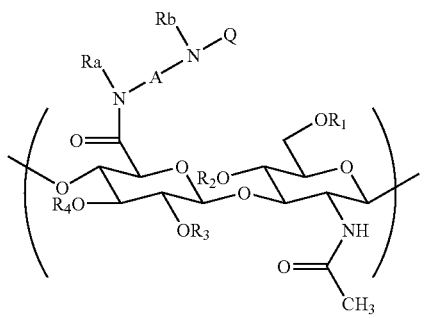

where $R_1$, $R_2$, $R_3$ and $R_4$ are independently selected from the group consisting of a hydrogen atom, a $C_{1-6}$ alkyl group, and a $C_{1-6}$ alkylcarbonyl group, Ra and Rb are independently selected from the group consisting of a hydrogen atom and a $C_{1-6}$ alkyl group, Q is a polymer selected from the group consisting of polylactic acid, polyglycolic acid, and lactic acid-glycolic acid copolymer, and the polymer forms an amide bond with nitrogen at a terminal carboxyl group thereof, A is a single bond, —$(CH_2)_m$—, —$CH_2$—$CH_2$—(O—$CH_2$—$CH_2)_m$—, or —NHCO—$(CH_2)_n$—CONH—, m is an integer of 1 to 10, and n is an integer of 0 to 10;

wherein a repeating structure represented by the formula (I) is contained in a molecule of the hyaluronic acid modification product;

wherein the molecule of the hyaluronic acid modification product optionally contains a repeating structure of the formula (II):

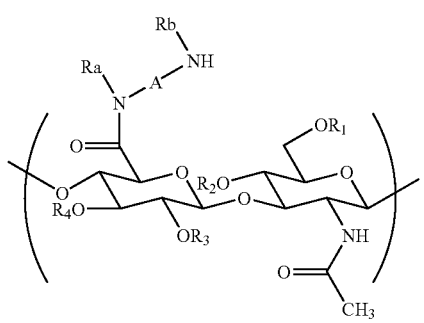

where $R_1$, $R_2$, $R_3$, and $R_4$ are independently selected from the group consisting of a hydrogen atom, a $C_{1-6}$ alkyl group, and a $C_{1-6}$ alkylcarbonyl group, Ra and Rb are independently a hydrogen atom or a $C_{1-6}$ alkyl group, A is a single bond, —$(CH_2)_m$—, —$CH_2$—$CH_2$—(O—$CH_2$—$C_2)_m$—, or —NHCO—$(CH_2)_n$—CONH—, m is an integer of 1 to 10, and n is an integer of 0 to 10; and wherein carboxylic groups in glucuronic acid moieties of hyaluronic acid or a derivative thereof are modified to give the repeating structures represented by the formula (I) or (II) at a modification rate of 50% or more, of at least one repeating structure of formula (I) and optionally at least one repeating structure of formula (II); or a pharmaceutically acceptable salt thereof.

2. The hyaluronic acid modification product or a pharmaceutically acceptable salt thereof according to claim 1, wherein Ra and Rb are each a hydrogen atom, and A is —$(CH_2)_m$—, —$CH_2$—$CH_2$—(O—$CH_2$—$CH_2)_m$—, or —NHCO—$(CH_2)_n$—CONH—.

3. The hyaluronic acid modification product or a pharmaceutically acceptable salt thereof according to claim 1, which has a mean blood residence time of 18 hours or more in a mammal.

4. The hyaluronic acid modification product or a pharmaceutically acceptable salt thereof according to claim 1, wherein the hyaluronic acid derivative contains in a molecule at least one repeating structure of the formula (II):

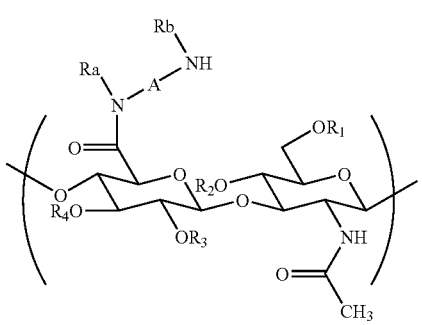

where $R_1$, $R_2$, $R_3$, and $R_4$ are independently selected from a hydrogen atom, a $C_{1-6}$ alkyl group, and a $C_{1-6}$ alkylcarbonyl group, Ra and Rb are independently selected from a hydrogen atom and a $C_{1-6}$ alkyl group, A is a single bond, —$(CH_2)_m$—, —$CH_2$—$CH_2$—(O—$CH_2$—$CH_2)_m$—, or —NHCO—$(CH_2)_n$—CONH—, m is an integer of 1 to 10, and n is an integer of 0 to 10.

5. The hyaluronic acid modification product or a pharmaceutically acceptable salt thereof according to claim 1, wherein carboxylic groups in glucuronic acid moieties of hyaluronic acid or a derivative thereof are modified at a modification rate of 58% to 94%.

6. The hyaluronic acid modification product or a pharmaceutically acceptable salt thereof according to claim 1, wherein carboxylic groups in glucuronic acid moieties of hyaluronic acid or a derivative thereof are modified at a modification rate of 50% to 90%.

7. A process for producing the hyaluronic acid modification product or a pharmaceutically acceptable salt thereof according to claim 1, comprising the step of reacting a polymer with a hyaluronic acid derivative, the polymer having a carboxyl group at a terminal thereof and being selected from polylactic acid, polyglycolic acid, and lactic acid-glycolic acid copolymer, the hyaluronic acid derivative containing in a molecule at least one repeating structure of the formula (II):

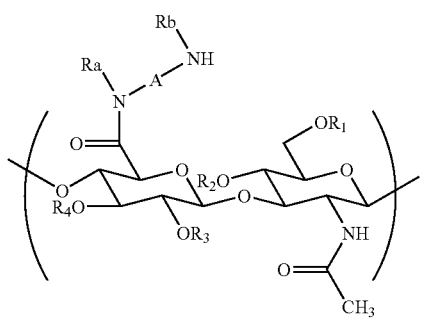
(II)
where $R_1$, $R_2$, $R_3$, and $R_4$ are independently selected from a hydrogen atom, a $C_{1-6}$ alkyl group, and a $C_{1-6}$ alkyl-carbonyl group,
Ra and Rb are independently selected from a hydrogen atom and a $C_{1-6}$ alkyl group,
A is a single bond, $-(CH_2)_m-$, $-CH_2-CH_2-(O-CH_2-CH_2)_m-$, or $-NHCO-(CH_2)_n-CONH-$,
m is an integer of 1 to 10, and
n is an integer of 0 to 10.
* * * * *